US008133973B2

(12) United States Patent
Grandi et al.

(10) Patent No.: US 8,133,973 B2

(45) Date of Patent: Mar. 13, 2012

(54) **IMMUNOGENIC COMPOSITIONS FOR *CHLAMYDIA TRACHOMATIS***

(75) Inventors: Guido Grandi, Siena (IT); Giulio Ratti, Siena (IT)

(73) Assignee: Novartis Vaccines and Diagnostics, S.r.l., Siena (IT)

( * ) Notice: Subject to any disclaimer, the term of this patent is extended or adjusted under 35 U.S.C. 154(b) by 344 days.

(21) Appl. No.: 11/920,230

(22) PCT Filed: May 12, 2006

(86) PCT No.: PCT/US2006/018504

§ 371 (c)(1), (2), (4) Date: Jan. 26, 2009

(87) PCT Pub. No.: WO2006/138004

PCT Pub. Date: Dec. 28, 2006

(65) Prior Publication Data

US 2011/0158977 A1 Jun. 30, 2011

Related U.S. Application Data

(60) Provisional application No. 60/680,725, filed on May 12, 2005.

(51) Int. Cl.

*C07K 14/295* (2006.01)
*A61K 38/04* (2006.01)
*A61K 39/118* (2006.01)

(52) U.S. Cl. .................. 530/350; 424/184.1; 424/190.1; 424/263.1; 530/300; 530/324; 530/325; 530/326; 530/327; 530/328; 530/329

(58) Field of Classification Search ........................ None
See application file for complete search history.

(56) References Cited

U.S. PATENT DOCUMENTS

| | | | | |
|---|---|---|---|---|
| 7,462,357 | B2 * | 12/2008 | Bhatia et al. | 424/263.1 |
| 2002/0061848 | A1 * | 5/2002 | Bhatia et al. | 514/12 |
| 2004/0234536 | A1 * | 11/2004 | Bhatia et al. | 424/184.1 |

FOREIGN PATENT DOCUMENTS

| | | | |
|---|---|---|---|
| WO | 99/28475 | A2 | 6/1999 |
| WO | WO0208267 | A2 * | 1/2002 |
| WO | 2005/002619 | A2 | 1/2005 |
| WO | WO2005002619 | A2 * | 1/2005 |
| WO | 2006/045308 | A2 | 5/2006 |
| WO | 2006/104890 | A | 10/2006 |

OTHER PUBLICATIONS

Carlson JH et al., "Low calcium response protein E" Nov. 8, 2005, EBI Database accession No. Q3KMT2.

Carlson John H et al., "Comparative genomic analysis of *Chlamydia trachomatis* oculotropic and genitotropic strains." Infection and Immunity Oct. 2005, vol. 73, No. 10, Oct. 2005, pp. 6407-6418.

Griffais R., "*Chlamydia trachomatis* secreted protein" EBI Database accession No. AAY37124, 1999.

Stephen RS et al., "Low calcium response E." Nov. 1, 1998, EBI Database accession No. 084091.

Stephen R S et al., "Genome Sequence of an Obligate Intracellular Pathogen of Humans: *Chlamydia trachomatis*", Science, vol. 282, Oct. 23, 1998, pp. 754-759.

* cited by examiner

*Primary Examiner* — Padma Baskar

(74) *Attorney, Agent, or Firm* — Banner & Witcoff, Ltd.

(57) ABSTRACT

The present invention provides variant LcrE sequences and/or combinations of variant LcrE sequences across the *Chlamydia trachomatis* serovars. Such changes in LcrE genotypes across the *Chlamydia trachomatis* serovars are likely to correspond with changes in LcrE phenotypes, in particular, with changes in immunogenicity. The present invention also provides peptides surrounding or associated with the amino acid substitutions, in particular, peptides surrounding or associated with high frequency mutated amino acid positions or hypervariable regions, which are likely to be B and/or T cell epitopic regions capable of eliciting *Chlamydia* specific cell mediated immune responses. The variant LcrE sequences and/or combinations of the variant LcrE sequences and/or epitope regions associated with the variant LcrE sequences are useful as immunogens and/or in the preparation of immunogenic compositions for preventing and/or treating and/or, diagnosing *Chlamydia* infections.

24 Claims, 11 Drawing Sheets

FIG. 1A

Amino acid sequence of LcrE alleles found in different clinical isolates of *C. trachomatis*. Sequences are compared to the reference sequence as reported in the fully sequenced genome of the serovar-D strain UW-3/Cx. Amino acid changes are therefore intended as compared to the reference serovar D sequence, arbitrarily identified as allele-1.

Genome: GO/86 serD - 4 aa changes: allele-2 = SEQ ID No 13
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPNEILDALTSKFSDPTIKDLALDYLI
QTAPSDGKLKSALIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*

Genome Cev-1, serJ - 4 aa changes: allele-3 = SEQ ID No 8
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIIGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*

Genome Cev2, serG - no changes: allele-1 (= ATCC-G) = SEQ ID No 9
MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSTLIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

Genome Cev4, serH - no changes: allele-1 = SEQ ID No 10
MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSTLIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

FIG. 1B

Genome Cev5, serJ - 3 aa changes: allele-4 (= ATCC-J) = SEQ ID No 11
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*

Genome Cev8 - 8 aa changes: allele-5 (= ATCC-E) = SEQ ID No 12
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPEEILDALTSKFSDPTIKDLALDYLI
QTAPSDRKLKSALIQAKHQLMSQNPQAIVGGRNVLLASETFASRANTSPS
SLRSLYLQVTSSPSNCDNLRQMLASYLPSEKTAVMEFLVNGMVADLKSEG
PSIPPAKLQVYMTELSNLQALHSVDSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

Genome ATCC-E - 8 aa changes: allele-5 = SEQ ID No 1
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPEEILDALTSKFSDPTIKDLALDYLI
QTAPSDRKLKSALIQAKHQLMSQNPQAIVGGRNVLLASETFASRANTSPS
SLRSLYLQVTSSPSNCDNLRQMLASYLPSEKTAVMEFLVNGMVADLKSEG
PSIPPAKLQVYMTELSNLQALHSVDSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

Genome ATCC-F - no changes: allele-1 = SEQ ID No 2
MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSTLIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

FIG. 1C

Genome ATCC-G - no changes: allele-1 = SEQ ID No 3

MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSTLIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

Genome ATCC-H - 3 aa changes: allele-4 = SEQ ID No 4

MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*

Genome ATCC-I - no changes: allele-1 = SEQ ID No 5

MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSTLIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

Genome ATCC-J - 3 aa changes: allele-4 = SEQ ID No 6

MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*

Genome ATCC-K - no changes: allele-1 = SEQ ID No 7

MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSTLIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

FIG. 1D

REFERENCE SEQUENCE: LcrE from Serovar-D UW-3/Cx strain, showing all amino acid change positions (bold, underlined) detected in this study
SEQ ID No 28

MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSTLIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

| | | |
|---|---|---|
| | M T A S G G A G G L G S T Q T V D V A R A Q A A A A T Q D A | Majority |
| | 10 20 30 | |
| 1 | M T A S G G A G G L G S T Q T V D V A R A Q A A A A T Q D A | LcrE ref pro |
| 1 | M T A S G G A G G L G S T Q T V D V A R A Q A A A A T Q D A | CT089_atccE.pep |
| 1 | M T A S G G A G G L G S T Q T V D V A R A Q A A A A T Q D A | CT089_atccF.pep |
| 1 | M T A S G G A G G L G S T Q T V D V A R A Q A A A A T Q D A | CT089_atccG.pep |
| 1 | M T A S G G A G G L G S T Q T V D V A R A Q A A A A T Q D A | CT089_atccH.pep |
| 1 | M T A S G G A G G L G S T Q T V D V A R A Q A A A A T Q D A | CT089_atccI.pep |
| 1 | M T A S G G A G G L G S T Q T V D V A R A Q A A A A T Q D A | CT089_atccJ.pep |
| 1 | M T A S G G A G G L G S T Q T V D V A R A Q A A A A T Q D A | CT089_atccK.pep |
| 1 | M T A S G G A G G L G S T Q T V D V A R A Q A A A A T Q D A | CT089_Cev1.pep |
| 1 | M T A S G G A G G L G S T Q T V D V A R A Q A A A A T Q D A | CT089_Cev2.pep |
| 1 | M T A S G G A G G L G S T Q T V D V A R A Q A A A A T Q D A | CT089_Cev4.pep |
| 1 | M T A S G G A G G L G S T Q T V D V A R A Q A A A A T Q D A | CT089_Cev5.pep |
| 1 | M T A S G G A G G L G S T Q T V D V A R A Q A A A A T Q D A | CT089_Cev8.pep |
| 1 | M T A S G G A G G L G S T Q T V D V A R A Q A A A A T Q D A | CT089_GO86.pep |

| | | |
|---|---|---|
| | Q E V I G S Q E A S E A S M L K G C E D L I N P A A A T R I | Majority |
| | 40 50 60 | |
| 31 | Q E V I G S Q E A S E A S M L K G C E D L I N P A A A T R I | LcrE ref pro |
| 31 | Q E V I G S Q E A S E A S M L K G C E D L I N P A A A T R I | CT089_atccE.pep |
| 31 | Q E V I G S Q E A S E A S M L K G C E D L I N P A A A T R I | CT089_atccF.pep |
| 31 | Q E V I G S Q E A S E A S M L K G C E D L I N P A A A T R I | CT089_atccG.pep |
| 31 | Q E V I G S Q E A S E A S M L K G C E D L I N P A A A T R I | CT089_atccH.pep |
| 31 | Q E V I G S Q E A S E A S M L K G C E D L I N P A A A T R I | CT089_atccI.pep |
| 31 | Q E V I G S Q E A S E A S M L K G C E D L I N P A A A T R I | CT089_atccJ.pep |
| 31 | Q E V I G S Q E A S E A S M L K G C E D L I N P A A A T R I | CT089_atccK.pep |
| 31 | Q E V I G S Q E A S E A S M L K G C E D L I N P A A A T R I | CT089_Cev1.pep |
| 31 | Q E V I G S Q E A S E A S M L K G C E D L I N P A A A T R I | CT089_Cev2.pep |
| 31 | Q E V I G S Q E A S E A S M L K G C E D L I N P A A A T R I | CT089_Cev4.pep |
| 31 | Q E V I G S Q E A S E A S M L K G C E D L I N P A A A T R I | CT089_Cev5.pep |
| 31 | Q E V I G S Q E A S E A S M L K G C E D L I N P A A A T R I | CT089_Cev8.pep |
| 31 | Q E V I G S Q E A S E A S M L K G C E D L I N P A A A T R I | CT089_GO86.pep |

| | | |
|---|---|---|
| | K K K G E K F E S L E A R R K P T A D K A E K K S E S T E E | Majority |
| | 70 80 90 | |
| 61 | K K K G E K F E S L E A R R K P T A D K A E K K S E S T E E | LcrE ref pro |
| 61 | K K K [illegible] E K F E S L E A R R K P T A D K A E K K S E S T E E | CT089_atccE.pep |
| 61 | K K K G E K F E S L E A R R K P T A D K A E K K S E S T E E | CT089_atccF.pep |
| 61 | K K K G E K F E S L E A R R K P T A D K A E K K S E S T E E | CT089_atccG.pep |
| 61 | K K K [illegible] E K F E S L E A R R K P T A D K A E K K S E S T E E | CT089_atccH.pep |
| 61 | K K K G E K F E S L E A R R K P T A D K A E K K S E S T E E | CT089_atccI.pep |
| 61 | K K K [illegible] E K F E S L E A R R K P T A D K A E K K S E S T E E | CT089_atccJ.pep |
| 61 | K K K G E K F E S L E A R R K P T A D K A E K K S E S T E E | CT089_atccK.pep |
| 61 | K K K [illegible] E K F E S L E A R R K P T A D K A E K K S E S T E E | CT089_Cev1.pep |
| 61 | K K K G E K F E S L E A R R K P T A D K A E K K S E S T E E | CT089_Cev2.pep |
| 61 | K K K G E K F E S L E A R R K P T A D K A E K K S E S T E E | CT089_Cev4.pep |
| 61 | K K K [illegible] E K F E S L E A R R K P T A D K A E K K S E S T E E | CT089_Cev5.pep |
| 61 | K K K [illegible] E K F E S L E A R R K P T A D K A E K K S E S T E E | CT089_Cev8.pep |
| 61 | K K K [illegible] E K F E S L E A R R K P T A D K A E K K S E S T E E | CT089_GO86.pep |

FIG. 2A

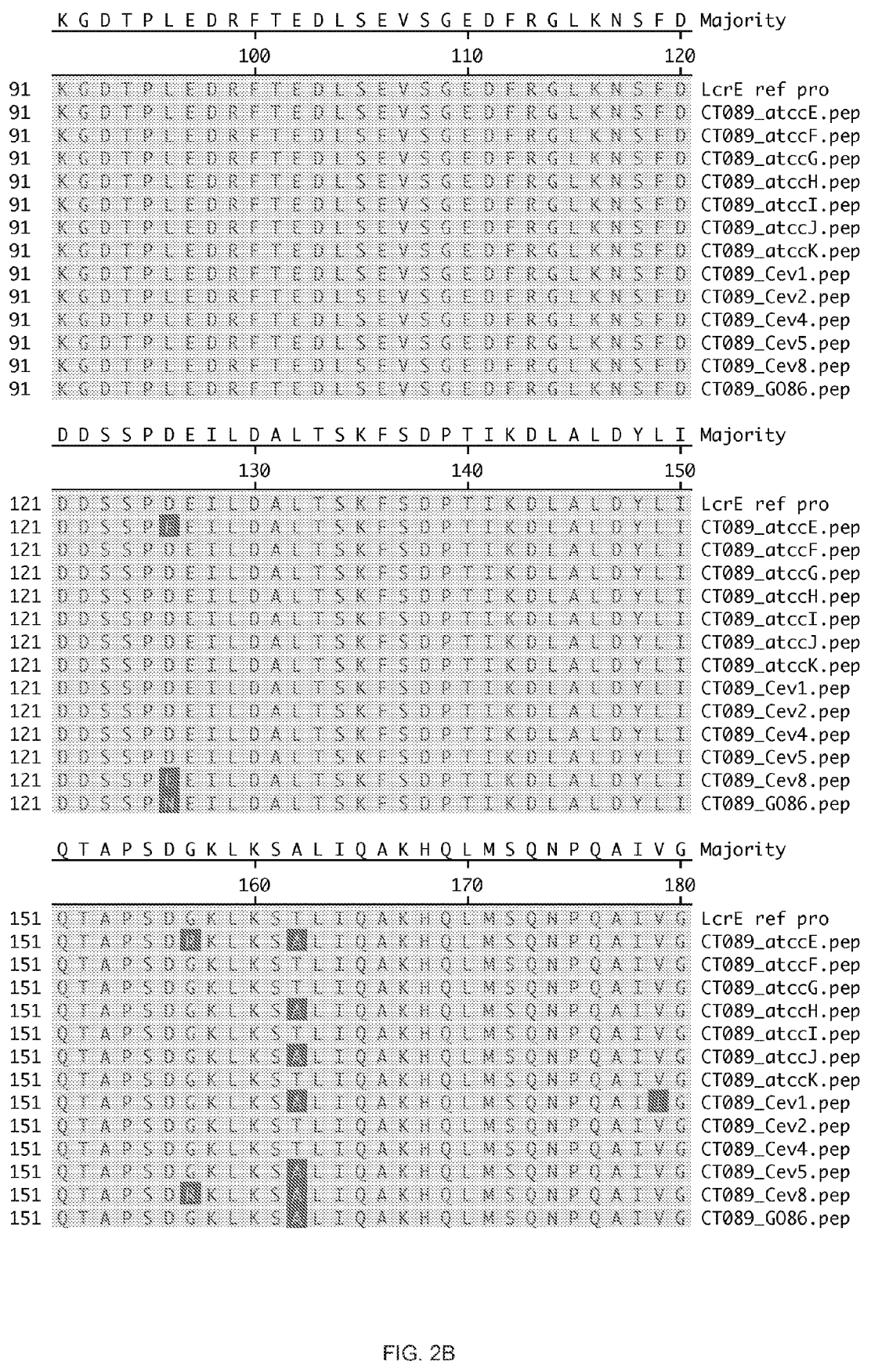

```
      K G D T P L E D R F T E D L S E V S G E D F R G L K N S F D  Majority
                          100                 110                 120
 91   K G D T P L E D R F T E D L S E V S G E D F R G L K N S F D  LcrE ref pro
 91   K G D T P L E D R F T E D L S E V S G E D F R G L K N S F D  CT089_atccE.pep
 91   K G D T P L E D R F T E D L S E V S G E D F R G L K N S F D  CT089_atccF.pep
 91   K G D T P L E D R F T E D L S E V S G E D F R G L K N S F D  CT089_atccG.pep
 91   K G D T P L E D R F T E D L S E V S G E D F R G L K N S F D  CT089_atccH.pep
 91   K G D T P L E D R F T E D L S E V S G E D F R G L K N S F D  CT089_atccI.pep
 91   K G D T P L E D R F T E D L S E V S G E D F R G L K N S F D  CT089_atccJ.pep
 91   K G D T P L E D R F T E D L S E V S G E D F R G L K N S F D  CT089_atccK.pep
 91   K G D T P L E D R F T E D L S E V S G E D F R G L K N S F D  CT089_Cev1.pep
 91   K G D T P L E D R F T E D L S E V S G E D F R G L K N S F D  CT089_Cev2.pep
 91   K G D T P L E D R F T E D L S E V S G E D F R G L K N S F D  CT089_Cev4.pep
 91   K G D T P L E D R F T E D L S E V S G E D F R G L K N S F D  CT089_Cev5.pep
 91   K G D T P L E D R F T E D L S E V S G E D F R G L K N S F D  CT089_Cev8.pep
 91   K G D T P L E D R F T E D L S E V S G E D F R G L K N S F D  CT089_GO86.pep

      D D S S P D E I L D A L T S K F S D P T I K D L A L D Y L I  Majority
                          130                 140                 150
121   D D S S P D E I L D A L T S K F S D P T I K D L A L D Y L I  LcrE ref pro
121   D D S S P [illegible] E I L D A L T S K F S D P T I K D L A L D Y L I  CT089_atccE.pep
121   D D S S P D E I L D A L T S K F S D P T I K D L A L D Y L I  CT089_atccF.pep
121   D D S S P D E I L D A L T S K F S D P T I K D L A L D Y L I  CT089_atccG.pep
121   D D S S P D E I L D A L T S K F S D P T I K D L A L D Y L I  CT089_atccH.pep
121   D D S S P D E I L D A L T S K F S D P T I K D L A L D Y L I  CT089_atccI.pep
121   D D S S P D E I L D A L T S K F S D P T I K D L A L D Y L I  CT089_atccJ.pep
121   D D S S P D E I L D A L T S K F S D P T I K D L A L D Y L I  CT089_atccK.pep
121   D D S S P D E I L D A L T S K F S D P T I K D L A L D Y L I  CT089_Cev1.pep
121   D D S S P D E I L D A L T S K F S D P T I K D L A L D Y L I  CT089_Cev2.pep
121   D D S S P D E I L D A L T S K F S D P T I K D L A L D Y L I  CT089_Cev4.pep
121   D D S S P D E I L D A L T S K F S D P T I K D L A L D Y L I  CT089_Cev5.pep
121   D D S S P [illegible] E I L D A L T S K F S D P T I K D L A L D Y L I  CT089_Cev8.pep
121   D D S S P [illegible] E I L D A L T S K F S D P T I K D L A L D Y L I  CT089_GO86.pep

      Q T A P S D G K L K S A L I Q A K H Q L M S Q N P Q A I V G  Majority
                          160                 170                 180
151   Q T A P S D G K L K S T L I Q A K H Q L M S Q N P Q A I V G  LcrE ref pro
151   Q T A P S D [illegible] K L K S [illegible] L I Q A K H Q L M S Q N P Q A I V G  CT089_atccE.pep
151   Q T A P S D G K L K S T L I Q A K H Q L M S Q N P Q A I V G  CT089_atccF.pep
151   Q T A P S D G K L K S T L I Q A K H Q L M S Q N P Q A I V G  CT089_atccG.pep
151   Q T A P S D G K L K S [illegible] L I Q A K H Q L M S Q N P Q A I V G  CT089_atccH.pep
151   Q T A P S D G K L K S T L I Q A K H Q L M S Q N P Q A I V G  CT089_atccI.pep
151   Q T A P S D G K L K S [illegible] L I Q A K H Q L M S Q N P Q A I V G  CT089_atccJ.pep
151   Q T A P S D G K L K S T L I Q A K H Q L M S Q N P Q A I V G  CT089_atccK.pep
151   Q T A P S D G K L K S [illegible] L I Q A K H Q L M S Q N P Q A I [illegible] G  CT089_Cev1.pep
151   Q T A P S D G K L K S T L I Q A K H Q L M S Q N P Q A I V G  CT089_Cev2.pep
151   Q T A P S D G K L K S T L I Q A K H Q L M S Q N P Q A I V G  CT089_Cev4.pep
151   Q T A P S D G K L K S [illegible] L I Q A K H Q L M S Q N P Q A I V G  CT089_Cev5.pep
151   Q T A P S D [illegible] K L K S [illegible] L I Q A K H Q L M S Q N P Q A I V G  CT089_Cev8.pep
151   Q T A P S D G K L K S [illegible] L I Q A K H Q L M S Q N P Q A I V G  CT089_GO86.pep
```

FIG. 2B

```
    G R N V L L A S E T F A S R A N T S P S S L R S L Y F Q V T Majority
                      190                           200                           210
181 G R N V L L A S E T F A S R A N T S P S S L R S L Y F Q V T LcrE ref pro
181 G R N V L L A S E T F A S R A N T S P S S L R S L Y [illegible] Q V T CT089_atccE.pep
181 G R N V L L A S E T F A S R A N T S P S S L R S L Y F Q V T CT089_atccF.pep
181 G R N V L L A S E T F A S R A N T S P S S L R S L Y F Q V T CT089_atccG.pep
181 G R N V L L A S E T F A S R A N T S P S S L R S L Y F Q V T CT089_atccH.pep
181 G R N V L L A S E T F A S R A N T S P S S L R S L Y F Q V T CT089_atccI.pep
181 G R N V L L A S E T F A S R A N T S P S S L R S L Y F Q V T CT089_atccJ.pep
181 G R N V L L A S E T F A S R A N T S P S S L R S L Y F Q V T CT089_atccK.pep
181 G R N V L L A S E T F A S R A N T S P S S L R S L Y F Q V T CT089_Cev1.pep
181 G R N V L L A S E T F A S R A N T S P S S L R S L Y F Q V T CT089_Cev2.pep
181 G R N V L L A S E T F A S R A N T S P S S L R S L Y F Q V T CT089_Cev4.pep
181 G R N V L L A S E T F A S R A N T S P S S L R S L Y F Q V T CT089_Cev5.pep
181 G R N V L L A S E T F A S R A N T S P S S L R S L Y [illegible] Q V T CT089_Cev8.pep
181 G R N V L L A S E T F A S R A N T S P S S L R S L Y F Q V T CT089_GO86.pep
```

```
    S S P S N C A N L H Q M L A S Y L P S E K T A V M E F L V N Majority
                      220                           230                           240
211 S S P S N C A N L H Q M L A S Y L P S E K T A V M E F L V N LcrE ref pro
211 S S P S N C [illegible] N L [illegible] Q M L A S Y L P S E K T A V M E F L V N CT089_atccE.pep
211 S S P S N C A N L H Q M L A S Y L P S E K T A V M E F L V N CT089_atccF.pep
211 S S P S N C A N L H Q M L A S Y L P S E K T A V M E F L V N CT089_atccG.pep
211 S S P S N C A N L H Q M L A S Y L P S E K T A V M E F L V N CT089_atccH.pep
211 S S P S N C A N L H Q M L A S Y L P S E K T A V M E F L V N CT089_atccI.pep
211 S S P S N C A N L H Q M L A S Y L P S E K T A V M E F L V N CT089_atccJ.pep
211 S S P S N C A N L H Q M L A S Y L P S E K T A V M E F L V N CT089_atccK.pep
211 S S P S N C A N L H Q M L A S Y L P S E K T A V M E F L V N CT089_Cev1.pep
211 S S P S N C A N L H Q M L A S Y L P S E K T A V M E F L V N CT089_Cev2.pep
211 S S P S N C A N L H Q M L A S Y L P S E K T A V M E F L V N CT089_Cev4.pep
211 S S P S N C A N L H Q M L A S Y L P S E K T A V M E F L V N CT089_Cev5.pep
211 S S P S N C [illegible] N L [illegible] Q M L A S Y L P S E K T A V M E F L V N CT089_Cev8.pep
211 S S P S N C A N L H Q M L A S Y L P S E K T A V M E F L V N CT089_GO86.pep
```

```
    G M V A D L K S E G P S I P P A K L Q V Y M T E L S N L Q A Majority
                      250                           260                           270
241 G M V A D L K S E G P S I P P A K L Q V Y M T E L S N L Q A LcrE ref pro
241 G M V A D L K S E G P S I P P A K L Q V Y M T E L S N L Q A CT089_atccE.pep
241 G M V A D L K S E G P S I P P A K L Q V Y M T E L S N L Q A CT089_atccF.pep
241 G M V A D L K S E G P S I P P A K L Q V Y M T E L S N L Q A CT089_atccG.pep
241 G M V A D L K S E G P S I P P A K L Q V Y M T E L S N L Q A CT089_atccH.pep
241 G M V A D L K S E G P S I P P A K L Q V Y M T E L S N L Q A CT089_atccI.pep
241 G M V A D L K S E G P S I P P A K L Q V Y M T E L S N L Q A CT089_atccJ.pep
241 G M V A D L K S E G P S I P P A K L Q V Y M T E L S N L Q A CT089_atccK.pep
241 G M V A D L K S E G P S I P P A K L Q V Y M T E L S N L Q A CT089_Cev1.pep
241 G M V A D L K S E G P S I P P A K L Q V Y M T E L S N L Q A CT089_Cev2.pep
241 G M V A D L K S E G P S I P P A K L Q V Y M T E L S N L Q A CT089_Cev4.pep
241 G M V A D L K S E G P S I P P A K L Q V Y M T E L S N L Q A CT089_Cev5.pep
241 G M V A D L K S E G P S I P P A K L Q V Y M T E L S N L Q A CT089_Cev8.pep
241 G M V A D L K S E G P S I P P A K L Q V Y M T E L S N L Q A CT089_GO86.pep
```

FIG. 2C

```
    L H S V N S F F D R N I G N L E N S L K H E G H A P I P S L  Majority
                      280                 290                 300
271 L H S V N S F F D R N I G N L E N S L K H E G H A P I P S L  LcrE ref pro
271 L H S V [illegible] S F F D R N I G N L E N S L K H E G H A P I P S L  CT089_atccE.pep
271 L H S V N S F F D R N I G N L E N S L K H E G H A P I P S L  CT089_atccF.pep
271 L H S V N S F F D R N I G N L E N S L K H E G H A P I P S L  CT089_atccG.pep
271 L H S V N S F F D R N I G N L E N S L K H E G H A P I P S L  CT089_atccH.pep
271 L H S V N S F F D R N I G N L E N S L K H E G H A P I P S L  CT089_atccI.pep
271 L H S V N S F F D R N I G N L E N S L K H E G H A P I P S L  CT089_atccJ.pep
271 L H S V N S F F D R N I G N L E N S L K H E G H A P I P S L  CT089_atccK.pep
271 L H S V N S F F D R N I G N L E N S L K H E G H A P I P S L  CT089_Cev1.pep
271 L H S V N S F F D R N I G N L E N S L K H E G H A P I P S L  CT089_Cev2.pep
271 L H S V N S F F D R N I G N L E N S L K H E G H A P I P S L  CT089_Cev4.pep
271 L H S V N S F F D R N I G N L E N S L K H E G H A P I P S L  CT089_Cev5.pep
271 L H S V [illegible] S F F D R N I G N L E N S L K H E G H A P I P S L  CT089_Cev8.pep
271 L H S V N S F F D R N I G N L E N S L K H E G H A P I P S L  CT089_GO86.pep

    T T G N L T K T F L Q L V E D K F P S S S K A Q K A L N E L  Majority
                      310                 320                 330
301 T T G N L T K T F L Q L V E D K F P S S S K A Q K A L N E L  LcrE ref pro
301 T T G N L T K T F L Q L V E D K F P S S S K A Q K A L N E L  CT089_atccE.pep
301 T T G N L T K T F L Q L V E D K F P S S S K A Q K A L N E L  CT089_atccF.pep
301 T T G N L T K T F L Q L V E D K F P S S S K A Q K A L N E L  CT089_atccG.pep
301 T T G N L T K T F L Q L V E D K F P S S S K A Q K A L N E L  CT089_atccH.pep
301 T T G N L T K T F L Q L V E D K F P S S S K A Q K A L N E L  CT089_atccI.pep
301 T T G N L T K T F L Q L V E D K F P S S S K A Q K A L N E L  CT089_atccJ.pep
301 T T G N L T K T F L Q L V E D K F P S S S K A Q K A L N E L  CT089_atccK.pep
301 T T G N L T K T F L Q L V E D K F P S S S K A Q K A L N E L  CT089_Cev1.pep
301 T T G N L T K T F L Q L V E D K F P S S S K A Q K A L N E L  CT089_Cev2.pep
301 T T G N L T K T F L Q L V E D K F P S S S K A Q K A L N E L  CT089_Cev4.pep
301 T T G N L T K T F L Q L V E D K F P S S S K A Q K A L N E L  CT089_Cev5.pep
301 T T G N L T K T F L Q L V E D K F P S S S K A Q K A L N E L  CT089_Cev8.pep
301 T T G N L T K T F L Q L V E D K F P S S S K A Q K A L N E L  CT089_GO86.pep

    V G P D T G P Q T E V L N L F F R A L N G C S P R I F S G A  Majority
                      340                 350                 360
331 V G P D T G P Q T E V L N L F F R A L N G C S P R I F S G A  LcrE ref pro
331 V G P D T G P Q T E V L N L F F R A L N G C S P R I F S G A  CT089_atccE.pep
331 V G P D T G P Q T E V L N L F F R A L N G C S P R I F S G A  CT089_atccF.pep
331 V G P D T G P Q T E V L N L F F R A L N G C S P R I F S G A  CT089_atccG.pep
331 V G P D T G P Q T E V L N L F F R A L N G C S P R I F S G A  CT089_atccH.pep
331 V G P D T G P Q T E V L N L F F R A L N G C S P R I F S G A  CT089_atccI.pep
331 V G P D T G P Q T E V L N L F F R A L N G C S P R I F S G A  CT089_atccJ.pep
331 V G P D T G P Q T E V L N L F F R A L N G C S P R I F S G A  CT089_atccK.pep
331 V G P D T G P Q T E V L N L F F R A L N G C S P R I F S G A  CT089_Cev1.pep
331 V G P D T G P Q T E V L N L F F R A L N G C S P R I F S G A  CT089_Cev2.pep
331 V G P D T G P Q T E V L N L F F R A L N G C S P R I F S G A  CT089_Cev4.pep
331 V G P D T G P Q T E V L N L F F R A L N G C S P R I F S G A  CT089_Cev5.pep
331 V G P D T G P Q T E V L N L F F R A L N G C S P R I F S G A  CT089_Cev8.pep
331 V G P D T G P Q T E V L N L F F R A L N G C S P R I F S G A  CT089_GO86.pep
```

FIG. 2D

```
     E K K Q Q L A S V I T N T L D A I N A D N E D Y P K P G D F  Majority
                        370                 380                390
361  E K K Q Q L A S V I T N T L D A I N A D N E D Y P K P G D F  LcrE ref pro
361  E K K Q Q L A S V I T N T L D A I N A D N E D Y P K P G D F  CT089_atccE.pep
361  E K K Q Q L A S V I T N T L D A I N A D N E D Y P K P G D F  CT089_atccF.pep
361  E K K Q Q L A S V I T N T L D A I N A D N E D Y P K P G D F  CT089_atccG.pep
361  E K K Q Q L A S V I T N T L D A I N A D N E D Y P K P G D F  CT089_atccH.pep
361  E K K Q Q L A S V I T N T L D A I N A D N E D Y P K P G D F  CT089_atccI.pep
361  E K K Q Q L A S V I T N T L D A I N A D N E D Y P K P G D F  CT089_atccJ.pep
361  E K K Q Q L A S V I T N T L D A I N A D N E D Y P K P G D F  CT089_atccK.pep
361  E K K Q Q L A S V I T N T L D A I N A D N E D Y P K P G D F  CT089_Cev1.pep
361  E K K Q Q L A S V I T N T L D A I N A D N E D Y P K P G D F  CT089_Cev2.pep
361  E K K Q Q L A S V I T N T L D A I N A D N E D Y P K P G D F  CT089_Cev4.pep
361  E K K Q Q L A S V I T N T L D A I N A D N E D Y P K P G D F  CT089_Cev5.pep
361  E K K Q Q L A S V I T N T L D A I N A D N E D Y P K P G D F  CT089_Cev8.pep
361  E K K Q Q L A S V I T N T L D A I N A D N E D Y P K P G D F  CT089_G086.pep

     P R S S F S S T P P H A P V P Q S E I P T S P T S T Q P P S  Majority
                        400                 410                420
391  P R S S F S S T P P H A P V P Q S E I P T S P T S T Q P P S  LcrE ref pro
391  P R S S F S S T P P H A P V P Q S E I P T S P T S T Q P P S  CT089_atccE.pep
391  P R S S F S S T P P H A P V P Q S E I P T S P T S T Q P P S  CT089_atccF.pep
391  P R S S F S S T P P H A P V P Q S E I P T S P T S T Q P P S  CT089_atccG.pep
391  P R S S F S S T P P H A P V P Q S E I P T S P T S T Q P P [illegible]  CT089_atccH.pep
391  P R S S F S S T P P H A P V P Q S E I P T S P T S T Q P P S  CT089_atccI.pep
391  P R S S F S S T P P H A P V P Q S E I P T S P T S T Q P P [illegible]  CT089_atccJ.pep
391  P R S S F S S T P P H A P V P Q S E I P T S P T S T Q P P S  CT089_atccK.pep
391  P R S S F S S T P P H A P V P Q S E I P T S P T S T Q P P [illegible]  CT089_Cev1.pep
391  P R S S F S S T P P H A P V P Q S E I P T S P T S T Q P P S  CT089_Cev2.pep
391  P R S S F S S T P P H A P V P Q S E I P T S P T S T Q P P S  CT089_Cev4.pep
391  P R S S F S S T P P H A P V P Q S E I P T S P T S T Q P P [illegible]  CT089_Cev5.pep
391  P R S S F S S T P P H A P V P Q S E I P T S P T S T Q P P S  CT089_Cev8.pep
391  P R S S F S S T P P H A P V P Q S E I P T S P T S T Q P P [illegible]  CT089_G086.pep

     P -                                                          Majority

421  P                                                            LcrE ref pro
421  P .                                                          CT089_atccE.pep
421  P .                                                          CT089_atccF.pep
421  P .                                                          CT089_atccG.pep
421  P .                                                          CT089_atccH.pep
421  P .                                                          CT089_atccI.pep
421  P .                                                          CT089_atccJ.pep
421  P .                                                          CT089_atccK.pep
421  P .                                                          CT089_Cev1.pep
421  P .                                                          CT089_Cev2.pep
421  P .                                                          CT089_Cev4.pep
421  P .                                                          CT089_Cev5.pep
421  P .                                                          CT089_Cev8.pep
421  P .                                                          CT089_G086.pep
```

Decoration 'Decoration #1': Box residues that differ from LcrE ref pro.

FIG. 2E

Decoration 'Decoration #2': Shade (with solid deep red) residues that differ from LcrE ref pro.

Decoration 'Decoration #3': Shade (with solid bright yellow) residues that match LcrE ref pro exactly.

FIG. 2F

Allelic variation of 6 genes in 14 CT clinical isolates comprising 8 different serovars

| Gene/ genome | Ref Genome | GO/86 | C8 | Atcc-E | Atcc-F | C2 | Atcc-G | C4 | Atcc-H | Atcc-I | C1 | C5 | Atcc.J | Atcc-K | |
|---|---|---|---|---|---|---|---|---|---|---|---|---|---|---|---|
| Serovar | D | D | E | E | F | G | G | H | H | I | J | J | J | K | |
| CT045 | 1 | 2 | 3 | 3 | 2 | 1 | 1 | 1 | 1 | 1 | 1 | 1 | 1 | 1 | 3 alleles, Max. 4 aa substitution points in 499 aa |
| CT089 | 1 | 2 | 5 | 5 | 1 | 1 | 1 | 1 | 4 | 1 | 3 | 4 | 4 | 1 | 5 alleles, Max. 8 aa substitution points in 421 aa |
| CT242 | 1 | 2 | 2 | 2 | 2 | 1 | 1 | 1 | 1 | 1 | 1 | 1 | 1 | 1 | 2 alleles, Max. 1 aa substitution point in 173 aa |
| CT381 | 1 | 2 | 2 | 2 | 1 | 1 | 1 | 1 | 1 | 1 | 1 | 1 | 1 | 1 | 2 alleles, Max. 2 aa substitution points in 257 aa |
| CT396 | 1 | 2 | 2 | 2 | 2 | 1 | 1 | 1 | 1 | 1 | 1 | 1 | 1 | 1 | 2 alleles, Max. 1 aa substitution point in 660 aa |
| CT398 | 1 | 2 | 2 | 2 | 2 | 1 | 1 | 1 | 1 | 1 | 1 | 1 | 1 | 1 | 2 alleles, Max 2 aa substitution points in 254 aa |

FIGURE 3

SEQUENCE LISTING

```
<160> NUMBER OF SEQ ID NOS: 185

<210> SEQ ID NO 1
<211> LENGTH: 421
<212> TYPE: PRT
<213> ORGANISM: Chlamydia trachomatis

<400> SEQUENCE: 1

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45
```

```
Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Glu Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Arg Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Leu Gln
        195                 200                 205

Val Thr Ser Ser Pro Ser Asn Cys Asp Asn Leu Arg Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asp Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420
```

<210> SEQ ID NO 2
<211> LENGTH: 421
<212> TYPE: PRT
<213> ORGANISM: Chlamydia trachomatis

<400> SEQUENCE: 2

```
Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
```

420

<210> SEQ ID NO 3
<211> LENGTH: 421
<212> TYPE: PRT
<213> ORGANISM: Chlamydia trachomatis

<400> SEQUENCE: 3

```
Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
```

```
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 4
<211> LENGTH: 421
<212> TYPE: PRT
<213> ORGANISM: Chlamydia trachomatis

<400> SEQUENCE: 4

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
```

```
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Pro Pro
            420


<210> SEQ ID NO 5
<211> LENGTH: 421
<212> TYPE: PRT
<213> ORGANISM: Chlamydia trachomatis

<400> SEQUENCE: 5

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
```

```
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 6
<211> LENGTH: 421
<212> TYPE: PRT
<213> ORGANISM: Chlamydia trachomatis

<400> SEQUENCE: 6

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
```

```
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Pro Pro
            420


<210> SEQ ID NO 7
<211> LENGTH: 421
<212> TYPE: PRT
<213> ORGANISM: Chlamydia trachomatis

<400> SEQUENCE: 7

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
```

```
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 8
<211> LENGTH: 421
<212> TYPE: PRT
<213> ORGANISM: Chlamydia trachomatis

<400> SEQUENCE: 8

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
```

```
    130                 135                 140

Ala Leu Asp Tyr Leu Ile Gln Thr Ala Pro Ser Asp Gly Lys Leu Lys
145                 150                 155                 160

Ser Ala Leu Ile Gln Ala Lys His Gln Leu Met Ser Gln Asn Pro Gln
                165                 170                 175

Ala Ile Ile Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Pro Pro
            420


<210> SEQ ID NO 9
<211> LENGTH: 421
<212> TYPE: PRT
<213> ORGANISM: Chlamydia trachomatis

<400> SEQUENCE: 9

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
```

-continued

```
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 10
<211> LENGTH: 421
<212> TYPE: PRT
<213> ORGANISM: Chlamydia trachomatis

<400> SEQUENCE: 10

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
```

-continued

```
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 11
<211> LENGTH: 421
<212> TYPE: PRT
<213> ORGANISM: Chlamydia trachomatis
```

<400> SEQUENCE: 11

```
Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415
```

```
Gln Pro Pro Pro Pro
            420


<210> SEQ ID NO 12
<211> LENGTH: 421
<212> TYPE: PRT
<213> ORGANISM: Chlamydia trachomatis

<400> SEQUENCE: 12

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Glu Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Arg Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Leu Gln
        195                 200                 205

Val Thr Ser Ser Pro Ser Asn Cys Asp Asn Leu Arg Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asp Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365
```

```
Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 13
<211> LENGTH: 421
<212> TYPE: PRT
<213> ORGANISM: Chlamydia trachomatis

<400> SEQUENCE: 13

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asn Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320
```

Ser Lys Ala Gln Lys Ala Leu Asn Glu Leu Val Gly Pro Asp Thr Gly
325 330 335

Pro Gln Thr Glu Val Leu Asn Leu Phe Phe Arg Ala Leu Asn Gly Cys
340 345 350

Ser Pro Arg Ile Phe Ser Gly Ala Glu Lys Lys Gln Gln Leu Ala Ser
355 360 365

Val Ile Thr Asn Thr Leu Asp Ala Ile Asn Ala Asp Asn Glu Asp Tyr
370 375 380

Pro Lys Pro Gly Asp Phe Pro Arg Ser Ser Phe Ser Ser Thr Pro Pro
385 390 395 400

His Ala Pro Val Pro Gln Ser Glu Ile Pro Thr Ser Pro Thr Ser Thr
405 410 415

Gln Pro Pro Pro Pro
420

<210> SEQ ID NO 14
<211> LENGTH: 30
<212> TYPE: PRT
<213> ORGANISM: Chlamydia trachomatis

<400> SEQUENCE: 14

Met Thr Ala Ser Gly Gly Ala Gly Gly Leu Gly Ser Thr Gln Thr Val
1 5 10 15

Asp Val Ala Arg Ala Gln Ala Ala Ala Ala Thr Gln Asp Ala
20 25 30

<210> SEQ ID NO 15
<211> LENGTH: 30
<212> TYPE: PRT
<213> ORGANISM: Chlamydia trachomatis

<400> SEQUENCE: 15

Gln Glu Val Ile Gly Ser Gln Glu Ala Ser Glu Ala Ser Met Leu Lys
1 5 10 15

Gly Cys Glu Asp Leu Ile Asn Pro Ala Ala Ala Thr Arg Ile
20 25 30

<210> SEQ ID NO 16
<211> LENGTH: 30
<212> TYPE: PRT
<213> ORGANISM: Chlamydia trachomatis
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Lys Lys Lys Xaa Glu Lys Phe Glu Ser Leu Glu Ala Arg Arg Lys Pro
1 5 10 15

Thr Ala Asp Lys Ala Glu Lys Lys Ser Glu Ser Thr Glu Glu
20 25 30

<210> SEQ ID NO 17
<211> LENGTH: 30
<212> TYPE: PRT
<213> ORGANISM: Chlamydia trachomatis

<400> SEQUENCE: 17

Lys Gly Asp Thr Pro Leu Glu Asp Arg Phe Thr Glu Asp Leu Ser Glu
1 5 10 15

Val Ser Gly Glu Asp Phe Arg Gly Leu Lys Asn Ser Phe Asp
20 25 30

<210> SEQ ID NO 18
<211> LENGTH: 30
<212> TYPE: PRT
<213> ORGANISM: Chlamydia trachomatis

<400> SEQUENCE: 18

Asp Asp Ser Ser Pro Asp Glu Ile Leu Asp Ala Leu Thr Ser Lys Phe
1               5                   10                  15

Ser Asp Pro Thr Ile Lys Asp Leu Ala Leu Asp Tyr Leu Ile
            20                  25                  30

<210> SEQ ID NO 19
<211> LENGTH: 30
<212> TYPE: PRT
<213> ORGANISM: Chlamydia trachomatis
<220> FEATURE:
<221> NAME/KEY: misc_feature
<222> LOCATION: (12)..(12)
<223> OTHER INFORMATION: Xaa can be any naturally occurring amino acid

<400> SEQUENCE: 19

Gln Thr Ala Pro Ser Asp Gly Lys Leu Lys Ser Xaa Leu Ile Gln Ala
1               5                   10                  15

Lys His Gln Leu Met Ser Gln Asn Pro Gln Ala Ile Val Gly
            20                  25                  30

<210> SEQ ID NO 20
<211> LENGTH: 30
<212> TYPE: PRT
<213> ORGANISM: Chlamydia trachomatis

<400> SEQUENCE: 20

Gly Arg Asn Val Leu Leu Ala Ser Glu Thr Phe Ala Ser Arg Ala Asn
1               5                   10                  15

Thr Ser Pro Ser Ser Leu Arg Ser Leu Tyr Phe Gln Val Thr
            20                  25                  30

<210> SEQ ID NO 21
<211> LENGTH: 30
<212> TYPE: PRT
<213> ORGANISM: Chlamydia trachomatis

<400> SEQUENCE: 21

Ser Ser Pro Ser Asn Cys Ala Asn Leu His Gln Met Leu Ala Ser Tyr
1               5                   10                  15

Leu Pro Ser Glu Lys Thr Ala Val Met Glu Phe Leu Val Asn
            20                  25                  30

<210> SEQ ID NO 22
<211> LENGTH: 30
<212> TYPE: PRT
<213> ORGANISM: Chlamydia trachomatis

<400> SEQUENCE: 22

Gly Met Val Ala Asp Leu Lys Ser Glu Gly Pro Ser Ile Pro Pro Ala
1               5                   10                  15

Lys Leu Gln Val Tyr Met Thr Glu Leu Ser Asn Leu Gln Ala
            20                  25                  30

<210> SEQ ID NO 23
<211> LENGTH: 30
<212> TYPE: PRT
<213> ORGANISM: Chlamydia trachomatis

<400> SEQUENCE: 23

Leu His Ser Val Asn Ser Phe Phe Asp Arg Asn Ile Gly Asn Leu Glu
1 5 10 15

Asn Ser Leu Lys His Glu Gly His Ala Pro Ile Pro Ser Leu
20 25 30

<210> SEQ ID NO 24
<211> LENGTH: 30
<212> TYPE: PRT
<213> ORGANISM: Chlamydia trachomatis

<400> SEQUENCE: 24

Thr Thr Gly Asn Leu Thr Lys Thr Phe Leu Gln Leu Val Glu Asp Lys
1 5 10 15

Phe Pro Ser Ser Ser Lys Ala Gln Lys Ala Leu Asn Glu Leu
20 25 30

<210> SEQ ID NO 25
<211> LENGTH: 30
<212> TYPE: PRT
<213> ORGANISM: Chlamydia trachomatis

<400> SEQUENCE: 25

Val Gly Pro Asp Thr Gly Pro Gln Thr Glu Val Leu Asn Leu Phe Phe
1 5 10 15

Arg Ala Leu Asn Gly Cys Ser Pro Arg Ile Phe Ser Gly Ala
20 25 30

<210> SEQ ID NO 26
<211> LENGTH: 30
<212> TYPE: PRT
<213> ORGANISM: Chlamydia trachomatis

<400> SEQUENCE: 26

Glu Lys Lys Gln Gln Leu Ala Ser Val Ile Thr Asn Thr Leu Asp Ala
1 5 10 15

Ile Asn Ala Asp Asn Glu Asp Tyr Pro Lys Pro Gly Asp Phe
20 25 30

<210> SEQ ID NO 27
<211> LENGTH: 30
<212> TYPE: PRT
<213> ORGANISM: Chlamydia trachomatis

<400> SEQUENCE: 27

Pro Arg Ser Ser Phe Ser Ser Thr Pro Pro His Ala Pro Val Pro Gln
1 5 10 15

Ser Glu Ile Pro Thr Ser Pro Thr Ser Thr Gln Pro Pro Ser
20 25 30

<210> SEQ ID NO 28
<211> LENGTH: 421
<212> TYPE: PRT
<213> ORGANISM: Chlamydia trachomatis

<400> SEQUENCE: 28

Met Thr Ala Ser Gly Gly Ala Gly Gly Leu Gly Ser Thr Gln Thr Val
1 5 10 15

Asp Val Ala Arg Ala Gln Ala Ala Ala Ala Thr Gln Asp Ala Gln Glu
20 25 30

Val Ile Gly Ser Gln Glu Ala Ser Glu Ala Ser Met Leu Lys Gly Cys

```
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420
```

<210> SEQ ID NO 29
<211> LENGTH: 13
<212> TYPE: PRT
<213> ORGANISM: Chlamydia trachomatis

<400> SEQUENCE: 29

Gln Thr Val Asp Val Ala Arg Ala Gln Ala Ala Ala Ala
1 5 10

<210> SEQ ID NO 30
<211> LENGTH: 7
<212> TYPE: PRT
<213> ORGANISM: Chlamydia trachomatis

<400> SEQUENCE: 30

Asp Ala Gln Glu Val Ile Gly
1 5

<210> SEQ ID NO 31
<211> LENGTH: 11
<212> TYPE: PRT
<213> ORGANISM: Chlamydia trachomatis

<400> SEQUENCE: 31

Met Leu Lys Gly Cys Glu Asp Leu Ile Asn Pro
1 5 10

<210> SEQ ID NO 32
<211> LENGTH: 10
<212> TYPE: PRT
<213> ORGANISM: Chlamydia trachomatis

<400> SEQUENCE: 32

Pro Asp Glu Ile Leu Asp Ala Leu Thr Ser
1 5 10

<210> SEQ ID NO 33
<211> LENGTH: 13
<212> TYPE: PRT
<213> ORGANISM: Chlamydia trachomatis

<400> SEQUENCE: 33

Thr Ile Lys Asp Leu Ala Leu Asp Tyr Leu Ile Gln Thr
1 5 10

<210> SEQ ID NO 34
<211> LENGTH: 11
<212> TYPE: PRT
<213> ORGANISM: Chlamydia trachomatis

<400> SEQUENCE: 34

Leu Lys Ser Thr Leu Ile Gln Ala Lys His Gln
1 5 10

<210> SEQ ID NO 35
<211> LENGTH: 10
<212> TYPE: PRT
<213> ORGANISM: Chlamydia trachomatis

<400> SEQUENCE: 35

Gly Gly Arg Asn Val Leu Leu Ala Ser Glu
1 5 10

<210> SEQ ID NO 36
<211> LENGTH: 33
<212> TYPE: PRT
<213> ORGANISM: Chlamydia trachomatis

<400> SEQUENCE: 36

Ser Pro Ser Ser Leu Arg Ser Leu Tyr Phe Gln Val Thr Ser Ser Pro

-continued

```
1               5                   10                  15

Ser Asn Cys Ala Asn Leu His Gln Met Leu Ala Ser Tyr Leu Pro Ser
            20                  25                  30

Glu


<210> SEQ ID NO 37
<211> LENGTH: 13
<212> TYPE: PRT
<213> ORGANISM: Chlamydia trachomatis

<400> SEQUENCE: 37

Ala Val Met Glu Phe Leu Val Asn Gly Met Val Ala Asp
1               5                   10


<210> SEQ ID NO 38
<211> LENGTH: 13
<212> TYPE: PRT
<213> ORGANISM: Chlamydia trachomatis

<400> SEQUENCE: 38

Gly Pro Ser Ile Pro Pro Ala Lys Leu Gln Val Tyr Met
1               5                   10


<210> SEQ ID NO 39
<211> LENGTH: 12
<212> TYPE: PRT
<213> ORGANISM: Chlamydia trachomatis

<400> SEQUENCE: 39

Leu Ser Asn Leu Gln Ala Leu His Ser Val Asn Ser
1               5                   10


<210> SEQ ID NO 40
<211> LENGTH: 7
<212> TYPE: PRT
<213> ORGANISM: Chlamydia trachomatis

<400> SEQUENCE: 40

Gly His Ala Pro Ile Pro Ser
1               5


<210> SEQ ID NO 41
<211> LENGTH: 10
<212> TYPE: PRT
<213> ORGANISM: Chlamydia trachomatis

<400> SEQUENCE: 41

Thr Lys Thr Phe Leu Gln Leu Val Glu Asp
1               5                   10


<210> SEQ ID NO 42
<211> LENGTH: 8
<212> TYPE: PRT
<213> ORGANISM: Chlamydia trachomatis

<400> SEQUENCE: 42

Ala Leu Asn Glu Leu Val Gly Pro
1               5


<210> SEQ ID NO 43
<211> LENGTH: 20
<212> TYPE: PRT
<213> ORGANISM: Chlamydia trachomatis

<400> SEQUENCE: 43
```

```
Pro Gln Thr Glu Val Leu Asn Leu Phe Phe Arg Ala Leu Asn Gly Cys
1               5                   10                  15

Ser Pro Arg Ile
            20


<210> SEQ ID NO 44
<211> LENGTH: 10
<212> TYPE: PRT
<213> ORGANISM: Chlamydia trachomatis

<400> SEQUENCE: 44

Lys Lys Gln Gln Leu Ala Ser Val Ile Thr
1               5                   10


<210> SEQ ID NO 45
<211> LENGTH: 15
<212> TYPE: PRT
<213> ORGANISM: Chlamydia trachomatis

<400> SEQUENCE: 45

Phe Ser Ser Thr Pro Pro His Ala Pro Val Pro Gln Ser Glu Ile
1               5                   10                  15


<210> SEQ ID NO 46
<211> LENGTH: 421
<212> TYPE: PRT
<213> ORGANISM: Chlamydia trachomatis

<400> SEQUENCE: 46

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
```

```
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 47
<211> LENGTH: 15
<212> TYPE: PRT
<213> ORGANISM: Chlamydia trachomatis

<400> SEQUENCE: 47

Met Thr Ala Ser Gly Gly Ala Gly Gly Leu Gly Ser Thr Gln Thr
1               5                   10                  15


<210> SEQ ID NO 48
<211> LENGTH: 15
<212> TYPE: PRT
<213> ORGANISM: Chlamydia trachomatis

<400> SEQUENCE: 48

Gly Leu Gly Ser Thr Gln Thr Val Asp Val Ala Arg Ala Gln Ala
1               5                   10                  15


<210> SEQ ID NO 49
<211> LENGTH: 15
<212> TYPE: PRT
<213> ORGANISM: Chlamydia trachomatis

<400> SEQUENCE: 49

Asp Val Ala Arg Ala Gln Ala Ala Ala Ala Thr Gln Asp Ala Gln
1               5                   10                  15


<210> SEQ ID NO 50
<211> LENGTH: 15
<212> TYPE: PRT
<213> ORGANISM: Chlamydia trachomatis

<400> SEQUENCE: 50

Ala Ala Thr Gln Asp Ala Gln Glu Val Ile Gly Ser Gln Glu Ala
```

1 5 10 15

<210> SEQ ID NO 51
<211> LENGTH: 15
<212> TYPE: PRT
<213> ORGANISM: Chlamydia trachomatis

<400> SEQUENCE: 51

Val Ile Gly Ser Gln Glu Ala Ser Glu Ala Ser Met Leu Lys Gly
1 5 10 15

<210> SEQ ID NO 52
<211> LENGTH: 15
<212> TYPE: PRT
<213> ORGANISM: Chlamydia trachomatis

<400> SEQUENCE: 52

Glu Ala Ser Met Leu Lys Gly Cys Glu Asp Leu Ile Asn Pro Ala
1 5 10 15

<210> SEQ ID NO 53
<211> LENGTH: 15
<212> TYPE: PRT
<213> ORGANISM: Chlamydia trachomatis

<400> SEQUENCE: 53

Glu Asp Leu Ile Asn Pro Ala Ala Ala Thr Arg Ile Lys Lys Lys
1 5 10 15

<210> SEQ ID NO 54
<211> LENGTH: 15
<212> TYPE: PRT
<213> ORGANISM: Chlamydia trachomatis

<400> SEQUENCE: 54

Ala Thr Arg Ile Lys Lys Lys Gly Glu Lys Phe Glu Ser Leu Glu
1 5 10 15

<210> SEQ ID NO 55
<211> LENGTH: 15
<212> TYPE: PRT
<213> ORGANISM: Chlamydia trachomatis

<400> SEQUENCE: 55

Glu Lys Phe Glu Ser Leu Glu Ala Arg Arg Lys Pro Thr Ala Asp
1 5 10 15

<210> SEQ ID NO 56
<211> LENGTH: 15
<212> TYPE: PRT
<213> ORGANISM: Chlamydia trachomatis

<400> SEQUENCE: 56

Arg Arg Lys Pro Thr Ala Asp Lys Ala Glu Lys Lys Ser Glu Ser
1 5 10 15

<210> SEQ ID NO 57
<211> LENGTH: 15
<212> TYPE: PRT
<213> ORGANISM: Chlamydia trachomatis

<400> SEQUENCE: 57

Ala Glu Lys Lys Ser Glu Ser Thr Glu Glu Lys Gly Asp Thr Pro
1 5 10 15

<210> SEQ ID NO 58
<211> LENGTH: 15
<212> TYPE: PRT
<213> ORGANISM: Chlamydia trachomatis

<400> SEQUENCE: 58

Glu Glu Lys Gly Asp Thr Pro Leu Glu Asp Arg Phe Thr Glu Asp
1 5 10 15

<210> SEQ ID NO 59
<211> LENGTH: 15
<212> TYPE: PRT
<213> ORGANISM: Chlamydia trachomatis

<400> SEQUENCE: 59

Glu Asp Arg Phe Thr Glu Asp Leu Ser Glu Val Ser Gly Glu Asp
1 5 10 15

<210> SEQ ID NO 60
<211> LENGTH: 15
<212> TYPE: PRT
<213> ORGANISM: Chlamydia trachomatis

<400> SEQUENCE: 60

Ser Glu Val Ser Gly Glu Asp Phe Arg Gly Leu Lys Asn Ser Phe
1 5 10 15

<210> SEQ ID NO 61
<211> LENGTH: 15
<212> TYPE: PRT
<213> ORGANISM: Chlamydia trachomatis

<400> SEQUENCE: 61

Arg Gly Leu Lys Asn Ser Phe Asp Asp Asp Ser Ser Pro Asp Glu
1 5 10 15

<210> SEQ ID NO 62
<211> LENGTH: 15
<212> TYPE: PRT
<213> ORGANISM: Chlamydia trachomatis

<400> SEQUENCE: 62

Asp Asp Ser Ser Pro Asp Glu Ile Leu Asp Ala Leu Thr Ser Lys
1 5 10 15

<210> SEQ ID NO 63
<211> LENGTH: 15
<212> TYPE: PRT
<213> ORGANISM: Chlamydia trachomatis

<400> SEQUENCE: 63

Leu Asp Ala Leu Thr Ser Lys Phe Ser Asp Pro Thr Ile Lys Asp
1 5 10 15

<210> SEQ ID NO 64
<211> LENGTH: 15
<212> TYPE: PRT
<213> ORGANISM: Chlamydia trachomatis

<400> SEQUENCE: 64

Ser Asp Pro Thr Ile Lys Asp Leu Ala Leu Asp Tyr Leu Ile Gln
1 5 10 15

<210> SEQ ID NO 65
<211> LENGTH: 15
<212> TYPE: PRT

<213> ORGANISM: Chlamydia trachomatis

<400> SEQUENCE: 65

Ala Leu Asp Tyr Leu Ile Gln Thr Ala Pro Ser Asp Gly Lys Leu
1 5 10 15

<210> SEQ ID NO 66
<211> LENGTH: 15
<212> TYPE: PRT
<213> ORGANISM: Chlamydia trachomatis

<400> SEQUENCE: 66

Ala Pro Ser Asp Gly Lys Leu Lys Ser Thr Leu Ile Gln Ala Lys
1 5 10 15

<210> SEQ ID NO 67
<211> LENGTH: 15
<212> TYPE: PRT
<213> ORGANISM: Chlamydia trachomatis

<400> SEQUENCE: 67

Ser Thr Leu Ile Gln Ala Lys His Gln Leu Met Ser Gln Asn Pro
1 5 10 15

<210> SEQ ID NO 68
<211> LENGTH: 15
<212> TYPE: PRT
<213> ORGANISM: Chlamydia trachomatis

<400> SEQUENCE: 68

Gln Leu Met Ser Gln Asn Pro Gln Ala Ile Val Gly Gly Arg Asn
1 5 10 15

<210> SEQ ID NO 69
<211> LENGTH: 15
<212> TYPE: PRT
<213> ORGANISM: Chlamydia trachomatis

<400> SEQUENCE: 69

Ala Ile Val Gly Gly Arg Asn Val Leu Leu Ala Ser Glu Thr Phe
1 5 10 15

<210> SEQ ID NO 70
<211> LENGTH: 15
<212> TYPE: PRT
<213> ORGANISM: Chlamydia trachomatis

<400> SEQUENCE: 70

Leu Leu Ala Ser Glu Thr Phe Ala Ser Arg Ala Asn Thr Ser Pro
1 5 10 15

<210> SEQ ID NO 71
<211> LENGTH: 15
<212> TYPE: PRT
<213> ORGANISM: Chlamydia trachomatis

<400> SEQUENCE: 71

Ser Arg Ala Asn Thr Ser Pro Ser Ser Leu Arg Ser Leu Tyr Phe
1 5 10 15

<210> SEQ ID NO 72
<211> LENGTH: 15
<212> TYPE: PRT
<213> ORGANISM: Chlamydia trachomatis

<400> SEQUENCE: 72

Ser Leu Arg Ser Leu Tyr Phe Gln Val Thr Ser Ser Pro Ser Asn
1 5 10 15

<210> SEQ ID NO 73
<211> LENGTH: 15
<212> TYPE: PRT
<213> ORGANISM: Chlamydia trachomatis

<400> SEQUENCE: 73

Val Thr Ser Ser Pro Ser Asn Cys Ala Asn Leu His Gln Met Leu
1 5 10 15

<210> SEQ ID NO 74
<211> LENGTH: 15
<212> TYPE: PRT
<213> ORGANISM: Chlamydia trachomatis

<400> SEQUENCE: 74

Ala Asn Leu His Gln Met Leu Ala Ser Tyr Leu Pro Ser Glu Lys
1 5 10 15

<210> SEQ ID NO 75
<211> LENGTH: 15
<212> TYPE: PRT
<213> ORGANISM: Chlamydia trachomatis

<400> SEQUENCE: 75

Ser Tyr Leu Pro Ser Glu Lys Thr Ala Val Met Glu Phe Leu Val
1 5 10 15

<210> SEQ ID NO 76
<211> LENGTH: 15
<212> TYPE: PRT
<213> ORGANISM: Chlamydia trachomatis

<400> SEQUENCE: 76

Ala Val Met Glu Phe Leu Val Asn Gly Met Val Ala Asp Leu Lys
1 5 10 15

<210> SEQ ID NO 77
<211> LENGTH: 15
<212> TYPE: PRT
<213> ORGANISM: Chlamydia trachomatis

<400> SEQUENCE: 77

Gly Met Val Ala Asp Leu Lys Ser Glu Gly Pro Ser Ile Pro Pro
1 5 10 15

<210> SEQ ID NO 78
<211> LENGTH: 15
<212> TYPE: PRT
<213> ORGANISM: Chlamydia trachomatis

<400> SEQUENCE: 78

Glu Gly Pro Ser Ile Pro Pro Ala Lys Leu Gln Val Tyr Met Thr
1 5 10 15

<210> SEQ ID NO 79
<211> LENGTH: 15
<212> TYPE: PRT
<213> ORGANISM: Chlamydia trachomatis

<400> SEQUENCE: 79

Lys Leu Gln Val Tyr Met Thr Glu Leu Ser Asn Leu Gln Ala Leu
1 5 10 15

<210> SEQ ID NO 80
<211> LENGTH: 15
<212> TYPE: PRT
<213> ORGANISM: Chlamydia trachomatis

<400> SEQUENCE: 80

Leu Ser Asn Leu Gln Ala Leu His Ser Val Asn Ser Phe Phe Asp
1 5 10 15

<210> SEQ ID NO 81
<211> LENGTH: 15
<212> TYPE: PRT
<213> ORGANISM: Chlamydia trachomatis

<400> SEQUENCE: 81

Ser Val Asn Ser Phe Phe Asp Arg Asn Ile Gly Asn Leu Glu Asn
1 5 10 15

<210> SEQ ID NO 82
<211> LENGTH: 15
<212> TYPE: PRT
<213> ORGANISM: Chlamydia trachomatis

<400> SEQUENCE: 82

Asn Ile Gly Asn Leu Glu Asn Ser Leu Lys His Glu Gly His Ala
1 5 10 15

<210> SEQ ID NO 83
<211> LENGTH: 15
<212> TYPE: PRT
<213> ORGANISM: Chlamydia trachomatis

<400> SEQUENCE: 83

Leu Lys His Glu Gly His Ala Pro Ile Pro Ser Leu Thr Thr Gly
1 5 10 15

<210> SEQ ID NO 84
<211> LENGTH: 15
<212> TYPE: PRT
<213> ORGANISM: Chlamydia trachomatis

<400> SEQUENCE: 84

Ile Pro Ser Leu Thr Thr Gly Asn Leu Thr Lys Thr Phe Leu Gln
1 5 10 15

<210> SEQ ID NO 85
<211> LENGTH: 15
<212> TYPE: PRT
<213> ORGANISM: Chlamydia trachomatis

<400> SEQUENCE: 85

Leu Thr Lys Thr Phe Leu Gln Leu Val Glu Asp Lys Phe Pro Ser
1 5 10 15

<210> SEQ ID NO 86
<211> LENGTH: 15
<212> TYPE: PRT
<213> ORGANISM: Chlamydia trachomatis

<400> SEQUENCE: 86

Val Glu Asp Lys Phe Pro Ser Ser Ser Lys Ala Gln Lys Ala Leu
1 5 10 15

<210> SEQ ID NO 87

<211> LENGTH: 15
<212> TYPE: PRT
<213> ORGANISM: Chlamydia trachomatis

<400> SEQUENCE: 87

Ser Lys Ala Gln Lys Ala Leu Asn Glu Leu Val Gly Pro Asp Thr
1 5 10 15

<210> SEQ ID NO 88
<211> LENGTH: 15
<212> TYPE: PRT
<213> ORGANISM: Chlamydia trachomatis

<400> SEQUENCE: 88

Glu Leu Val Gly Pro Asp Thr Gly Pro Gln Thr Glu Val Leu Asn
1 5 10 15

<210> SEQ ID NO 89
<211> LENGTH: 15
<212> TYPE: PRT
<213> ORGANISM: Chlamydia trachomatis

<400> SEQUENCE: 89

Pro Gln Thr Glu Val Leu Asn Leu Phe Phe Arg Ala Leu Asn Gly
1 5 10 15

<210> SEQ ID NO 90
<211> LENGTH: 15
<212> TYPE: PRT
<213> ORGANISM: Chlamydia trachomatis

<400> SEQUENCE: 90

Phe Phe Arg Ala Leu Asn Gly Cys Ser Pro Arg Ile Phe Ser Gly
1 5 10 15

<210> SEQ ID NO 91
<211> LENGTH: 15
<212> TYPE: PRT
<213> ORGANISM: Chlamydia trachomatis

<400> SEQUENCE: 91

Ser Pro Arg Ile Phe Ser Gly Ala Glu Lys Lys Gln Gln Leu Ala
1 5 10 15

<210> SEQ ID NO 92
<211> LENGTH: 15
<212> TYPE: PRT
<213> ORGANISM: Chlamydia trachomatis

<400> SEQUENCE: 92

Glu Lys Lys Gln Gln Leu Ala Ser Val Ile Thr Asn Thr Leu Asp
1 5 10 15

<210> SEQ ID NO 93
<211> LENGTH: 15
<212> TYPE: PRT
<213> ORGANISM: Chlamydia trachomatis

<400> SEQUENCE: 93

Val Ile Thr Asn Thr Leu Asp Ala Ile Asn Ala Asp Asn Glu Asp
1 5 10 15

<210> SEQ ID NO 94
<211> LENGTH: 15
<212> TYPE: PRT
<213> ORGANISM: Chlamydia trachomatis

<400> SEQUENCE: 94

Ile Asn Ala Asp Asn Glu Asp Tyr Pro Lys Pro Gly Asp Phe Pro
1 5 10 15

<210> SEQ ID NO 95
<211> LENGTH: 15
<212> TYPE: PRT
<213> ORGANISM: Chlamydia trachomatis

<400> SEQUENCE: 95

Pro Lys Pro Gly Asp Phe Pro Arg Ser Ser Phe Ser Ser Thr Pro
1 5 10 15

<210> SEQ ID NO 96
<211> LENGTH: 15
<212> TYPE: PRT
<213> ORGANISM: Chlamydia trachomatis

<400> SEQUENCE: 96

Ser Ser Phe Ser Ser Thr Pro Pro His Ala Pro Val Pro Gln Ser
1 5 10 15

<210> SEQ ID NO 97
<211> LENGTH: 15
<212> TYPE: PRT
<213> ORGANISM: Chlamydia trachomatis

<400> SEQUENCE: 97

His Ala Pro Val Pro Gln Ser Glu Ile Pro Thr Ser Pro Thr Ser
1 5 10 15

<210> SEQ ID NO 98
<211> LENGTH: 13
<212> TYPE: PRT
<213> ORGANISM: Chlamydia trachomatis

<400> SEQUENCE: 98

Ile Pro Thr Ser Pro Thr Ser Thr Gln Pro Pro Ser Pro
1 5 10

<210> SEQ ID NO 99
<211> LENGTH: 15
<212> TYPE: PRT
<213> ORGANISM: Chlamydia trachomatis

<400> SEQUENCE: 99

Met Thr Ala Ser Gly Gly Ala Gly Gly Leu Gly Ser Thr Gln Thr
1 5 10 15

<210> SEQ ID NO 100
<211> LENGTH: 15
<212> TYPE: PRT
<213> ORGANISM: Chlamydia trachomatis

<400> SEQUENCE: 100

Gly Ala Gly Gly Leu Gly Ser Thr Gln Thr Val Asp Val Ala Arg
1 5 10 15

<210> SEQ ID NO 101
<211> LENGTH: 15
<212> TYPE: PRT
<213> ORGANISM: Chlamydia trachomatis

<400> SEQUENCE: 101

Gly Ser Thr Gln Thr Val Asp Val Ala Arg Ala Gln Ala Ala Ala
1 5 10 15

<210> SEQ ID NO 102
<211> LENGTH: 15
<212> TYPE: PRT
<213> ORGANISM: Chlamydia trachomatis

<400> SEQUENCE: 102

Val Asp Val Ala Arg Ala Gln Ala Ala Ala Ala Thr Gln Asp Ala
1 5 10 15

<210> SEQ ID NO 103
<211> LENGTH: 15
<212> TYPE: PRT
<213> ORGANISM: Chlamydia trachomatis

<400> SEQUENCE: 103

Ala Gln Ala Ala Ala Ala Thr Gln Asp Ala Gln Glu Val Ile Gly
1 5 10 15

<210> SEQ ID NO 104
<211> LENGTH: 15
<212> TYPE: PRT
<213> ORGANISM: Chlamydia trachomatis

<400> SEQUENCE: 104

Ala Thr Gln Asp Ala Gln Glu Val Ile Gly Ser Gln Glu Ala Ser
1 5 10 15

<210> SEQ ID NO 105
<211> LENGTH: 15
<212> TYPE: PRT
<213> ORGANISM: Chlamydia trachomatis

<400> SEQUENCE: 105

Gln Glu Val Ile Gly Ser Gln Glu Ala Ser Glu Ala Ser Met Leu
1 5 10 15

<210> SEQ ID NO 106
<211> LENGTH: 15
<212> TYPE: PRT
<213> ORGANISM: Chlamydia trachomatis

<400> SEQUENCE: 106

Ser Gln Glu Ala Ser Glu Ala Ser Met Leu Lys Gly Cys Glu Asp
1 5 10 15

<210> SEQ ID NO 107
<211> LENGTH: 15
<212> TYPE: PRT
<213> ORGANISM: Chlamydia trachomatis

<400> SEQUENCE: 107

Glu Ala Ser Met Leu Lys Gly Cys Glu Asp Leu Ile Asn Pro Ala
1 5 10 15

<210> SEQ ID NO 108
<211> LENGTH: 15
<212> TYPE: PRT
<213> ORGANISM: Chlamydia trachomatis

<400> SEQUENCE: 108

Lys Gly Cys Glu Asp Leu Ile Asn Pro Ala Ala Ala Thr Arg Ile
1 5 10 15

<210> SEQ ID NO 109
<211> LENGTH: 15
<212> TYPE: PRT
<213> ORGANISM: Chlamydia trachomatis

<400> SEQUENCE: 109

Leu Ile Asn Pro Ala Ala Ala Thr Arg Ile Lys Lys Lys Glu Glu
1 5 10 15

<210> SEQ ID NO 110
<211> LENGTH: 15
<212> TYPE: PRT
<213> ORGANISM: Chlamydia trachomatis

<400> SEQUENCE: 110

Ala Ala Thr Arg Ile Lys Lys Lys Glu Glu Lys Phe Glu Ser Leu
1 5 10 15

<210> SEQ ID NO 111
<211> LENGTH: 15
<212> TYPE: PRT
<213> ORGANISM: Chlamydia trachomatis

<400> SEQUENCE: 111

Lys Lys Lys Glu Glu Lys Phe Glu Ser Leu Glu Ala Arg Arg Lys
1 5 10 15

<210> SEQ ID NO 112
<211> LENGTH: 15
<212> TYPE: PRT
<213> ORGANISM: Chlamydia trachomatis

<400> SEQUENCE: 112

Lys Phe Glu Ser Leu Glu Ala Arg Arg Lys Pro Thr Ala Asp Lys
1 5 10 15

<210> SEQ ID NO 113
<211> LENGTH: 15
<212> TYPE: PRT
<213> ORGANISM: Chlamydia trachomatis

<400> SEQUENCE: 113

Glu Ala Arg Arg Lys Pro Thr Ala Asp Lys Ala Glu Lys Lys Ser
1 5 10 15

<210> SEQ ID NO 114
<211> LENGTH: 15
<212> TYPE: PRT
<213> ORGANISM: Chlamydia trachomatis

<400> SEQUENCE: 114

Pro Thr Ala Asp Lys Ala Glu Lys Lys Ser Glu Ser Thr Glu Glu
1 5 10 15

<210> SEQ ID NO 115
<211> LENGTH: 15
<212> TYPE: PRT
<213> ORGANISM: Chlamydia trachomatis

<400> SEQUENCE: 115

Ala Glu Lys Lys Ser Glu Ser Thr Glu Glu Lys Gly Asp Thr Pro
1 5 10 15

<210> SEQ ID NO 116
<211> LENGTH: 15

<212> TYPE: PRT
<213> ORGANISM: Chlamydia trachomatis

<400> SEQUENCE: 116

Glu Ser Thr Glu Glu Lys Gly Asp Thr Pro Leu Glu Asp Arg Phe
1 5 10 15

<210> SEQ ID NO 117
<211> LENGTH: 15
<212> TYPE: PRT
<213> ORGANISM: Chlamydia trachomatis

<400> SEQUENCE: 117

Lys Gly Asp Thr Pro Leu Glu Asp Arg Phe Thr Glu Asp Leu Ser
1 5 10 15

<210> SEQ ID NO 118
<211> LENGTH: 15
<212> TYPE: PRT
<213> ORGANISM: Chlamydia trachomatis

<400> SEQUENCE: 118

Leu Glu Asp Arg Phe Thr Glu Asp Leu Ser Glu Val Ser Gly Glu
1 5 10 15

<210> SEQ ID NO 119
<211> LENGTH: 15
<212> TYPE: PRT
<213> ORGANISM: Chlamydia trachomatis

<400> SEQUENCE: 119

Thr Glu Asp Leu Ser Glu Val Ser Gly Glu Asp Phe Arg Gly Leu
1 5 10 15

<210> SEQ ID NO 120
<211> LENGTH: 15
<212> TYPE: PRT
<213> ORGANISM: Chlamydia trachomatis

<400> SEQUENCE: 120

Glu Val Ser Gly Glu Asp Phe Arg Gly Leu Lys Asn Ser Phe Asp
1 5 10 15

<210> SEQ ID NO 121
<211> LENGTH: 15
<212> TYPE: PRT
<213> ORGANISM: Chlamydia trachomatis

<400> SEQUENCE: 121

Asp Phe Arg Gly Leu Lys Asn Ser Phe Asp Asp Asp Ser Ser Pro
1 5 10 15

<210> SEQ ID NO 122
<211> LENGTH: 15
<212> TYPE: PRT
<213> ORGANISM: Chlamydia trachomatis

<400> SEQUENCE: 122

Lys Asn Ser Phe Asp Asp Asp Ser Ser Pro Glu Glu Ile Leu Asp
1 5 10 15

<210> SEQ ID NO 123
<211> LENGTH: 15
<212> TYPE: PRT
<213> ORGANISM: Chlamydia trachomatis

<400> SEQUENCE: 123

Asp Asp Ser Ser Pro Glu Glu Ile Leu Asp Ala Leu Thr Ser Lys
1 5 10 15

<210> SEQ ID NO 124
<211> LENGTH: 15
<212> TYPE: PRT
<213> ORGANISM: Chlamydia trachomatis

<400> SEQUENCE: 124

Glu Glu Ile Leu Asp Ala Leu Thr Ser Lys Phe Ser Asp Pro Thr
1 5 10 15

<210> SEQ ID NO 125
<211> LENGTH: 15
<212> TYPE: PRT
<213> ORGANISM: Chlamydia trachomatis

<400> SEQUENCE: 125

Ala Leu Thr Ser Lys Phe Ser Asp Pro Thr Ile Lys Asp Leu Ala
1 5 10 15

<210> SEQ ID NO 126
<211> LENGTH: 15
<212> TYPE: PRT
<213> ORGANISM: Chlamydia trachomatis

<400> SEQUENCE: 126

Phe Ser Asp Pro Thr Ile Lys Asp Leu Ala Leu Asp Tyr Leu Ile
1 5 10 15

<210> SEQ ID NO 127
<211> LENGTH: 15
<212> TYPE: PRT
<213> ORGANISM: Chlamydia trachomatis

<400> SEQUENCE: 127

Ile Lys Asp Leu Ala Leu Asp Tyr Leu Ile Gln Thr Ala Pro Ser
1 5 10 15

<210> SEQ ID NO 128
<211> LENGTH: 15
<212> TYPE: PRT
<213> ORGANISM: Chlamydia trachomatis

<400> SEQUENCE: 128

Leu Asp Tyr Leu Ile Gln Thr Ala Pro Ser Asp Arg Lys Leu Lys
1 5 10 15

<210> SEQ ID NO 129
<211> LENGTH: 15
<212> TYPE: PRT
<213> ORGANISM: Chlamydia trachomatis

<400> SEQUENCE: 129

Gln Thr Ala Pro Ser Asp Arg Lys Leu Lys Ser Ala Leu Ile Gln
1 5 10 15

<210> SEQ ID NO 130
<211> LENGTH: 15
<212> TYPE: PRT
<213> ORGANISM: Chlamydia trachomatis

<400> SEQUENCE: 130

Asp Arg Lys Leu Lys Ser Ala Leu Ile Gln Ala Lys His Gln Leu 1 5 10 15

<210> SEQ ID NO 131
<211> LENGTH: 15
<212> TYPE: PRT
<213> ORGANISM: Chlamydia trachomatis

<400> SEQUENCE: 131

Ser Ala Leu Ile Gln Ala Lys His Gln Leu Met Ser Gln Asn Pro
1 5 10 15

<210> SEQ ID NO 132
<211> LENGTH: 15
<212> TYPE: PRT
<213> ORGANISM: Chlamydia trachomatis

<400> SEQUENCE: 132

Ala Lys His Gln Leu Met Ser Gln Asn Pro Gln Ala Ile Val Gly
1 5 10 15

<210> SEQ ID NO 133
<211> LENGTH: 15
<212> TYPE: PRT
<213> ORGANISM: Chlamydia trachomatis

<400> SEQUENCE: 133

Met Ser Gln Asn Pro Gln Ala Ile Val Gly Gly Arg Asn Val Leu
1 5 10 15

<210> SEQ ID NO 134
<211> LENGTH: 15
<212> TYPE: PRT
<213> ORGANISM: Chlamydia trachomatis

<400> SEQUENCE: 134

Gln Ala Ile Val Gly Gly Arg Asn Val Leu Leu Ala Ser Glu Thr
1 5 10 15

<210> SEQ ID NO 135
<211> LENGTH: 15
<212> TYPE: PRT
<213> ORGANISM: Chlamydia trachomatis

<400> SEQUENCE: 135

Gly Arg Asn Val Leu Leu Ala Ser Glu Thr Phe Ala Ser Arg Ala
1 5 10 15

<210> SEQ ID NO 136
<211> LENGTH: 15
<212> TYPE: PRT
<213> ORGANISM: Chlamydia trachomatis

<400> SEQUENCE: 136

Leu Ala Ser Glu Thr Phe Ala Ser Arg Ala Asn Thr Ser Pro Ser
1 5 10 15

<210> SEQ ID NO 137
<211> LENGTH: 15
<212> TYPE: PRT
<213> ORGANISM: Chlamydia trachomatis

<400> SEQUENCE: 137

Phe Ala Ser Arg Ala Asn Thr Ser Pro Ser Ser Leu Arg Ser Leu
1 5 10 15

<210> SEQ ID NO 138
<211> LENGTH: 15
<212> TYPE: PRT
<213> ORGANISM: Chlamydia trachomatis

<400> SEQUENCE: 138

```
Asn Thr Ser Pro Ser Ser Leu Arg Ser Leu Tyr Leu Gln Val Thr
1               5                   10                  15
```

<210> SEQ ID NO 139
<211> LENGTH: 15
<212> TYPE: PRT
<213> ORGANISM: Chlamydia trachomatis

<400> SEQUENCE: 139

```
Ser Leu Arg Ser Leu Tyr Leu Gln Val Thr Ser Ser Pro Ser Asn
1               5                   10                  15
```

<210> SEQ ID NO 140
<211> LENGTH: 15
<212> TYPE: PRT
<213> ORGANISM: Chlamydia trachomatis

<400> SEQUENCE: 140

```
Tyr Leu Gln Val Thr Ser Ser Pro Ser Asn Cys Asp Asn Leu Arg
1               5                   10                  15
```

<210> SEQ ID NO 141
<211> LENGTH: 15
<212> TYPE: PRT
<213> ORGANISM: Chlamydia trachomatis

<400> SEQUENCE: 141

```
Ser Ser Pro Ser Asn Cys Asp Asn Leu Arg Gln Met Leu Ala Ser
1               5                   10                  15
```

<210> SEQ ID NO 142
<211> LENGTH: 15
<212> TYPE: PRT
<213> ORGANISM: Chlamydia trachomatis

<400> SEQUENCE: 142

```
Cys Asp Asn Leu Arg Gln Met Leu Ala Ser Tyr Leu Pro Ser Glu
1               5                   10                  15
```

<210> SEQ ID NO 143
<211> LENGTH: 15
<212> TYPE: PRT
<213> ORGANISM: Chlamydia trachomatis

<400> SEQUENCE: 143

```
Gln Met Leu Ala Ser Tyr Leu Pro Ser Glu Lys Thr Ala Val Met
1               5                   10                  15
```

<210> SEQ ID NO 144
<211> LENGTH: 15
<212> TYPE: PRT
<213> ORGANISM: Chlamydia trachomatis

<400> SEQUENCE: 144

```
Tyr Leu Pro Ser Glu Lys Thr Ala Val Met Glu Phe Leu Val Asn
1               5                   10                  15
```

<210> SEQ ID NO 145
<211> LENGTH: 15
<212> TYPE: PRT

<213> ORGANISM: Chlamydia trachomatis

<400> SEQUENCE: 145

Lys Thr Ala Val Met Glu Phe Leu Val Asn Gly Met Val Ala Asp
1 5 10 15

<210> SEQ ID NO 146
<211> LENGTH: 15
<212> TYPE: PRT
<213> ORGANISM: Chlamydia trachomatis

<400> SEQUENCE: 146

Glu Phe Leu Val Asn Gly Met Val Ala Asp Leu Lys Ser Glu Gly
1 5 10 15

<210> SEQ ID NO 147
<211> LENGTH: 15
<212> TYPE: PRT
<213> ORGANISM: Chlamydia trachomatis

<400> SEQUENCE: 147

Gly Met Val Ala Asp Leu Lys Ser Glu Gly Pro Ser Ile Pro Pro
1 5 10 15

<210> SEQ ID NO 148
<211> LENGTH: 15
<212> TYPE: PRT
<213> ORGANISM: Chlamydia trachomatis

<400> SEQUENCE: 148

Leu Lys Ser Glu Gly Pro Ser Ile Pro Pro Ala Lys Leu Gln Val
1 5 10 15

<210> SEQ ID NO 149
<211> LENGTH: 15
<212> TYPE: PRT
<213> ORGANISM: Chlamydia trachomatis

<400> SEQUENCE: 149

Pro Ser Ile Pro Pro Ala Lys Leu Gln Val Tyr Met Thr Glu Leu
1 5 10 15

<210> SEQ ID NO 150
<211> LENGTH: 15
<212> TYPE: PRT
<213> ORGANISM: Chlamydia trachomatis

<400> SEQUENCE: 150

Ala Lys Leu Gln Val Tyr Met Thr Glu Leu Ser Asn Leu Gln Ala
1 5 10 15

<210> SEQ ID NO 151
<211> LENGTH: 15
<212> TYPE: PRT
<213> ORGANISM: Chlamydia trachomatis

<400> SEQUENCE: 151

Tyr Met Thr Glu Leu Ser Asn Leu Gln Ala Leu His Ser Val Asp
1 5 10 15

<210> SEQ ID NO 152
<211> LENGTH: 15
<212> TYPE: PRT
<213> ORGANISM: Chlamydia trachomatis

<400> SEQUENCE: 152

Ser Asn Leu Gln Ala Leu His Ser Val Asp Ser Phe Phe Asp Arg
1 5 10 15

<210> SEQ ID NO 153
<211> LENGTH: 15
<212> TYPE: PRT
<213> ORGANISM: Chlamydia trachomatis

<400> SEQUENCE: 153

Leu His Ser Val Asp Ser Phe Phe Asp Arg Asn Ile Gly Asn Leu
1 5 10 15

<210> SEQ ID NO 154
<211> LENGTH: 15
<212> TYPE: PRT
<213> ORGANISM: Chlamydia trachomatis

<400> SEQUENCE: 154

Ser Phe Phe Asp Arg Asn Ile Gly Asn Leu Glu Asn Ser Leu Lys
1 5 10 15

<210> SEQ ID NO 155
<211> LENGTH: 15
<212> TYPE: PRT
<213> ORGANISM: Chlamydia trachomatis

<400> SEQUENCE: 155

Asn Ile Gly Asn Leu Glu Asn Ser Leu Lys His Glu Gly His Ala
1 5 10 15

<210> SEQ ID NO 156
<211> LENGTH: 15
<212> TYPE: PRT
<213> ORGANISM: Chlamydia trachomatis

<400> SEQUENCE: 156

Glu Asn Ser Leu Lys His Glu Gly His Ala Pro Ile Pro Ser Leu
1 5 10 15

<210> SEQ ID NO 157
<211> LENGTH: 15
<212> TYPE: PRT
<213> ORGANISM: Chlamydia trachomatis

<400> SEQUENCE: 157

His Glu Gly His Ala Pro Ile Pro Ser Leu Thr Thr Gly Asn Leu
1 5 10 15

<210> SEQ ID NO 158
<211> LENGTH: 15
<212> TYPE: PRT
<213> ORGANISM: Chlamydia trachomatis

<400> SEQUENCE: 158

Pro Ile Pro Ser Leu Thr Thr Gly Asn Leu Thr Lys Thr Phe Leu
1 5 10 15

<210> SEQ ID NO 159
<211> LENGTH: 15
<212> TYPE: PRT
<213> ORGANISM: Chlamydia trachomatis

<400> SEQUENCE: 159

Thr Thr Gly Asn Leu Thr Lys Thr Phe Leu Gln Leu Val Glu Asp
1 5 10 15

<210> SEQ ID NO 160
<211> LENGTH: 15
<212> TYPE: PRT
<213> ORGANISM: Chlamydia trachomatis

<400> SEQUENCE: 160

Thr Lys Thr Phe Leu Gln Leu Val Glu Asp Lys Phe Pro Ser Ser
1 5 10 15

<210> SEQ ID NO 161
<211> LENGTH: 15
<212> TYPE: PRT
<213> ORGANISM: Chlamydia trachomatis

<400> SEQUENCE: 161

Gln Leu Val Glu Asp Lys Phe Pro Ser Ser Ser Lys Ala Gln Lys
1 5 10 15

<210> SEQ ID NO 162
<211> LENGTH: 15
<212> TYPE: PRT
<213> ORGANISM: Chlamydia trachomatis

<400> SEQUENCE: 162

Lys Phe Pro Ser Ser Ser Lys Ala Gln Lys Ala Leu Asn Glu Leu
1 5 10 15

<210> SEQ ID NO 163
<211> LENGTH: 15
<212> TYPE: PRT
<213> ORGANISM: Chlamydia trachomatis

<400> SEQUENCE: 163

Ser Lys Ala Gln Lys Ala Leu Asn Glu Leu Val Gly Pro Asp Thr
1 5 10 15

<210> SEQ ID NO 164
<211> LENGTH: 15
<212> TYPE: PRT
<213> ORGANISM: Chlamydia trachomatis

<400> SEQUENCE: 164

Ala Leu Asn Glu Leu Val Gly Pro Asp Thr Gly Pro Gln Thr Glu
1 5 10 15

<210> SEQ ID NO 165
<211> LENGTH: 15
<212> TYPE: PRT
<213> ORGANISM: Chlamydia trachomatis

<400> SEQUENCE: 165

Val Gly Pro Asp Thr Gly Pro Gln Thr Glu Val Leu Asn Leu Phe
1 5 10 15

<210> SEQ ID NO 166
<211> LENGTH: 15
<212> TYPE: PRT
<213> ORGANISM: Chlamydia trachomatis

<400> SEQUENCE: 166

Gly Pro Gln Thr Glu Val Leu Asn Leu Phe Phe Arg Ala Leu Asn
1 5 10 15

<210> SEQ ID NO 167

<211> LENGTH: 15
<212> TYPE: PRT
<213> ORGANISM: Chlamydia trachomatis

<400> SEQUENCE: 167

Val Leu Asn Leu Phe Phe Arg Ala Leu Asn Gly Cys Ser Pro Arg
1 5 10 15

<210> SEQ ID NO 168
<211> LENGTH: 15
<212> TYPE: PRT
<213> ORGANISM: Chlamydia trachomatis

<400> SEQUENCE: 168

Phe Arg Ala Leu Asn Gly Cys Ser Pro Arg Ile Phe Ser Gly Ala
1 5 10 15

<210> SEQ ID NO 169
<211> LENGTH: 15
<212> TYPE: PRT
<213> ORGANISM: Chlamydia trachomatis

<400> SEQUENCE: 169

Gly Cys Ser Pro Arg Ile Phe Ser Gly Ala Glu Lys Lys Gln Gln
1 5 10 15

<210> SEQ ID NO 170
<211> LENGTH: 15
<212> TYPE: PRT
<213> ORGANISM: Chlamydia trachomatis

<400> SEQUENCE: 170

Ile Phe Ser Gly Ala Glu Lys Lys Gln Gln Leu Ala Ser Val Ile
1 5 10 15

<210> SEQ ID NO 171
<211> LENGTH: 15
<212> TYPE: PRT
<213> ORGANISM: Chlamydia trachomatis

<400> SEQUENCE: 171

Glu Lys Lys Gln Gln Leu Ala Ser Val Ile Thr Asn Thr Leu Asp
1 5 10 15

<210> SEQ ID NO 172
<211> LENGTH: 15
<212> TYPE: PRT
<213> ORGANISM: Chlamydia trachomatis

<400> SEQUENCE: 172

Leu Ala Ser Val Ile Thr Asn Thr Leu Asp Ala Ile Asn Ala Asp
1 5 10 15

<210> SEQ ID NO 173
<211> LENGTH: 15
<212> TYPE: PRT
<213> ORGANISM: Chlamydia trachomatis

<400> SEQUENCE: 173

Thr Asn Thr Leu Asp Ala Ile Asn Ala Asp Asn Glu Asp Tyr Pro
1 5 10 15

<210> SEQ ID NO 174
<211> LENGTH: 15
<212> TYPE: PRT
<213> ORGANISM: Chlamydia trachomatis

<400> SEQUENCE: 174

Ala Ile Asn Ala Asp Asn Glu Asp Tyr Pro Lys Pro Gly Asp Phe
1 5 10 15

<210> SEQ ID NO 175
<211> LENGTH: 15
<212> TYPE: PRT
<213> ORGANISM: Chlamydia trachomatis

<400> SEQUENCE: 175

Asn Glu Asp Tyr Pro Lys Pro Gly Asp Phe Pro Arg Ser Ser Phe
1 5 10 15

<210> SEQ ID NO 176
<211> LENGTH: 15
<212> TYPE: PRT
<213> ORGANISM: Chlamydia trachomatis

<400> SEQUENCE: 176

Lys Pro Gly Asp Phe Pro Arg Ser Ser Phe Ser Ser Thr Pro Pro
1 5 10 15

<210> SEQ ID NO 177
<211> LENGTH: 15
<212> TYPE: PRT
<213> ORGANISM: Chlamydia trachomatis

<400> SEQUENCE: 177

Pro Arg Ser Ser Phe Ser Ser Thr Pro Pro His Ala Pro Val Pro
1 5 10 15

<210> SEQ ID NO 178
<211> LENGTH: 15
<212> TYPE: PRT
<213> ORGANISM: Chlamydia trachomatis

<400> SEQUENCE: 178

Ser Ser Thr Pro Pro His Ala Pro Val Pro Gln Ser Glu Ile Pro
1 5 10 15

<210> SEQ ID NO 179
<211> LENGTH: 15
<212> TYPE: PRT
<213> ORGANISM: Chlamydia trachomatis

<400> SEQUENCE: 179

His Ala Pro Val Pro Gln Ser Glu Ile Pro Thr Ser Pro Thr Ser
1 5 10 15

<210> SEQ ID NO 180
<211> LENGTH: 16
<212> TYPE: PRT
<213> ORGANISM: Chlamydia trachomatis

<400> SEQUENCE: 180

Gln Ser Glu Ile Pro Thr Ser Pro Thr Ser Thr Gln Pro Pro Ser Pro
1 5 10 15

<210> SEQ ID NO 181
<211> LENGTH: 9
<212> TYPE: PRT
<213> ORGANISM: Chlamydia trachomatis

<400> SEQUENCE: 181

Ile Lys Lys Lys Gly Glu Lys Phe Glu
1               5

<210> SEQ ID NO 182
<211> LENGTH: 9
<212> TYPE: PRT
<213> ORGANISM: Chlamydia trachomatis

<400> SEQUENCE: 182

Ile Lys Lys Lys Glu Glu Lys Phe Glu
1               5

<210> SEQ ID NO 183
<211> LENGTH: 9
<212> TYPE: PRT
<213> ORGANISM: Chlamydia trachomatis

<400> SEQUENCE: 183

Lys Leu Lys Ser Thr Leu Ile Gln Ala
1               5

<210> SEQ ID NO 184
<211> LENGTH: 9
<212> TYPE: PRT
<213> ORGANISM: Chlamydia trachomatis

<400> SEQUENCE: 184

Lys Leu Lys Ser Ala Leu Ile Gln Ala
1               5

<210> SEQ ID NO 185
<211> LENGTH: 421
<212> TYPE: PRT
<213> ORGANISM: Chlamydia trachomatis
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (420)..(420)

<223> OTHER INFORMATION: Xaa can be any naturally occurring amino acid

<400> SEQUENCE: 185

```
Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Xaa
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Xaa Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Xaa Lys Leu Lys
145                 150                 155                 160

Ser Xaa Leu Ile Gln Ala Lys His Gln Leu Met Ser Gln Asn Pro Gln
                165                 170                 175

Ala Ile Xaa Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Xaa Gln
        195                 200                 205

Val Thr Ser Ser Pro Ser Asn Cys Xaa Asn Leu Xaa Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Xaa Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400
```

-continued

```
His Ala Pro Val Pro Gln Ser Glu Ile Pro Thr Ser Pro Thr Ser Thr
                405                 410                 415

Gln Pro Pro Xaa Pro
            420
```

IMMUNOGENIC COMPOSITIONS FOR *CHLAMYDIA TRACHOMATIS*

This application is a national phase application of PCT/US2006/018504 filed May 12, 2006, which was published in English under PCT Article 21(2) on Dec. 28, 2006 and which claims the benefit of U.S. Provisional Application 60/680,725, filed May 12, 2005, which is incorporated herein in its entirety.

This application incorporates by reference the contents of a 91.2 kb text file created on Mar. 9, 2010 and named "SN11920230_sequencelisting.txt," which is the sequence listing for this application.

This application incorporates by reference the contents of each of two duplicate CD-ROMs. Each CD-ROM contains an identical 95 kB file labeled "Sequence Listing for 2441_199.txt" and containing the sequence listing for this application. The CD-ROMs were created on May 3, 2006.

All documents cited herein are incorporated by reference in their entirety.

TECHNICAL FIELD

This invention is in the fields of immunology and vaccinology. In particular, it relates to antigens derived from *Chlamydia trachomatis* and their use in immunisation.

BACKGROUND ART

The Chlamydiae are obligate intracellular parasites of eukaryotic cells which are responsible for endemic sexually transmitted infections and various other disease syndromes. They occupy an exclusive eubacterial phylogenic branch, having no close relationship to any other known organisms. A particular characteristic of the Chlamydiae is their unique life cycle, in which the bacterium alternates between two morphologically distinct forms: an extracellular infective form (elementary bodies, EB) and an intracellular non-infective form (reticulate bodies, RB). The life cycle is completed with the re-organization of RB into EB, which leave the disrupted host cell ready to infect further cells.

Historically, the Clamydiae have been classified in their own order (Chlamydiales) made up of a single family (Chlamydiaceae) which in turn contains a single genus (*Chlamydia* also referred to as *Chlamydophila*). More recently, this order has been divided into at least four families including Chlamydia trachomatisceae, ParaChlamydia trachomatisceae, Waddiaceae and Simkaniaceae. In this more recent classification, the Chlamydiaceae family includes genuses of *Chlamydophila* and *Chlamydia trachomatis, Chlamydia trachomatis* being a species within the *Chlamydia* genus. See Ref. 1.

The genome sequences of at least five *Chlamydia trachomatis* or *chlamydophila* species are currently known—*C. trachomatis, C. pneumoniae, C. muridarum, C. pecorum* and *C. psittaci* (See Refs. 2, 8). The various *C. trachomatis* strains, of which there are currently at least 18 serovars, may be classified according to their serological reactivities with polyclonal or monoclonal antisera (i.e., "serovars"). These serological differences are typically detected due to differences in the MOMP (Major Outer Membrane Protein) of *C. trachomatis.*

The human serovariants ("serovars") of *C. trachomatis* are divided into two biovariants ("biovars"). Serovars L1, L2 and L3 are the agents of invasive lymphogranuloma venereum (LGV) which is a sexually transmitted systemic infection. LGV is uncommon in industralised countries but frequent in Africa, Asia, Australian and South America. It predominantly affects lymphatic tissue but may also occur as an acute symptomatic infection without apparent lymph node involvement or tissue reaction at the point of infection. Acute LGV is reported over five times more frequent in men than in women. Other biotypes of *C. trachomatis* include serovars A, B, Ba, and C which are associated with trachoma, a transmissible condition of the eye.

Serovars A-K (D, E, F, G, H, I, J, and K) are typically associated with genital tract disease. In particular, Serovars D, E, F, H and K account for nearly 85% of genital tract infections (see for example, WO 02/065129) Serovars A-K elicit epithelial infections primarily in the ocular tissue (A-C) or urogenital tract (D-K). Research to date also indicates that the 4 Serovars (or serotypes) responsible for Sexually Transmitted Infections or Diseases (STIs or STDs) in the US and Europe are D-K, preferably D, E, F and I.

More than 4 million new cases of *Chlamydia* sexually transmitted infections are diagnosed each year in the United States alone (8) and the cost of their treatment has been estimated in 4 billion dollars annually, with 80% attributed to infection and disease of women (9).

Although *Chlamydia* infection itself causes disease, it is thought that the severity of symptoms in some, patients is actually due to an aberrant or an altered host immune response which may arise from either (i) the nature of the invading *Chlamydia* organism which may vary from serovar to serovar or (ii) the nature of the subject invaded (for example, the nature of the patient profile). The failure to clear the infection results in persistent immune stimulation and, rather than helping the most, this results in chronic infection with severe consequences, including sterility and blindness. See, e.g., Ref. 9. In addition, the protection conferred by natural Chlamydial infection is usually incomplete, transient, and strain-specific.

Although *Chlamydia* infections can be treated with several antibiotics, a majority of the female infections are asymptomatic, and antimicrobial therapy may be delayed or inadequate to prevent long term sequelae, expecially in countries with poor hygienic conditions. Multiple-antibiotic-resistant strains of *Chlamydia* have also been reported (Somani, et al., 2000). Furthermore it has been suggested that antibiotic treatment could lead to the formation of aberrant or altered forms of *C. trachomatis* that may be reactivated later on (Hammerschlag M. R. 2002. The intracellular life of *Chlamydia trachomatis* Semin. Pediatr. Infect. Dis. 13:239-248).

Unfortunately the major determinants of *Chlamydia* pathogenesis are complicated and at present still unclear, mostly due to the intrinsic difficulty in working with this pathogen and the lack of adequate methods for its genetic manipulation. In particular very little is known about the antigenic composition of elementary body surface, that is an essential compartment in pathogen-host interactions, and likely to carry antigens able to elicit a protective immune response.

Due to the serious nature of the disease, there is a desire to provide suitable immunogenic compositions, such as vaccines to deal with an aberrant or altered host cell immune response which may result from, for example, allelic variation in the invading *Chlamydia* strain and/or aberrant or altered forms of *Chlamydia* invading strain. These immunogenic compositions may be useful (a) for immunisation against Chlamydial infection or against *Chlamydia*-induced disease (prophylactic vaccination) or (b) for the eradication of an established chronic *Chlamydia* infection (therapeutic vaccination). Being an intracellular parasite, however, the bacterium can generally evade antibody-mediated immune responses.

Various antigenic proteins have been described for *C. trachomatis*, and, the cell surface in particular has been the target of detailed research. See, e.g., Ref. 10. These include, for instance, Pgp3 (Refs. 11, 12, and 13), MOMP (Ref. 14), Hsp60 (GroEL) (Ref. 15) and Hsp70 (DnaK-like) (Ref. 16). Not all of these have proved to be effective vaccines, however, and further candidates have been identified. See Ref. 17.

Vaccines against pathogens such as hepatitis B virus, diphtheria and tetanus typically contain a single protein antigen (e.g. the HBV surface antigen, or a tetanus toxoid). In contrast, acellular whooping cough vaccines typically have at least three *B. pertussis* proteins, and the Prevnar™ pneumococcal vaccine contains seven separate conjugated saccharide antigens. Other vaccines such as cellular pertussis vaccines, the measles vaccine, the inactivated polio vaccine (IPV) and meningococcal OMV vaccines are by their very nature complex mixtures of a large number of antigens. Whether protection can be elicited by a single antigen, a small number of defined antigens, or a complex mixture of undefined antigens, therefore depends on the pathogen in question.

It is an object of the invention to provide further and improved immunogenic compositions for providing immunity against Chlamydial disease and/or infection. In particular, it is an object of the invention to provide improved immunogenic compositions for providing immunity against aberrant or altered *Chlamydia* serovar strains (eg strains such as allelic variant strains).

The immunogenic compositions of the present invention are based on a combination of one or more (e.g. two or more) *C. trachomatis* antigens. The immunogenic compositions may include one or more of the same *Chlamydia trachomatis* antigens from different *Chlamydia trachomatis* serovars and/or one of more of the same or different *Chlamydia trachomatis* antigen from the different *Chlamydia trachomatis* serovars.

SUMMARY OF THE INVENTION

Within the ~900 proteins described for the *C. trachomatis* genome of reference 5, the Applicants were the first to show that the Low Calcium Response Element (LcrE) protein is present and accessible to antibodies on the surface of the infectious EB form thus marking this protein a possible vaccine candidate. The Applicants hypothesised at the time that an efficient block of the Type Three Section or TTS organelle (of which LcrE is a part) may in turn inhibit the infection process by "freezing" the LcrE negative regulator (see Montigiani et al Infection and Immunity (2002) 70(1); 368-379). Applicants have subsequently demonstrated that the LcrE protein is indeed capable of inducing a significantly protective immune response in a hamster model of *C. trachomatis* infection (see Sambri et al (2004) 22(9-10) 1131-7). These immunoprotective results for LcrE have also been confirmed by others (see for example, Example 9 in WO 03/41560) and point towards the value of LcrE as a good candidate for the prevention and/or treatment and/or diagnosis of a *C. trachomatis* infection.

In the course of evaluating the allelic variation for the LcrE gene in 14 *C. trachomatis* clinical isolates representative of 8 different *C. trachomatis* serovars, the Applicants established that a higher than expected number of single amino acidic substitutions across the *C. trachomatis* serovars was observed for the LcrE antigen relative to (i) a reference *Chlamydia trachomatis* LcrE sequence from Serovar D and (ii) those found for other immunogenic *Chlamydia trachomatis* antigens.

This highly unexpected and surprising finding suggests that:

(i) the LcrE protein may be subjected to a greater immunological pressure that other immunogenic *Chlamydia trachomatis* antigens; and (ii) the peptides surrounding the amino acid substitutions are likely to be epitopic regions (either B-cell epitopes involved in antibody-antigen (Ab-Ag) interactions and/or T-cell epitopes capable of eliciting *Chlamydia* specific cell mediated responses.

Applicants finding is all the more surprising because the *Chlamydia* isolates used for these genotyping studies came from two very divergent immunological sources which were isolated from two different Continents (North America and Europe) and over different time periods (minimum of 30 years ago versus 5-8 years ago).

Given that it is surprising that an LcrE sequence from a not so recently isolated ATCC Serovar E can have the same number of mutations as an LcrE sequence from a recently isolated Italian Serovar E, it is even highly surprising and unexpected that the nature of the eight mutations is the same in both LcrE sequences from both sources. The fact that both LcrE Serovar E mutant sequences are the same points towards a finding that these eight mutations are true and real mutations as opposed to random or arbitrary mutations. These mutations may be used to tailor LcrE immunogenic compositions to specific target groups.

Applicants have also identified two high frequency mutation points or hypervariable regions at amino acid residues 64 and 162 in the LcrE sequence across the serovars. At amino acid residue 64, there are seven mutations from Glycine (G) to Glutamic (E) acid across the 14 different *Chlamydia* isolates while at point 162, there are also seven mutations from Threonine (T) to Alanine (A) across the 14 *Chlamydia* isolates. The existence of two high frequency mutation points or hypervariable regions (eg at residues 64 and 162 of the LcrE sequence is surprising and unexpected and is likely to be associated with the presence of T and/or B cell epitopic regions capable of eliciting an immunogenic response in a subject. These high frequency mutations may be used to tailor LcrE immunogenic compositions to specific target groups.

Applicants have also identified other variant *Chlamydia* antigen sequences and/or combinations of variant *Chlamydia* antigen sequences across the *Chlamydia trachomatis* serovars. These *Chlamydia* antigens include but are not limited to OmpH-like (CT242), ArtJ (CT381), DnaK (CT396), Hypothetical (CT398) and PepA (CT045) antigens. The amino acid changes observed in these *Chlamydia* antigen genotypes across the *Chlamydia trachomatis* serovars are likely to correspond with changes in the *Chlamydia* antigen phenotypes, in particular, with changes in immunogenicity. The peptides surrounding or associated with the amino acid substitutions, in particular, peptides surrounding or associated with high frequency mutated amino acid positions or hypervariable regions, are likely to be epitopic regions which are either B-cell epitopes involved in antibody-antigen (Ab-Ag) interactions and/or T-cell epitopes capable of eliciting *Chlamydia* specific immunogenic responses, in particular, cell mediated immune responses.

BRIEF DESCRIPTION OF THE SEQUENCES

The following Table provides a brief Description of the *Chlamydia trachomatis* LcrE sequences (SEQ ID Nos 1-13)

found across the 13 isolated *Chlamydia trachomatis* serovars. Of these Serovars, seven serovars were obtained from the ATCC, and 6 serovars were obtained from an Italian (Cevenini) collection. There is also provided 14×30 mer consensus sequences for the LcrE sequences (SEQ ID Nos 14-SEQ ID Nos 27). SEQ ID No 28 corresponds to an LcrE sequence with all 10, mutations points (64, 126, 157, 162, 179, 207, 217, 220, 275 and 420) found across the *Chlamydia trachomatis* LcrE Serovars. SEQ ID Nos 29-45 correspond to the identified epitope regions found around the mutant sequences. SEQ ID No 46 is the reference LcrE Serovar D sequence from Serovar D/UW-3/CX against which comparisons with the other sequences were made. SEQ ID Nos 181, 182, 183 and 184 correspond with epitopic regions associated with the high frequency mutation points at residues 64 and 162.

TABLE 1

| Antigen | Serovar | Sequence ID No |
|---|---|---|
| LcrE reference sequence from Serovar D/UW-3/CX (gi:15604717) (Stephens et al (1998) Science 282 (5389) 754-759 | LcrE reference sequence from Serovar D | SEQ ID No 46 |
| LcrE | ATCC Serovar E | SEQ ID No 1 |
| LcrE | ATCC Serovar F | SEQ ID No 2 |
| LcrE | ATCC Serovar G | SEQ ID No 3 |
| LcrE | ATCC Serovar H | SEQ ID No 4 |
| LcrE | ATCC Serovar I | SEQ ID No 5 |
| LcrE | ATCC Serovar J | SEQ ID No 6 |
| LcrE | ATCC Serovar K | SEQ ID No 7 |
| LcrE | Cev 1 = Serovar J | SEQ ID No 8 |
| LcrE | Cev 2 = Serovar G | SEQ ID No 9 |
| LcrE | Cev 4 = Serovar H | SEQ ID No 10 |
| LcrE | Cev 5 = Serovar E | SEQ ID No 11 |
| LcrE | Cev 8 = Serovar D | SEQ ID No 12 |
| LcrE | G086 = Serovar D | SEQ ID No 13 |
| LcrE | 30 mer consensus sequences I-14 | SEQ ID No 14-27 |
| LcrE | LcrE Serovar D reference sequence from D/UW-3/CX with identified 10 mutation points | SEQ ID No 28 |
| LcrE | Epitope peptide sequences 1-17 | SEQ ID Nos 29-45 |
| | Peptides comprising epitope sequences | SEQ ID Nos 47-98 and 99-180 |
| LcrE | Epitope sequence associated with two high frequency mutation points 64 and 162 in the LcrE sequence | SEQ ID Nos 181, 182, 183 and 184 |
| LcrE | LcrE Serovar D reference sequence from D/UW-3/CX with identified 10 mutation points listed as X1-X10 | SEQ ID No 185 |

TABLE 7

| LcrE Amino acid residue | Reference amino acid | Mutated amino acid |
|---|---|---|
| X1 = 64 | Glycine (G) | Glutamic acid (E) |
| X2 = 126 | Aspartic acid (D) | Glutamic acid (E) or Asparagine (N) |
| X3 = 157 | Glycine (G) | Arginine ® |
| X4 = 162 | Threonine (T) | Alanine (A) |
| X5 = 179 | Valine (V) | Isoleucine (I) |
| X6 = 207 | Phenylalanine (F) | Leucine (L) |
| X7 = 217 | Alanine (A) | Aspartic Acid (D) |
| X8 = 220 | Histidine (H) | Arginine ® |
| X9 = 275 | Asparagine (N) | Aspartic acid (D) |
| X10 = 420 | Serine (S) | Proline (P) |

SUMMARY ASPECTS OF THE INVENTION

The present invention relates to the variations in the *Chlamydia trachomatis* LcrE sequence found across the *Chlamydia trachomatis* serovars. The variations in the *Chlamydia trachomatis* LcrE sequence across the *Chlamydia trachomatis* serovars are measured relative to the *Chlamydia trachomatis* LcrE Serovar D/UW-3/CX sequence (SEQ ID No 46). The following paragraphs (para(s)) are provided which set out various aspects of the invention. Further details are provided in the accompanying disclosure:

In the present invention, there is provided:

1. A protein consisting of an amino acid sequence of SEQ ID NO: 46, except that the amino acid sequence contains one or more mutations, wherein the one or more mutation(s) involves an amino acid residue(s) selected from the group consisting of 64, 126, 157, 162, 179, 207, 217, 220, 275 and/or 420.

2. The protein according to para 1 wherein the mutation is independently a substitution, an insertion or a deletion, preferably comprising one or more of the mutations listed in Table 7.

3. The protein of para 1 or para 2 wherein the one or more mutation(s) alter the immunogenicity of the protein.

4. The protein of any one of paras 1 to 3 wherein the protein comprises one or more mutated sequences selected from the group of sequences consisting of SEQ ID Nos 1, 4, 6, 8, 11, 12, 13, 16, 18, 19, 20, 21, 23 and/or 27.

5. The protein of para 4 comprising SEQ ID No 11, 4 or 6.

6. The protein of para 4 comprising SEQ ID No 13 or 8.

7. The protein of para 4 comprising SEQ ID No 12 or 1.

8. The protein of para 2 comprising a mutation at amino acid residue 64 and/or 162.

9. The protein of para 4 comprising SEQ ID No 16, 18, 19, 20, 21, 22, 23 or 27.

10. A protein comprising the amino acid sequence of a protein according to any one of the preceding paras or one or more fragment(s) of at least 7 consecutive amino acids of a protein according to any one of the preceding paras.

11. The protein of para 10 wherein the one or more fragment(s) comprises one or more mutations involving an amino acid residue(s) selected from the group consisting of 64, 126, 157, 162, 179, 207, 217, 220, 275 and/or 420.

12. An antibody which binds to a protein of any one of paras 1-11.

13. A nucleic acid encoding the protein of any one of paras 1-11.

14. A vector comprising a nucleic acid according to para 13.

15. A host cell transformed with a vector according to para 14.

16. The protein of any one of paras 1-11, an antibody according to para 12 or a nucleic acid according to para 13 for use as a medicament.

17. The protein or nucleic acid of para 16 for use as an immunogen.

18. The protein of any one of paras 1-11, an antibody according to para 12 or a nucleic acid according to para 13 for use as a diagnostic reagent.

19. The use of the protein as defined in any one of paras 1-11, the antibody according to para 12 or the nucleic acid according to para 13 in the manufacture of a medicament for preventing or treating a *Chlamydia trachomatis* infection.

20. The use of the protein as defined in any one of paras 1-11, the antibody according to para 12 or the nucleic acid according to para 13 in the manufacture of a diagnostic reagent for detecting the presence of *Chlamydia trachomatis* or of antibodies raised against *Chlamydia trachomatis.*

21. The use of the protein as defined in any one of paras 1-11, the antibody according to para 12 or the nucleic acid according to para 13. in the manufacture of a reagent which can raise antibodies against *Chlamydia trachomatis.*

22. A method of treating a subject comprising administering to the subject a therapeutically effective amount of a protein according to any one of paras 1-11, an antibody according to para 12 or a nucleic acid according to para 13.

23. A process for producing a protein according to any one of paras 1-11, the antibody according to para 12 or the nucleic acid according to para 13 comprising the step of culturing a host cell according to para 15 under conditions which induce protein expression.

24. A process for producing a protein according to any one of paras 1-11, the antibody according to para 12 or the nucleic acid according to para 13 wherein the protein or nucleic acid is synthesised in part or in whole using chemical means.

25. A process for detecting a nucleic acid according to para 13 comprising the steps of (a) contacting a nucleic acid probe with a biological sample under hybridising conditions to form duplexes and (b) detecting said duplexes.

26. A process for detecting a protein according to any one of paras 1-11 comprising the steps of (a) contacting an antibody according to para 12 with a biological sample under conditions suitable for the formation of antibody-antigen complexes and (b) detecting said complexes.

27. A process for detecting an antibody according to para 12 comprising the steps of: contacting a protein according to any one of paras 1-11 with a biological sample under conditions suitable for the formation of an antibody-antigen complexes and (b) detecting said complexes.

28. A kit comprising reagents suitable for use in a process according to any one of paras 25-28.

29. An immunogenic composition comprising the protein of any one of paras 1-11, the antibody of example 12 or the nucleic acid of example 13 and an immunologically acceptable excipient.

30. The composition of para 29 further comprising one or more antigen(s).

31. The composition of para 29 or 30 further comprising one or more adjuvant(s).

32. The composition of any one of paras 29-31 for use as a medicament.

33. Use of a composition of any one of paras 29-31 in the manufacture of a medicament for preventing or treating or diagnosing a bacterial infection.

34. The use according to para 33 wherein the bacterial infection is a *Chlamydia trachomatis* infection.

35. An immunogenic composition comprising at least two proteins selected from the group of sequences consisting of SEQ ID Nos 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, and 45, 49-98, 99-180, 181, 182, 183 and/or 184.

36. The composition according to para 35 wherein the composition comprises SEQ ID No 1 and SEQ ID No 12.

37. The composition according to para 36 wherein the composition comprises SEQ ID No 13 and SEQ ID No 46.

38. The composition according to any one of paras 35-37 comprising (a) one or more further antigen(s) and/or (d) one or more further adjuvant(s).

39. The composition of any one of paras 35-38 for use as a medicament.

40. Use of a composition of any one of paras 35-38 in the manufacture of a medicament for preventing or treating or diagnosing a bacterial infection.

41. The use according to example 40 wherein the bacterial infection is a *Chlamydia trachomatis* infection.

42. A method of eliciting an immune response in a subject wherein the method comprises administering to a subject a composition according to any one of paras 29-31 or 35-38.

43. A polypeptide comprising one or more fragment(s) of at least 7 consecutive amino acids, preferably at least 9 consecutive amino acids, selected from the group consisting of SEQ 29, 30, 31, 32, 33, 34, 35, 36, 37, 38, 39, 40, 41, 42, 43, 44 and 45, 47-98, 99-180, 55, 66, 109, 110, 111, 181, 182, 183 and/or 184.

44. The composition according to para 35 having proteins comprising SEQ ID NOS: 1, 12, 13, 45, and 7.

46. An immunogenic composition comprising one of more peptides selected from the group consisting of SEQ ID Nos 54, 66, 109, 110, 111, 181, 182, 183 and 184.

47. An immunogenic composition comprising one of more peptides selected from the group consisting of SEQ ID Nos 181, 182, 183 and/or 184.

48. The polypeptide according to para 43 or the composition according to paras 46 or 47 for use as an immunogen.

49. The polypeptide according to para 48 wherein the use is as an immunogen for raising a humoural and/or a cytotoxic T cell lymphocyte response which is sufficient to protect or treat a disease and/or infection caused by *Chlamydia.*

50. A method of raising an immune response in a mammal comprising the step of administering to the mammal a polypeptide according to para 43 or an immunogenic composition according to para 46 or 47.

51. The method of claim 50 wherein the immune response protects or treats a disease and/or an infection caused by *Chlamydia.*

52. The polypeptide according to para 43 or the composition according to paras 46 or 47 for use as a diagnostic.

53. A method of diagnosing a *Chlamydia* infection in a patient comprising incubating T cell from the patient with a polypeptide as defined in para 43 or 46 or 47 and detecting the subsequent presence or absence of T-cell proliferation.

54. Use of a polypeptide according to para 43 or the composition according to paras 46 or 47 in the preparation of a medicament for use in the prevention or treatment of a bacterial infection, preferably a *Chlamydia* infection.

55. An protein or an immunogenic composition comprising SEQ ID Nos 14, 15, 16, 17, 18, 19, 20, 21, 22, 23, 24, 25, 26 and 27.

56. A protein or an immunogenic composition comprising SEQ ID No 185 wherein amino amino acid residue at position X1 is selected from the group consisting of Glycine (G) or Glutamic acid (E); amino acid at residue X2 is selected from the group consisting of Aspartic acid (D) or Glutamic acid (E) or Asparagine (N); amino acid at residue X3 is selected from the group consisting of Glycine (G) or Arginine (R); amino acid at residue X4 is selected from the group consisting of Threonine (T) or Alanine (A); amino acid at residue X5 is selected from the group consisting of Valine (V) or Isoleucine (I); amino acid at residue X6 is selected from the group consisting of Phenylalanine (F) or Leucine (L); amino acid at residue X7 is selected from the group consisting of Alanine (A) or Aspartic acid (D); amino acid at residue X8 is selected from the group consisting of Histidine (H) or Arginine (R); amino acid at residue X9 is selected from the group consisting of Asparagine (N) or Aspartic acid (D) and amino acid residue at position X10 is selected from the group consisting of Serine (S) or Proline (P) wherein the protein is not SEQ ID No 46.

57. The protein or the immunogenic composition according to para 56 for use according to any one of paras 16-27.

BRIEF DESCRIPTION OF THE DRAWINGS

The following invention will now be further described only by way of example in which reference is made to the following Figures. The following examples are presented only to illustrate the present invention and to assist one of ordinary skill in making and using the same. The examples are not intended in any way to otherwise limit the scope of the invention. Efforts have been made to ensure accuracy with respect to numbers used (e.g., amounts, temperatures, etc.), but some experimental error and deviation should, of course, be allowed for.

FIG. 1 shows the Amino acid sequence of LcrE alleles found in different clinical isolates of *C. trachomatis*. Sequences are compared to the reference sequence as reported in the fully sequenced genome of the serovar-D strain UW-3/Cx. Amino acid changes are therefore intended as compared to the reference serovar D sequence, arbitrarily identified as allele-1.

FIG. 2 shows the Alignment of the LcrE sequence from 14 *Chlamydia* isolates corresponding to 8 different *Chlamydia* serovars relative to the reference *Chlamydia* LcrE Serovar D (D/UW-3/CX) serovar. The "Majority" sequence at the top of each 30 mer alignment corresponds to a "consensus" sequence. In the event there are hypervariable regions with an equal number of substitutions (eg 7/14 substitutions at amino acid residues 64 and 162), then, this high frequency mutation point is indicated as an "asterisk=*" rather than an "either or" substitution.

FIG. 3 shows the Allelic variation of 6 genes in 14 *Chlamydia trachomatis* clinical isolates comprising 8 different serovars.

SEQ ID No 46=*Chlamydia trachomatis trachomatis* LcrE (CT089) Reference Sequence from Serovar D (D-UW-3/CX)

The non-mutated LcrE protein is disclosed as SEQ ID NO's: 61 & 62 in reference 17 {GenBank accession number: AAC67680, GI:3328485; 'CT089'; SEQ ID NO: 46 below}.

```
SEQ ID NO: 46
MTASGGAGGLGSTQTVDVARAQAAAATQDAQEVIGSQEASEASMLKGCE

DLINPAAATRIKKKGEKFESLEARRKPTADKAEKKSESTEEKGDTPLED

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP
```

(SEQ ID No 1) Genome: ATCC-E (8 Mutations: Allele-5)

The Genome ATCC-E (Serovar E) LcrE sequence (SEQ ID No 1) has 8 mutations relative to the Serovar D LcrE reference sequence (SEQ ID No 46). Genome ATCC-E is associated with Serovar E. The sequence of Genome ATCC-E is disclosed as SEQ ID NO: 1 (see below).

```
SEQ ID NO: 1:
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPEEILDALTSKFSDPTIKDLALDYLI
QTAPSDRKLKSALIQAKHQLMSQNPQAIVGGRNVLLASETFASRANTSPS
SLRSLYLQVTSSPSNCDNLRQMLASYLPSEKTAVMEFLVNGMVADLKSEG
PSIPPAKLQVYMTELSNLQALHSVDSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*
```

The alignment of Genome ATCC-E with the LcrE *Chlamydia trachomatis* antigen is as follows:

```
MTASGGAGGLGSTQTVDVARAQAAAATQDAQEVIGSQEASEASMLKGCE

DLINPAAATRIKKKGEKFESLEARRKPTADKAEKKSESTEEKGDTPLED
 .............E

RFTEDLSEVSGEDFRGLKNSFDDDSSPDEILDALTSKFSDPTIKDLALD
  .........................E

YLIQTAPSDGKLKSTLIQAKHQLMSQNPQAIVGGRNVLLASETFASRAN
   ......R....A

TSPSSLRSLYFQVTSSPSNCANLHQMLASYLPSEKTAVMEFLVNGMVAD
    .......L.........D..R

LKSEGPSIPPAKLQVYMTELSNLQALHSVNSFFDRNIGNLENSLKHEGH
     ........................D

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
```

(2) Genome: ATCC-F (no Mutations: Allele-1)

The Genome ATCC-F (Serovar F) LcrE sequence (SEQ ID No 2) has no mutations relative to the Serovar D LcrE reference sequence (SEQ ID No 46).

Genome ATCC-F is associated with Serovar F. The sequence of Genome ATCC-F is disclosed as SEQ ID NO: 2 (see below).

```
SEQ ID NO: 2:
MTASGGAGGLGSTQTVDVARAQAAAATQDAQEVIGSQEASEASMLKGCE

DLINPAAATRIKKKGEKFESLEARRKPTADKAEKKSESTEEKGDTPLED

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
```

(3) Genome: ATCC-G (no Mutations: Allele-1)

The Genome ATCC-G (Serovar G) LcrE has no mutations relative to the Serovar D LcrE reference sequence (SEQ ID No 46).

Genome ATCC-G is associated with Serovar G. The sequence of Genome ATCC-G is disclosed as SEQ ID NO: 3 (see below).

```
SEQ ID NO: 3:
MTASGGAGGLGSTQTVDVARAQAAAATQDAQEVIGSQEASEASMLKGCE

DLINPAAATRIKKKGEKFESLEARRKPTADKAEKKSESTEEKGDTPLED

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
```

(4) Genome: ATCC-H (3 Mutations: Allele-4)

The Genome ATCC-H LcrE sequence has 3 mutations relative to the Serovar D LcrE reference sequence (SEQ ID No 46). Genome ATCC-H is associated with Serovar H. The sequence of Genome ATCC-H is disclosed as SEQ ID NO: 4 (see below).

```
SEQ ID NO: 4:
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*
```

The alignment of Genome ATCC-H with the LcrE *Chlamydia trachomatis* antigen is as follows:

```
MTASGGAGGLGSTQTVDVARAQAAAATQDAQEVIGSQEASEASMLKGCE

DLINPAAATRIKKKGEKFESLEARRKPTADKAEKKSESTEEKGDTPLED
 .............E
```

-continued

```
RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN
   ...........A

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
          ...................P
```

(5) Genome: ATCC-I (no Mutations: Allele-1)

The Genome ATCC-I LcrE sequence has no mutations relative to the Serovar D LcrE reference sequence (SEQ ID No 46).

Genome ATCC-I is associated with Serovar I. The sequence of Genome ATCC-I is disclosed as SEQ ID NO: 5 (see below).

```
SEQ ID NO: 5:
MTASGGAGGLGSTQTVDVARAQAAAATQDAQEVIGSQEASEASMLKGCE

DLINPAAATRIKKKGEKFESLEARRKPTADKAEKKSESTEEKGDTPLED

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
```

(6) Genome: ATCC-J (3 Mutations: Allele-4, as Cev-5)

The Genome ATCC-J LcrE sequence has 3 mutations relative to the Serovar D LcrE reference sequence (SEQ ID No 46).

Genome ATCC-J is associated with Serovar J. The sequence of Genome ATCC-J is disclosed as SEQ ID NO: 6 (see below).

```
SEQ ID NO: 6:
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*
```

The alignment of Genome ATCC-J with the LcrE *Chlamydia trachomatis* antigen is as follows:

```
MTASGGAGGLGSTQTVDVARAQAAAATQDAQEVIGSQEASEASMLKGCE

DLINPAAATRIKKKGEKFESLEARRKPTADKAEKKSESTEEKGDTPLED
 .............E

RFTEDLSEVSGEDFRGLKNSFDDDSSPDEILDALTSKFSDPTIKDLALD
```

-continued

```
YLIQTAPSDGKLKSTLIQAKHQLMSQNPQAIVGGRNVLLASETFASRAN
    ...........A

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
         ..................P
```

(7) Genome: ATCC-K (no Mutations: Allele-1)

The Genome ATCC-I LcrE sequence has no mutations relative to the Serovar D LcrE reference sequence (SEQ ID No 46).

Genome ATCC-I is associated with Serovar I. The sequence of Genome ATCC-I is disclosed as SEQ ID NO: 7 (see below).

```
SEQ ID NO: 7:
MTASGGAGGLGSTQTVDVARAQAAAATQDAQEVIGSQEASEASMLKGCE

DLINPAAATRIKKKGEKFESLEARRKPTADKAEKKSESTEEKGDTPLED

RFTEDLSEVSGEDFRGLRNSFDDDSSPDEILDALTSKFSDPTIKDLALD

YLIQTAPSDGKLKSTLIQAKHQLMSQNPQAIVGGRNVLLASETFASRAN

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
```

(8) Genome: Cev-1, serJ (4 Mutations: Allele-3)

The Genome Cev-1 (Serovar J) sequence has 4 mutations relative to the Serovar D LcrE reference sequence (SEQ ID No 46).

Genome Cev-1 is associated with Serovar J. The sequence of Genome Cev-1 is disclosed as SEQ ID NO: 8 (see below).

```
                                     SEQ ID NO: 8:
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIIGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*
```

The alignment of Genome Cev-1 with the LcrE *Chlamydia trachomatis* antigen is as follows:

```
MTASGGAGGLGSTQTVDVARAQAAAATQDAQEVIGSQEASEASMLKGCE

DLINPAAATRIKKKGEKFESLEARRKPTADKAEKKSESTEEKGDTPLED
 .............E

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN
    ...........A................I
```

-continued

```
TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
         ..................P
```

(9) Genome: Cev-2, serG (no Mutations: Allele-1)

The Genome Cev-2 (Serovar G) sequence has no mutations relative to the Serovar D LcrE reference sequence (SEQ ID No 46).

Genome Cev-2 is associated with Serovar G. The sequence of Genome Cev-2 is disclosed as SEQ ID NO: 9 (see below).

SEQ ID NO: 9:
MTASGGAGGLGSTQTVDVARAQAAAATQDAQEVIGSQEASEASMLKGCE

DLINPAAATRIKKKGEKFESLEARRKPTADKAEKKSESTEEKGDTPLED

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALN*GCSPRIFSGAEKKQQLASVITNTLDAINADNEDYPKPGDFPR*

*SSFSSTPP*HAPVPQSEIPTSPTSTQPPSP*

(10) Genome: Cev-4, serH (no Mutations: Allele-1)

The Genome Cev-4 LcrE sequence has no mutations relative to the Serovar D LcrE reference sequence (SEQ ID No 46).

Genome Cev-4 is associated with Serovar H. The sequence of Genome Cev-4 is disclosed as SEQ ID NO: 10 (see below).

SEQ ID NO: 10:
MTASGGAGGLGSTQTVDVARAQAAAATQDAQEVIGSQEASEASMLKGCE

DLINPAAATRIKKKGEKFESLEARRKPTADKAEKKSESTEEKGDTPLED

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALN*GCSPRIFSGAEKKQQLASVITNTLDAINADNEDYPKPGDFPR*

*SSFSSTPP*HAPVPQSEIPTSPTSTQPPSP*

(11) Genome: Cev-5, serJ (3 Mutations: Allele-4)

The Genome Cev-5 sequence has 3 mutations relative to the Serovar D LcrE reference sequence (SEQ ID No 46).

Genome Cev-5 is associated with Serovar J. The sequence of Genome Cev-5 is disclosed as SEQ ID NO: 11 (see below).

SEQ ID NO: 11:
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSALIQAKHQLMSQNPQAIVGGRNVLLASETFASRANTSPS
SLRSLYFQVTSSPSNCANLRQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPPP*

The alignment of Genome Cev-5 with the LcrE *Chlamydia trachomatis* antigen is as follows:

MTASGGAGGLGSTQTVDVARAQAAAATQDAQEVIGSQEASEASMLKGCE

DLINPAAATRIKKKGEKFESLEARRKPTADKAEKKSESTEEKGDTPLED
..............E

RFTEDLSEVSGEDFRGLKNSFDDDSSPDEILDALTSKFSDPTIKDLALD

YLIQTAPSDGKLKSTLIQAKHQLMSQNPQAIVGGRNVLLASETFASRAN
............A

TSPSSLRSLYFQVTSSPSNCANLHQMLASYLPSEKTAVMEFLVNGMVAD

LKSEGPSIPPAKLQVYMTELSNLQALHSVNSFFDRNIGNLENSLKHEGH

APIPSLTTGNLTKTFLQLVEDKFPSSSKAQKALNELVGPDTGPQTEVLN

LFFRALNGCSPRIFSGAEKKQQLASVITNTLDAINADNEDYPKPGDFPR

SSFSSTPPHAPVPQSEIPTSPTSTQPPSP*
....................P

(12) Genome: Cev-8, serE (8 Mutations: Allele-5)

The Genome Cev-8 LcrE sequence has 8 mutations relative to the Serovar D LcrE reference sequence (SEQ ID No 46).

Genome Cev-8 is associated with Serovar E. The sequence of Genome Cev-8 is disclosed as SEQ ID NO: 12 (see below).

SEQ ID NO: 12:
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPEEILDALTSKFSDPTIKDLALDYLI
QTAPSDGKLKSALIQAKHQLMSQNPQAIVGGRNVLLASETFASRANTSPS
SLRSLYLQVTSSPSNCDNLRQMLASYLPSEKTAVMEFLVNGMVADLKSEG
PSIPPAKLQVYMTELSNLQALHSVDSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP*

The alignment of Genome Cev-8 with the LcrE *Chlamydia trachomatis* antigen is as follows:

MTASGGAGGLGSTQTVDVARAQAAAATQDAQEVIGSQEASEASMLKGCED

LINPAAATRIKKKGEKFESLEARRKPTADKAEKKSESTEEKGDTPLEDRF
..............E

TEDLSEVSGEDFRGLKNSFDDDSSPDEILDALTSKFSDPTIKDLALDYLI
........................E

QTAPSDGKLKSTLIQAKHQLMSQNPQAIVGGRNVLLASETFASRANTSPS
......R....A

SLRSLYFQVTSSPSNCANLHQMLASYLPSEKTAVMEFLVNGMVADLKSEG
......L.........D..R

PSIPPAKLQVYMTELSNLQALHSVNSFFDRNIGNLENSLKHEGHAPIPSL
........................D

TTGNLTKTFLQLVEDKFPSSSKAQKALNELVGPDTGPQTEVLNLFFRALN

GCSPRIFSGAEKKQQLASVITNTLDAINADNEDYPKPGDFPRSSFSSTPP

HAPVPQSEIPTSPTSTQPPSP*
....................P

(13) Genome: GO/86 serD (4 Mutations: Allele-2)

The Genome GO/86 LcrE sequence has 4 mutations (at position 64, 126, 162, and 420) relative to the Serovar D LcrE reference sequence (SEQ ID No 46).

Genome GO/86 is associated with Serovar D. The sequence of Genome GO/86 is disclosed as SEQ ID NO: 13 (see below).

SEQ ID NO: 13:
MTASGGAGGLGSTQTVDVARAQAAAATQDAQEVIGSQEASEASMLKGCED
LINPAAATRIKKKEEKFESLEARRKPTADKAEKKSESTEEKGDTPLEDRF
TEDLSEVSGEDFRGLKNSFDDDSSPNEILDALTSKFSDPTIKDLALDYLI
QTAPSDGKLKSALIQAKHQLMSQNPQAIVGGRNVLLASETFASRANTSPS
SLRSLYLQVTSSPSNCANLHQMLASYLPSEKTAVMEFLVNGMVADLKSEG
PSIPPAKLQVYMTELSNLQALHSVDSFFDRNIGNLENSLKHEGHAPIPSL
TTGNLTKTFLQLVEDKFPSSSKAQKALNELVGPDTGPQTEVLNLFFRALN
*GCSPRIFSGAEKKQQLASVITNTLDAINADNEDYPKPGDFPRSSF*
*SSTPP*HAPVPQSEIPTSPTSTQPPPP*

The alignment of Genome GO/86 with the LcrE *Chlamydia trachomatis* antigen is as follows:

Genome: GO/86 serD (4 Mutations: Allele-2)

MTASGGAGGLGSTQTVDVARAQAAAATQDAQEVIGSQEASEASMLKGCED

LINPAAATRIKKKGEKFESLEARRKPTADKAEKKSESTEEKGDTPLEDRF
..............E

TEDLSEVSGEDFRGLKNSFDDDSSPDEILDALTSKFSDPTIKDLALDYLI
........................N

QTAPSDGKLKSTLIQAKHQLMSQNPQAIVGGRNVLLASETFASRANTSPS
............A

SLRSLYFQVTSSPSNCANLHQMLASYLPSEKTAVMEFLVNGMVADLKSEG

PSIPPAKLQVYMTELSNLQALHSVNSFFDRNIGNLENSLKHEGHAPIPSL

TTGNLTKTFLQLVEDKFPSSSKAQKALNELVGPDTGPQTEVLNLFFRALN

GCSPRIFSGAEKKQQLASVITNTLDAINADNEDYPKPGDFPRSSFSSTPP

HAPVPQSEIPTSPTSTQPPSP*
....................P

Consensus Sequences (SEQ ID Nos 14-27)

The majority or consensus sequence of the LcrE *Chlamydia trachomatis* antigen was determined in 30 mer peptide segments.

The first segment of 30 amino acid residues of the consensus sequence (residues 1-30) is disclosed as SEQ ID NO: 14 as follows:

SEQ ID NO: 14
MTASGGAGGLGSTQTVDVARAQAAAATQDA

The second segment of 30 amino acid residues of the consensus sequence (residues 31-60) is disclosed as SEQ ID NO: 15 as follows:

SEQ ID NO: 15
QEVIGSQEASEASMLKGCEDLINPAAATRI

No mutations were identified in either SEQ ID NO: 14 or SEQ ID NO: 15 relative to the Serovar D LcrE reference sequence (SEQ ID No 46).

The third segment of 30 amino acid residues of the consensus sequence (residues 61-90) is disclosed as SEQ ID NO: 16 as follows:

SEQ ID NO: 16
KKKXEKFESLEARRKPTADKAEKKSESTEE

The amino acid residue at position 4 of SEQ ID NO: 16 is glutamic acid (E) in half of the observed isolates and glycine (G) in the other half of the observed isolates. Therefore, the amino acid residue at position 4 of the 61-90 residue segment of the consensus sequence for the LcrE antigen (i.e., residue 64 of the consensus sequence overall=high frequency mutation point) is marked as X here.

The fourth segment of 30 amino acid residues of the consensus sequence (residues 91-120) is disclosed as SEQ ID NO: 17 as follows:

SEQ ID NO: 17
KGDTPLEDRFTEDLSEVSGEDFRGLKNSFD

No mutations were observed in the isolates in the segment of the LcrE *Chlamydia trachomatis* antigen in the portion of the sequence from residue 91-120 relative to the Serovar D LcrE reference sequence (SEQ ID No 46).

The fifth segment of 30 amino acid residues of the consensus sequence (residues 121-150) is disclosed as SEQ ID NO: 18 as follows:

SEQ ID NO: 18
DDSSPDEILDALTSKFSDPTIKDLALDYLI

The amino acid residue at position 6 (overall residue=126) of the consensus sequence segment from residue 121-150 was aspartic acid in 10 of 13 of the isolates, glutamic acid in 2 of 13 of the isolates and asparagines in 1 of the 13 isolates.

The sixth segment of 30 amino acid residues of the consensus sequence (residues 151-180) is disclosed as SEQ ID NO: 19 as follows:

SEQ ID NO: 19
QTAPSDGKLKSXLIQAKHQLMSQNPQAIVG

The amino acid residue at position 12 (overall residue=162=high frequency mutation point) of SEQ ID NO: 19 was alanine (A) in half of the observed isolates and threonine (T) in the other half of the observed isolates. Therefore, the amino acid residue at position 12 of the 151-180 residue segment of the consensus sequence for the LcrE *Chlamydia trachomatis* antigen (i.e., residue 162 of the consensus sequence overall) is marked as X here.

The seventh segment of 30 amino acid residues of the consensus sequence (residues 181-210) is disclosed as SEQ ID NO: 20 as follows:

SEQ ID NO: 20
GRNVLLASETFASRANTSPSSLRSLYEQVT

The amino acid residue at position 27 (overall residue=207) of the consensus sequence segment from residue 181-210 was phenylalanine (F) in 12 of 14 isolates and leucine (L) in 2 of 14 isolates.

The eighth segment of 30 amino acid residues of the consensus sequence (residues 211-240) is disclosed as SEQ ID NO: 21 as follows:

SEQ ID NO: 21
SSPSNCANLHQMLASYLPSEKTAVMEFLVN

Two mutations were observed in the consensus sequence segment (SEQ ID No 21) from residue 211-240 at positions 217 and 220 of the overall consensus sequence.

The ninth segment of 30 amino acid residues of the consensus sequence (residues 241-270) is disclosed as SEQ ID NO: 22 as follows:

SEQ ID NO: 22
GMVADLKSEGPSIPPAKLQVYMTELSNLQA

No mutations were identified in SEQ ID NO: 22 relative to the Serovar D LcrE reference sequence (SEQ ID No 46).

The tenth segment of 30 amino acid residues of the consensus sequence (residues 271-300) is disclosed as SEQ ID NO: 23 as follows:

SEQ ID NO: 23
LHSVNSFFDRNIGNLENSLKHEGHAPIPSL

The amino acid residue at position 5 (overall residue=275) of the consensus sequence segment from residue 271-300 was asparagines (N) in 12 of 14 of the isolates and aspartic acid (D) in 2 of the 14 isolates.

The eleventh segment of 30 amino acid residues of the consensus sequence (residues 301-330) is disclosed as SEQ ID NO: 24 as follows:

SEQ ID NO: 24
TTGNLTKTFLQLVEDKFPSSSKAQKALNEL

The twelfth segment of 30 amino acid residues of the consensus sequence (residues 331-360) is disclosed as SEQ ID NO: 25 as follows:

SEQ ID NO: 25
VGPDTGPQTEVLNLFFRALNGCSPRIFSGA

The thirteenth segment of 30 amino acid residues of the consensus sequence (residues 361-390) is disclosed as SEQ ID NO: 26 as follows:

SEQ ID NO: 26
EKKQQLASVITNTLDAINADNEDYPKPGDF

No mutations were identified in either SEQ ID NO: 24, 25, or 26 relative to the Serovar D LcrE reference sequence (SEQ ID No 46).

The fourteenth segment of 30 amino acid residues of the consensus sequence (residues 391-420) is disclosed as SEQ ID NO: 27 as follows:

SEQ ID NO: 27

PRSSFSSTPPHAPVPQSEIPTSPTSTQPPS

The amino acid residue at position 30 of the consensus sequence segment from residue 391-420 (i.e., position 420 of the overall consensus sequence) was serine (S) in 9 of 14 isolates and was proline (P) in 5 of 14 isolates.

In all isolates observed, the amino acid residue at position 421 was proline.

The LcrE reference sequence from *Chlamydia trachomatis* Strain D/UW-3/CX is provided as SEQ ID NO: 28 (below) which also shows a summary of the all of the allelic mutation points detected in the various *Chlamydia trachomatis* serovar isolates: The underlined regions in SEQ ID No 28 surrounding the point mutations are likely to correspond with either B and/or T cell epitopic peptide regions.

SEQ ID NO: 28

MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSILIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP

SEQ ID NO: 185

MTASGGAGGLGSTQTVDVARAQAAAATQDAQEVIGSQEASEASMLKGCED
LINPAAATRIKKKX1EKFESLEARRKPTADKAEKKSESTEEKGDTPLEDRF
TEDLSEVSGEDFRGLKNSFDDDSSPX2EILDALTSKFSDPTIKDLALDYLI
QTAPSDX3KLKSX4LIQAKHQLMSQNPQAIX5GGRNVLLASETFASRANTS
PSSLRSLYX6QVTSSPSNCX7NLX8QMLASYLPSEKTAVMEFLVNGMVADL
KSEGPSIPPAKLQVYMTELSNLQALHSVX9SFFDRNIGNLENSLKHEGHAP
IPSLTTGNLTKTFLQLVEDKFPSSSKAQKALNELVGPDTGPQTEVLNLFFR
ALNGCSPRIFSGAEKKQQLASVITNTLDAINADNEDYPKPGDFPRSSFSST
PPHAPVPQSEIPTSPTSTQPPX10P

Table 2 shows 17 antigenic determinants (or epitopic peptides set out as SEQ ID Nos 29-45) for *Chlamydia trachomatis* trachomatis LcrE protein

| n | Start Position | Sequence | End Position | Seq ID NO: |
|---|---|---|---|---|
| 1 | 14 | QTVDVARAQAAAA | 26 | 29 |
| 2 | 29 | DAQEVIG | 35 | 30 |
| 3 | 44 | MLKGCEDLINP | 54 | 31 |
| 4 | 125 | PIDEILDALTS | 134 | 32 |
| 5 | 140 | TIKDLALDYLIQT | 152 | 33 |
| 6 | 159 | LKSILIQAKHQ | 169 | 34 |
| 7 | 180 | GGRNVLLASE | 189 | 35 |
| 8 | 198 | SPSSLRSLYFQVTSSPSNCANL HQMLASYLPSE | 230 | 36 |
| 9 | 233 | AVMEFLVNGMVAD | 245 | 37 |
| 10 | 250 | GPSIPPAKLQVYM | 262 | 38 |
| 11 | 265 | LSNLQALHSVNS | 276 | 39 |
| 12 | 293 | GHAPIPS | 299 | 40 |
| 13 | 306 | TKTFLQLVED | 315 | 41 |
| 14 | 326 | ALNELVGP | 333 | 42 |
| 15 | 337 | PQTEVLNLFFRALNGCSPRI | 356 | 43 |
| 16 | 362 | KKQQLASVIT | 371 | 44 |
| 17 | 395 | FSSTPPHAPVPQSEI | 409 | 45 |

DETAILED DESCRIPTION OF THE INVENTION

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., Molecular Cloning: A Laboratory Manual (2nd Edition, 1989); DNA Cloning: A Practical Approach, vol. I & II (D. Glover, ed.); Oligonucleotide Synthesis (N. Gait, ed., 1984); A Practical Guide to Molecular Cloning (1984); and Fundamental Virology, 2nd Edition, vol. I & II (B. N. Fields and D. M. Knipe, eds.).

All publications, patents and patent applications cited herein, whether supra or infra, are hereby incorporated by reference in their entirety. It must be noted that, as used in this specification and the appended claims, the singular forms "a", "an" and "the" include plural referents unless the content clearly dictates otherwise. All scientific and technical terms used in this application have meanings commonly used in the art unless otherwise specified. As used in this application, the following words or phrases have the meanings specified.

The term "comprising" means "including" as well as "consisting" e.g. a composition "comprising" X may consist exclusively of X or may include something additional e.g. X+Y.

The term "about" in relation to a numerical value x means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489

The one-letter amino acid symbols recommended by the IUPAC-IUB Biochemical Nomenclature Commission are provided below together with the three-letter codes which are also provided for reference purposes.

| | | |
|---|---|---|
| A | Ala | Alanine |
| C | Cys | Cysteine |
| D | Asp | Aspartic acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Unless otherwise noted, terminology used herein should be given its normal meaning as understood by one of skill in the art. In order to facilitate understanding of the present invention, a number of defined terms are used herein to designate particular elements of the present invention. When so used, the following meanings are intended:

As also noted above, in the course of evaluating the allelic variation for the LcrE gene in 14 *Chlamydia trachomatis* clinical isolates representative of 8 different *Chlamydia trachomatis* serovars, the Applicants established that a higher than expected number of single amino acidic substitutions across the *C. trachomatis* serovars was observed for the LcrE antigen relative to (i) a reference *Chlamydia trachomatis* LcrE sequence from Serovar D and (ii) those found for other immunogenic *Chlamydia trachomatis* antigens.

This highly unexpected and surprising finding suggests that:

(i) the LcrE protein may be subjected to a greater immunological pressure that other immunogenic *Chlamydia trachomatis* antigens; and (ii) the peptides surrounding the amino acid substitutions are likely to be epitopic regions (either B-cell epitopes involved in antibody-antigen (Ab-Ag) interactions and/or T-cell epitopes capable of eliciting *Chlamydia* specific cell mediated responses.

Applicants finding is all the more surprising because the *Chlamydia* isolates used for these genotyping studies came from two very divergent immunological sources which were isolated from two different Continents (North America and Europe) and over different time periods (minimum of 30 years ago versus 5-8 years ago).

Allelic Variant

As used herein, the term "allelic variant" refers to any one of a series of two or more different genes that occupy the same position (locus) on a chromosome. By way of example, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant may encode a protein having a similar biological activity but not necessarily the same immunological activity relative to that of the protein encoded by the gene to which it is being compared. As discussed below, the nature of the mutation or change in genotype may influence the resulting functional effect or change in biological and/or immunological phenotype. An allelic variant can also comprise an alteration in the 5' or 3' untranslated regions of the gene, such as in regulatory control regions (eg see U.S. Pat. No. 5,753,235).

Mutant

As used herein, the term "mutant" refers to a sequence which differs from a reference sequence by having one or more differences (mutations). This may be a substitution, a deletion, or an insertion. The mutant may or may not have a functional effect. By way of example, if one or more of the differences in allelic variants or mutants of the invention, compared to reference SEQ ID No 46 involves a conservative amino acid replacement, such as, for example, replacement of one amino acid with another which has a related side chain, then the mutated sequence may not demonstrate a functional biological effect relative to the reference sequence. In this respect, genetically-encoded amino acids are generally divided into four families: (1) acidic ie. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological or immunological activity.

On the other hand if if one or more of the differences in allelic variants or mutants of the invention, compared to reference SEQ ID No 46 involves a non-conservative amino acid replacement, then this replacement may have a functional effect resulting, for example in a change in phenotype, such as an altered immunogenicity for an antigen sequence, such as LcrE. By way of example, analysis of data from experimentally determined antigenic sites on proteins suggests that the hydrophobic residues Cys, Leu and Val, if they occur on the surface of a protein, are more likely to be part of antigenic sites (see Kolaskar and Tongaonkar (1990) FEBS Lett 276(1-2) 172-4). In relation to the ten mutations highlighted in SEQ ID No 28 and SEQ ID No 185 of the present invention, four mutations were viewed as "conservative" and six mutations were viewed as "non-conservative" (see for Example, Table 4 in Example 4). Given that there are conflicting views of the nature of a conservative or a non-conservative mutations (for example, difference in physical or chemical characteristics relative to the nature of the amino acid side chain versus various evolutionary criteria), Applicants have used the existence of high frequency mutations (eg at points 64 and 162 of the LcrE sequence) as one example of a useful marker for hypervariable regions within a sequence which are likely to be linked to the presence of T and/or B cell epitopic regions capable of eliciting an immunogenic response in a subject, such as a humoural and/or a cell-mediated immune response.

By way of further explanation, Applicants have identified two high frequency mutation points or hypervariable regions at amino acid residues 64 and 162 in the LcrE Serovar sequence. At amino acid residue 64, there are seven mutations from Glycine (G) to Glutamic (E) acid across the 14 *Chlamydia* isolates while at point 162, there are also seven mutations from Threonine (T) to Alanine (A) across the 14 *Chlamydia* isolates. The existence of two high frequency mutation points or hypervariable regions (eg at residues 64 and 162 of the reference sequence) is a highly surprising and unexpected finding and is likely to be associated with the presence of epitopic regions capable of eliciting an altered immunogenic response in a subject.

The LcrE reference sequence from *Chlamydia trachomatis* trachomatis Strain D/UW-3/CX is provided as SEQ ID NO:46 and SEQ ID No 28 and SEQ ID No 185. The latter sequence also provides a summary of the all of the allelic mutation points or allelic variants points detected in the various *Chlamydia trachomatis* serovar isolates: The underlined regions in SEQ ID No 28 and SEQ ID No 185 surrounding the point mutations are likely to correspond with either B and/or T cell epitopic peptide regions.

Epitopes

As used herein, the term "epitope" generally refers to the site on an antigen which is recognised by a T-cell receptor and/or an antibody. Preferably it is a short peptide derived from or as part of a protein antigen. However the term is also intended to include peptides with glycopeptides and carbohydrate epitopes. Several different epitopes may be carried by a single antigenic molecule. The term "epitope" also includes modified sequences of amino acids or carbohydrates which stimulate responses which recognise the whole organism. It is advantageous if the selected epitope is an epitope of an infectious agent, such as a *Chlamydia trachomatis* bacterium, which causes the infectious disease.

The epitope can be generated from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Kendrew, supra; Janis Kuby, Immunology, 1992 e.g., pp. 79-81. Some guidelines in determining whether a protein will stimulate a response, include: Peptide length—preferably the peptide is about 8 or 9 amino acids long to fit into the MHC class I complex and about 13-25 amino acids long to fit into a class II MHC complex. This length is a minimum for the peptide to bind to the MHC complex. It is preferred for the peptides to be longer than these lengths because cells may cut peptides. The peptide may contain an appropriate anchor motif which will enable it to bind to the various class I or class II molecules with high enough specificity to generate an immune response (See Bocchia, M. et al, Specific Binding of Leukemia Oncogene Fusion Protein Pentides to HLA Class I Molecules, Blood 85:2680-2684; Englehard, V H, Structure of peptides associated with class I and class II MHC molecules Ann. Rev. Immunol. 12:181 (1994)). This can be done, without undue experimentation, by comparing the sequence of the protein of interest with published structures of peptides associated with the MHC molecules. Thus, the skilled artisan can ascertain an epitope of interest by comparing the protein sequence with sequences listed in the protein database.

T Cell Epitopes

Preferably, the antigen of the invention, in particular, the LcrE antigen(s) of the present invention comprises one or more T cell epitopes.

As used herein, the term "T cell epitope" refers generally to those features of a peptide structure which are capable of inducing a T cell response. In this regard, it is accepted in the art that T cell epitopes comprise linear peptide determinants that assume extended conformations within the peptide-binding cleft of MHC molecules (Unanue et al. (1987) Science 236: 551-557).

As used herein, a T cell epitope is generally a peptide having at least about 3-5 amino acid residues, preferably at least 5-10 or more consecutive amino acid residues, preferably at least 8-10 amino consecutive acid residues, preferably at least 10-14 consecutive amino acid residues, more preferably at least 9 consecutive amino acid residues.

However, as used herein, the term "T cell epitope" encompasses any MHC Class I- or MHC Class II restricted peptide. The ability of a particular T cell epitope to stimulate/enhance or alter a CMI response may be determined by a number of well-known assays, such as by lymphoproliferation (lymphocyte activation) assays, CD8+ T-cell cytotoxic cell assays, or by assaying for T-lymphocytes specific for the epitope in a sensitized subject. See, e.g., Erickson et al. (1993) J. Immunol. 151: 4189-4199; and Doe et al. (1994) Eur. J. Immunol. 24: 2369-2376 or CD8+ T-cell ELISPOT assays for measuring Interferon gamma production (Miyahara et al PNAS (USA) (1998) 95: 3954-3959).

CD8+ T-Cell Epitopes.

Preferably the antigen of the invention, in particular the LcrE antigen(s) of the present invention comprise one or more CD8+ T-cell inducing epitopes. A CD8+ T-cell-inducing epitope is an epitope capable of stimulating the formation, or increasing the activity, or altering the activity of specific CD8+ T-cells following its administration to a host subject.

As used herein, a CD8+ T cell epitope is generally a peptide having at least about 3-5 amino acid residues, preferably at least 5-10 or more consecutive amino acid residues, preferably at least 8-10 consecutive amino acid residues, preferably at least 10-14 consecutive amino acid residues, more preferably at least 8 or at least 9 consecutive amino acid residues.

The CD8+ T-cell epitopes may be provided in a variety of different forms such as a recombinant string of one or two or more epitopes. CD8+ T-cell epitopes have been identified and can be found in the literature, for many different diseases. It is possible to design epitope strings to generate CD8+ T-cell response against any chosen antigen that contains such CD8+ T-cell epitopes. Advantageously, CD8+ T-cell inducing epitopes may be provided in a string of multiple epitopes which are linked together without intervening sequences so that unnecessary nucleic acid material is avoided.

T Helper Epitopes

Preferably the LcrE antigen(s) of the present invention comprise one or more helper T lymphocyte epitopes. Various methods are available to identify T helper cell epitopes suitable for use in accordance herewith. For example, the amphipathicity of a peptide sequence is known to affect its ability to function as a T helper cell inducer. A full discussion of T helper cell-inducing epitopes is given in U.S. Pat. No. 5,128,319, incorporated herein by reference and in further discussion below.

As used herein, a helper (or CD4+) T cell epitope is generally a peptide having at least about 3-5 amino acid residues, preferably at least 5-10 or more consecutive amino acid residues, preferably at least 8-10 amino acid residues, preferably at least 9 consecutive amino acid residues. More preferably at least 10-14 consecutive amino acid residues.

Combination of Epitopes

Preferably the antigen of the invention, in particular, the LcrE antigen(s) of the present invention comprise a mixture of CD8+ T-cell epitopes and B cell epitopes. As used herein, the term "B cell epitope" generally refers to the site on an antigen to which a specific antibody molecule binds.

As used herein, a B cell epitope is generally a peptide having at least about 3-5 consecutive amino acid residues, preferably at least 5-10 or more consecutive amino acid residues, preferably at least 8-10 consecutive amino acid residues, preferably at least 10-14 consecutive amino acid residues, more preferably at least 8 or at least 9 consecutive amino acid residues.

The identification of epitopes which are able to elicit an antibody response is readily accomplished using techniques well known in the art. See, e.g., Geysen et al. (1984) Proc. Natl. Acad. Sci. USA 81: 3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) Molecular Immunology 23: 709-715 (technique for identifying peptides with high affinity for a given antibody)

In a preferred embodiment of the present invention, the antigen of the invention, in particular, the LcrE antigen or LcrE antigen combination of the invention, comprises a mixture of a CD8+ T-cell-inducing epitopes and a T helper cell-inducing epitopes. As is well known in the art, T and B cell inducing epitopes are frequently distinct from each other and can comprise different peptide sequences. Therefore certain regions of a protein's peptide chain can possess either T cell or B cell epitopes. Therefore, in addition to the CD8+ T-cell epitopes, it may be preferable to include one or more epitopes recognised by T helper cells, to augment the immune response generated by the CD8+ T-cell epitopes.

Immunodominant Epitope

When an individual is immunized with an antigen or combination of antigens or nucleotide sequence or combinations of nucleotide sequences encoding multiple epitopes of a target antigen, in many instances the majority of responding T lymphocytes will be specific for one or more linear epitopes from that target antigen and/or a majority of the responding B lymphocytes will be specific for one or more linear or conformational epitopes for the antigen or combination of antigens. For the purposes of the present invention, then, such epitopes are referred to as "immunodominant epitopes". In an antigen having several immunodominant epitopes, a single epitope may be the most dominant in terms of commanding a specific T and/or B cell response.

Peptides Comprising T-Cell and/or B Cell Epitopes of the Invention

The invention provides polypeptides comprising an amino acid sequence selected from the group consisting of SEQ ID Nos 1-184.

The polypeptide is preferably less than 80 amino acids in length (e.g. less than 75, 70, 65, 60, 55, 50, 45, 40, 35, 30, 29, 28, 27, 26, 25, 24, 23, 22, 21, 20, 19, 18, 17, 16, 15, 14, 13, 12, 11, 10 etc.)

Some of the cell epitopes of the invention (eg SEQ ID Nos 181, 182, 183 and 184) have been identified as 9 mers, but it is well-known that shorter peptides can interact with HLA molecules with high affinity and so the invention also provides a polypeptide comprising at least a 7 or 8 amino acid fragment of an amino acid sequence selected from the group consisting of SEQ IDs 1-184. The polypeptide is preferably less than 80 amino acids in length (e.g. less than 75, 70, 65, 60, 55, 50, 45, 40, 35, 30, 29, 28, 27, 26, 25, 24, 23, 22, 21, 20, 19, 18, 17, 16, 15, 14, 13, 12, 11 etc.). There are, for example, at least two 7 mer fragments and at least one 8mer fragments set out in Table 2.

If desired, these 7 mer and 8 mer sequences can be used according to the invention.

Similarly, there are at least three 10 mer fragments set out in Table 2. If desired, 10 mer fragments can be used according to the invention.

Preferably the invention provides polypeptides comprising amino acid sequences selected from the group consisting of SEQ ID Nos 29-45.

Preferably the invention provides polypeptides comprising amino acid sequence selected from the group consisting of SEQ ID Nos 47-98.

Preferably, the invention provides polypeptides comprising amino acid sequence selected from the group consisting of SEQ ID Nos 99-184.

More preferably, the invention provides polypeptides comprising amino acid sequence selected from the group consisting of SEQ ID Nos 54, 109, 110 and 111.

Even more preferably the polypeptide comprises the sequence IKKKGEKFE (SEQ ID No 181) or IKKKEEKFE (SEQ ID No 182).

These 9 mer and 15 mer polypeptides are particularly advantageous as they comprise the N-terminal segment surrounding or associated with the first high frequency mutation point or hypervariable regions at residues 64 of the LcrE sequence from Serovar D (SEQ ID No 54) and from Serovar E (SEQ ID Nos 109, 110 and 111) and equivalent regions in other Serovar isolates as seen in the Serovar Sequence Alignment in FIG. 2.

More preferably, the invention provides polypeptides comprising amino acid sequence selected from the group consisting of SEQ ID Nos 66, 129 and 130.

Even more preferably the polypeptide comprises the sequence KLKSTLIQA (SEQ ID No 183) or KLKSALIQA (SEQ ID No 184).

These 9 mer or 15 mer polypeptides are particularly advantageous as they comprise the hypervariable regions at residues 162 of the LcrE sequence from Serovar D (SEQ ID No 66) and from Serovar E (SEQ ID Nos 129 and 130) and equivalent regions in other Serovar isolates as seen in the Serovar Sequence Alignment in FIG. 2.

Th1Th2 Immune Responses

As noted above, the peptides surrounding the amino acid substitutions in antigen sequences of the invention, such as the LcrE sequence, are likely to be epitopic regions (either B-cell epitopes involved in Ab-Ag interactions and/or T-cell epitopes capable of eliciting *Chlamydia trachomatis* specific cell mediated immune responses, such as Th1 or Th2 cellular immune response. Preferably, the B-cell epitopes and/or the T-cell epitopes associated with these regions elicit an enhanced immune response either alone or in combination with other antigens and/or immunoregulatory agents.

As *Chlamydia trachomatis* infection is an intracellular infection, one of the currently accepted paradigms is that effective anti-Chlamydial immunisation would require both an adequate T-cell response and high serum levels of neutralising antibodies and that "an ideal vaccine should induce long lasting (neutralising) antibodies and a cell mediated immunity that can quickly respond upon exposure to *Chlamydia trachomatis*". Several sometimes contradictory studies have indicated that both CD4+ and CD 8 positive T cells have a role in *Chlamydia* clearance (Loomis and Starnback (2002) Curr Opin Microbiol 5: 87-91). Indeed, there now appears to be a prevailing consensus that specific CD4+ T cells and B cells are critical to the complete clearance of intracellular *Chlamydia trachomatis* and for mediating recall immunity to *Chlamydia trachomatis* infection (see Igietseme, Black and Caldwell (2002) Biodrugs 16: 19-35 and Igietseme et al (1999) Immunology 98: 510-519); However, even more recently, evidence has been advanced that a T cell vaccine could also be feasible, such as, for example, an immunogenic composition comprising one or more T cell epitopes (see for example, Webster et al (2005) PNAS 102 (13) 4836-4841).

T Cell

The invention provides T cells which can bind to a T-cell epitope of the invention.

As used herein, term "T-cell" refers to lymphocyte cells which mature in the thymus and which express CD3 and a T-cell receptor. It includes naive cells, memory cells and effector cells.

The population of cells generated from T-cells which bind specifically to epitopes of the invention and which are activated by this interaction will be of two types: effector cells and memory cells. Effector cells are activated by epitopes of the invention to produce cytokines and kill infected cells. A proportion of effector cells can survive as memory cells. Memory cells are longer-lived and can be induced to generate new effector cell populations when the epitope is re-encountered, either by re-administration of epitopes of the invention or by infection by *Chlamydia*. The generation of memory and effector T-cell populations specific for epitopes of the invention may require the participation of helper T-cells which provide factors necessary for their growth and differentiation (e.g. cytokines, such as interleukin-2). The activation of helper T-cells can be achieved through a number of standard approaches. For example the epitope of invention may be joined to one Or more helper T-cell epitopes or a helper T-cell epitopes could be co-delivered (e.g. by a nucleic acid vector).

Two types of T cells, helper T cells (or CD4+ cells) and cytotoxic (or CD8+cells), are generally thought necessary to initiate and/or enhance cell mediated immunity and humoral immunity. Cytotoxic T-cells express a CD8 co-receptor and are commonly referred to as Cytotoxic T lymphocytes (CTLs) or CD8+ cells. Cytotoxic T-cells have a T-cell receptor which recognises a T-cell epitope when it is presented by a target cell in the context of a class I MHC protein thus resulting in the the lysis of a target cell which displays a T-cell epitope of the invention within a class I MHC molecule. The cytotoxic T-cell may be located in vitro or in vivo. Transfer of such a T-cell into a host may be used to transfer immunity ("adoptive immunotherapy"). Various methods can be used for obtaining and/or detecting T-cells of the invention.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-gamma, and TNF-beta. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An immune response may include one or more of an TH1 immune response and a TH2 immune response.

A TH1 immune response may include one or more of an increase in CTLs, an increase in one or more of the cytokines associated with a TH1 immune response (such as IL-2, IFN-gamma, and TNF-beta), an increase in activated macrophages, an increase in NK activity, or an increase in the production of IgG2a. Preferably, the enhanced TH1 immune response will include an increase in IgG2a production.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

The mechanism of eliciting a CD8+ T-cell induced response in vivo by T helper cell inducing agents is not completely clear. However, without being bound by theory, it is likely that the immune activating agent, by virtue of its ability to induce T helper cells, will result in increased levels of necessary cytokines that assist in the clonal expansion and dissemination of specific CD8+ T-cells. Regardless of the underlying mechanism, it is envisioned that the use of mixtures of helper T cell and CD8+ T-cell-inducing antigen combinations of the present invention will assist in eliciting the CM response. Particularly suitable T helper cell epitopes are those which are active in individuals of different HLA types, for example T helper epitopes from tetanus (against which most individuals will already be primed). It may also be useful to include B cell epitopes for stimulating B cell responses and antibody production. Synthetic nucleotide sequences may also be constructed to produce two types of immune responses: T cell only and T cell combined with a B cell response.

Immunogenic compositions or the invention, in particular, immunogenic composition comprising one or more LcrE antigen(s) of the present invention may be used either alone or in combination with other LcrE antigen(s) and/or other *Chlamydia* antigens or other antigens associated with a sexually transmissible disease (STD) optionally with an immunoregulatory agent capable of eliciting a Th1 and/or Th2 response.

The invention also comprises an immunogenic composition comprising one or more immunoregulatory agent, such as a mineral salt, such as an aluminum salt and an oligonucleotide containing a CpG motif. Most preferably, the immunogenic composition includes both an aluminum salt and an oligonucleotide containing a CpG motif. Alternatively, the immunogenic composition includes an ADP ribosylating toxin, such as a detoxified ADP ribosylating toxin and an oligonucleotide containing a CpG motif. Preferably, one or more of the immunoregulatory agents include an adjuvant. The adjuvant may be selected from one or more of the group consisting of a TH1 adjuvant and TH2 adjuvant, further discussed below. The adjuvant may be selected from the group consisting The compositions of the invention will preferably elicit both a cell mediated immune response as well as a Immoral immune response in order to effectively address a *Chlamydia trachomatis* intracellular infection. This immune response will preferably induce long lasting (eg neutralising) antibodies and a cell mediated immunity that can quickly respond upon exposure to *Chlamydia trachomatis.*

As discussed further in the Examples, the use of the combination of a mineral salt, such as an aluminum salt, and an oligonucleotide containing a CpG motif can provide for an enhanced immune response. The achievement of an improved immune response using such a combination of immunoregulatory agents is wholly unexpected and could not be predicted from the use of either agent alone; The invention therefore includes an oligonucleotide containing a CpG motif, a mineral salt such as an aluminum salt, and an antigen associated with a sexually transmissible disease (STD), such as a *Chlamydia trachomatis* antigen, such as an LcrE antigen. Further examples of *Chlamydia* antigens, such as but not limited to CT242, CT381, CT396, CT398 and/or CT045 and/or an antigen associated with a sexually transmissible disease (STD) are discussed further below and in the Examples.

The invention also provides a composition or the invention for use as a medicament. The medicament is preferably able to raise an immune response in a mammal (i.e. it is an immunogenic composition) and is more preferably a vaccine. The invention also provides the use of the compositions of the invention in the manufacture of a medicament for raising an immune response in a mammal. The medicament is preferably a vaccine.

The immune response may be one or both of a TH1 immune response and a TH2 response. Preferably, immune response provides for one or both of an enhanced TH1 response and an enhanced TH2 response.

The immune response may be an improved or an enhanced or an altered immune response.

The immune response may be one or both of a systemic and a mucosal immune response. Preferably, the immune response provides for one or both of an enhanced or altered systemic and an enhanced or altered mucosal immune response. Preferably the mucosal immune response is a TH2 immune response. Preferably, the mucosal immune response includes an increase in the production of IgA.

The invention also provides for a kit comprising a first component comprising a combination of *Chlamydia trachomatis* antigens, in particular an LcrE antigen. The combination of *Chlamydia trachomatis* antigens may be one or more of the immunogenic compositions of the invention. The kit may further include a second component comprising one or more of the following: instructions, syringe or other delivery device, adjuvant, or pharmaceutically acceptable formulating solution.

The invention also provides a delivery device pre-filled with the immunogenic compositions of the invention.

The invention also provides a method for raising an immune response in a mammal comprising the step of administering an effective amount of a composition of the invention. The immune response is preferably protective and preferably involves antibodies and/or cell-mediated immunity. Preferably, the immune response includes one or both of a TH1 immune response and a TH2 immune response. The method may raise a booster response.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. Preferably, the human is a teenager. More preferably, the human is a pre-adolescent teenager. Even more preferably, the human is a pre-adolescent female or male. Preferably the pre-adolescent male or female is around 9-12 years of age. Preferably the adolescent male or female is around 15-19 years of age. Preferably the male or female is around 20-49 years of age. Preferably the male or female is over 49 years of age. Preferably the target patient profile is selected from the group consisting of homosexuals and sex workers (eg prostitutes).

Tests to Determine the Efficacy of the Immune Response

One way of assessing the immunogenicity of the component proteins of the immunogenic compositions of the present invention is to express the proteins recombinantly and to screen patient sera or mucosal secretions by immunoblot. A positive reaction between the protein and the patient serum indicates that the patient has previously mounted an immune response to the protein in question—that is, the protein is an immunogen. This method may also be used to identify immunodominant proteins and/or epitopes.

Another way of checking efficacy of therapeutic treatment involves monitoring *C. trachomatis* infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the *Chlamydia trachomatis* antigens in the compositions of the invention after administration of the composition. Typically, serum *Chlamydia trachomatis* specific antibody responses are determined post-immunisation but pre-challenge whereas mucosal *Chlamydia trachomatis* specific antibody body responses are determined post-immunisation and post-challenge.

These uses and methods are preferably for the prevention and/or treatment of a disease caused by a *Chlamydia trachomatis* (e.g. trachoma, pelvic inflammatory disease, epididymitis, infant pneumonia, etc.). The compositions may also be effective against *C. pneumoniae.*

The vaccine compositions of the present invention can be evaluated in in vitro and in vivo animal models prior to host, e.g., human, administration. For example, in vitro neutralization by Peterson et al (1988) is suitable for testing vaccine compositions directed toward *Chlamydia trachomatis.*

One example of such an in vitro test is described as follows. Hyper-immune antisera is diluted in PBS containing 5% guinea pig serum, as a complement source. *Chlamydia trachomatis* ($10^4$ IFU; inclusion forming units) are added to the antisera dilutions. The antigen-antibody mixtures are incubated at 37° C. for 45 minutes and inoculated into duplicate confluent Hep-2 or HeLa cell monolayers contained in glass vials (e.g., 15 by 45 mm), which have been washed twice with PBS prior to inoculation. The monolayer cells are infected by centrifugation at 1000×g for 1 hour followed by stationary incubation at 37° C. for 1 hour. Infected monolayers are incubated for 48 or 72 hours, fixed and stained with *Chlamydia trachomatis* specific antibody, such as anti-MOMP. Inclusion-bearing cells are counted in ten fields at a magnification of 200×. Neutralization titer is assigned on the dilution that gives 50% inhibition as compared to control monolayers/IFU.

The efficacy of immunogenic compositions of the invention can also be determined in vivo by challenging animal models of *Chlamydia trachomatis* infection, e.g., guinea pigs or mice, with the immunogenic compositions. The immunogenic compositions may or may not be derived from the same serovars as the challenge serovars. Preferably the immunnogenic compositions are derivable from the same serovars as the challenge serovars. More preferably, the immunogenic composition and/or the challenge serovar are derivable from the group of genital tract serovars consisting of D, E, F, H, I and K and/or combinations thereof. Even more preferably, the immunogenic composition and/or the challenge serovar are derivable from the group of genital tract serovars consisting of D, E, F and I. Even more preferably, the immunogenic composition and/or the challenge serovar are derivable from the group of genital tract serovars consisting of D, E and F. In women, the serotypes D and F have been associated with asymptomatic infection while serotype E has been associated with both symptomatic and asymptomatic infection. Other possible serovar generally associated with male infections include LGV serovars. The serovars of the present invention are obtainable from clinical isolates or from culture collections such as the American Tissue Culture Collection (ATCC).

In vivo efficacy models include, but are not limited to: (i) A murine infection model using human *Chlamydia trachomatis* serotypes, such as serotypes D, E, F, H, I and K; (ii) a murine disease model which is a murine model using a mouse-adapted *Chlamydia trachomatis* strain, such as the *Chlamydia trachomatis* mouse pneumonitis (MoPn) strain also known as *Chlamydia muridarum*; and (iii) a primate model using human *Chlamydia trachomatis* isolates. The MoPn strain is a mouse pathogen while human *Chlamydia trachomatis* serotypes, such as serotypes D, E, F, H, I and K are human pathogens (see for example, Brunham et al (2000) J Infect Dis 181 (Suppl 3) S538-S543; Murdin et al (2000) J Infect Dis 181 (Suppl 3) S544-S551 and Read et at (2000) NAR 28(6); 1397-1406). As the Examples demonstrate, human *Chlamydia trachomatis* serotypes, such as serovar D can be used in mouse models although they normally require high inocula or pretreatment with progesterone. Progesterone is generally used because it seems to render the genital epithelium more susceptible to chlamydial infection (see Pal et al 2003 Vaccine 21: 1455-1465). One the other hand, MoPn, which was originally isolated from mouse tissues, is thought to be a natural murine pathogen and thus offers an evolutionarily adapted pathogen for analysis of host-pathogen interactions. Although the MoPn serovar is thought to have a high degree of DNA homology to the human *Chlamydia* serovars, it may also have some unique properties (see for example, Pal et al (2002) Infection and Immunity 70(9); 4812-4817.

By way of example, in vivo vaccine compositions challenge studies can be performed in the murine model of *Chlamydia trachomatis* (Morrison et al 1995). A description of one example of this type of approach is as follows. Female mice 7 to 12 weeks of age receive 2.5 mg of depoprovera subcutaneously at 10 and 3 days before vaginal infection. Post-vaccination, mice are infected in the genital tract with 1,500 inclusion-forming units of *Chlamydia trachomatis* contained in 5 ml of sucrose-phosphate-glutamate buffer, pH 7.4. The course of infection is monitored by determining, the percentage of inclusion-bearing cells by indirect immunofluorescence with *Chlamydia trachomatis* specific antisera, or by a Giemsa-stained smear from a scraping from the genital tract of an infected mouse. The presence of antibody titers in the serum of a mouse is determined by an enzyme-linked immunosorbent assay. The immunogenic compositions of the present invention can be administered using a number of different immunization routes such as but not limited to intramuscularly (i.m.), intra-peritoneal (i.p.), intra-nasal (i.n.), sub-cutaneous (s.c) or transcutaneous (t.c) routes. Generally, any route of administration can be used provided that the desired immune response at the required mucosal surface or surfaces is achieved. Likewise, the challenge serovars may be administered by a number of different routes. Typically, the challenge serovars are administered mucosally, such as but not limited to genital challenge or intra-nasal (i.n) challenge.

Alternative in-vivo efficacy models include guinea pig models. For example, in vivo vaccine composition challenge studies in the guinea pig model of *Chlamydia trachomatis* infection can be performed. A description of one example of this type of approach follows. Female guinea pigs weighing 450-500 g are housed in an environmentally controlled room with a 12 hour light-dark cycle and immunized with vaccine compositions via a variety of immunization routes. Post-vaccination, guinea pigs are infected in the genital tract with the agent of guinea pig inclusion conjunctivitis (GPIC), which has been grown in HeLa or McCoy cells (Rank et al. (1988)). Each animal receives approximately $1.4\times10^7$ inclusion forming units (IFU) contained in 0.05 ml of sucrose-phosphate-glutamate buffer, pH 7.4 (Schacter, 1980). The course of infection monitored by determining the percentage of inclusion-bearing cells by indirect immunofluorescence with GPIC specific antisera, or by Giemsa-stained smear from a scraping from the genital tract (Rank et al 1988). Antibody titers in the serum is determined by an enzyme-linked immunosorbent assay.

Alternatively, in vivo vaccine compositions challenge studies can be performed in the murine model of *Chlamydia trachomatis* (Morrison et al 1995). A description of one example of this type of approach is as follows. Female mice 7 to 12 weeks of age receive 2.5 mg of depoprovera subcutaneously at 10 and 3 days before vaginal infection. Post-vaccination, mice are infected in the genital tract with 1,500 inclusion-forming units of *Chlamydia trachomatis* contained in 5 ml of sucrose-phosphate-glutamate buffer, pH 7.4. The course of infection is monitored by determining the percentage of inclusion-bearing cells by indirect immunofluorescence with *Chlamydia trachomatis* specific antisera, or by a Giemsa-stained smear from a scraping from the genital tract of an infected mouse. The presence of antibody titers in the serum of a mouse is determined by an enzyme-linked immunosorbent assay.

Epitope Mapping

Epitope mapping of serovar variants, such as, but not limited to the LcrE serovar variants is carried out as follows: A mouse model of genital tract infection as described in WO 05/002619 is used. All the servoar variants, such as the LcrE variants, are expressed as recombinant proteins, methodology for which is also described in WO 05/002619. Mice are immunised with the recombinant LcrE variants (with and without *Chlamydia trachomatis* challenge). The spleen cells from immunised mice (with and without *Chlamydia trachomatis* challenge) are then isolated and pulsed with CT LcrE specific peptides (as set out in SEQ ID Nos 29-45 in Example 2, SEQ ID Nos 47-98 in Example 3 and SEQ ID Nos 99-180, 181, 182, 183 and/or 184 in Example 4). The spleen cell response to each of the CT LcrE specific peptides is then assessed in terms of the presence or absence of spleen cell proliferation, mediator response such as, for eg, Th1 or Th2 cell response as determined by various tests described above.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc.

*Chlamydia* infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Immunogenic compositions used as vaccines comprise an immunologically effective amount of antigen(s), as well as any other components, as needed. By ‘immunologically effective amount’, it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual’s immune system to synthesise antibodies, the degree of protection desired, the formulation of the vaccine, the treating doctor’s assessment of the medical situation, and other relevant factors. It is expected that the amount will fall in a relatively broad range that can be determined through routine trials.

Further Components of the Composition

The composition of the invention will typically, in addition to the components mentioned above, comprise one or more ‘pharmaceutically acceptable carriers’, which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in reference 18.

ImmunoRegulatory Agents

Vaccines of the present invention may be administered in conjunction with other immunoregulatory agents. In particular, compositions will usually include an adjuvant. Adjuvants for use with the invention include, but are not limited to, one or more of the following set forth below:

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

Preferably the adjuvant is alum, preferably AlOH.

B. Oil-Emulsions

Oil-emulsion compositions suitable for use as adjuvants in the invention include squalene-water emulsions, such as MF59 (5% Squalene, 0.5% Tween 80, and 0.5% Span 85, formulated into submicron particles using a microfluidizer). See WO90/14837. See also, Frey et al., “Comparison of the safety, tolerability, and immunogenicity of a MF59-adjuvanted influenza vaccine and a non-adjuvanted influenza vaccine in non-elderly adults”, Vaccine (2003) 21:4234-4237. MF59 is used as the adjuvant in the FLUAD™ influenza virus trivalent subunit vaccine.

Particularly preferred adjuvants for use in the compositions are submicron oil-in water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphophoryloxy)-ethylamine (MTP-PE), for example, the submicron oil-in-water emulsion known as “MF59” (International Publication No. WO90/14837; U.S. Pat. Nos. 6,299,884 and 6,451,325, incorporated herein by reference in their entireties; and Ott et al., “MF59—Design and Evaluation of a Safe and Potent Adjuvant for Human Vaccines” in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term “MF59-0” refers to the above submicron oil-in-water emulsion lacking MTP-PE, while the term MF59-MTP denotes a formulation that contains MTP-PE. For instance, “MF59-100” contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325, incorporated herein by reference in their entireties. Complete Freund’s adjuvant (CFA) and incomplete Freund’s adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-LC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexs (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of additional detergent. See WO00/07621.

A review of the development of saponin based adjuvants can be found at Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 L1 Healthy Volunteers Immunized with Recombinant HPV-16 L1 Virus-Like Particles", Journal of Infectious Diseases (2003) 188:327-338; and Gerber et al., "Human Papillomavrisu Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRW) are used as the subunit antigen delivery system in the intranasal trivalent INFLEXAL™ product {Mischler & Metcalfe (2002) *Vaccine* 20 Suppl 5:B17-23} and the INFLUVAC PLUS™ product.

E. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid. A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of Plasmodium berghei", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31(part 3):664-658; Bhagat et al., "CpG penta- and hexadeoxyribonucleotides as potent immunomodulatory agents" BBRC (2003) 300:853-861 and WO03/035836.

Preferably the adjuvant is CpG. Even more preferably, the adjuvant is Alum and CpG or AlOH and CpG.

(4) ADP-Ribosylating Toxins and Detoxified Derivatives Thereof.

Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivaties thereof, particularly LT-K63 and LT-R72, as adjuvants can be found in the following references, each of which is specifically incorporated by reference herein in their entirety: Beignon, et al., "The LTR72 Mutant of Heat-Labile Enterotoxin of *Escherichia coli* Enhances the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9): 5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12): 6270-6280; Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol (1995) 15(6): 1165-1167, specifically incorporated herein by reference in its entirety.

Preferably the adjuvant is LTK63. Preferably the adjuvant is LTK72.

F. Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Rele.* 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention. E.g. WO99/27960.

G. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-l-alanyl-d-isoglutamine (nor-MDP), and N-acetylmuramyl-l-alanyl-d-isoglutaminyl-l-alanine-2-(1'-2'-dipalmitoyl-sn-glycero-3-hydroxyphosphoryloxy)-ethylamine MTP-PE).

L. Imidazoquinolone Compounds.

Examples of imidazoquinolone compounds suitable for use adjuvants in the invention include Imiquamod and its homologues, described further in Stanley, "Imiquimod and the imidazoquinolones: mechanism of action and therapeutic potential" Clin Exp Dermatol (2002) 27(7):571-577 and Jones, "Resiquimod 3M", Curr Opin Investig Drugs (2003) 4(2):214-218.

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g. QS21)+3dMPL+IL-12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% Tween 80, 5% pluronic-block polymer L121, and thr-MDP, either microfluidized into a submicron emulsion or vortexed to generate a larger particle size emulsion.

(7) Ribi™ adjuvant system (RAS), (Bibi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dPML).

Aluminum salts and MF59 are preferred adjuvants for use with injectable influenza vaccines. Bacterial toxins and bioadhesives are preferred adjuvants for use with mucosally-delivered vaccines, such as nasal vaccines.

M. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Fusion Proteins

The *Chlamydia trachomatis* antigens used in the invention may be present in the composition as individual separate polypeptides. Generally, the recombinant fusion proteins of the present invention are prepared as a GST-fusion protein and/or a His-tagged fusion protein.

However, preferably, at least two (i.e. 2, 3, 4, 5, 6, 7, 8, 9, 10, 11, 12, 13, 14, 15, 16, 17, 18, 19 or 20) of the antigens are expressed as a single polypeptide chain (a 'hybrid' polypeptide). Hybrid polypeptides offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

In the context of the following discussions, reference will be made to Serovar E as a first serovar group, Serovar D as a second serovar group, Serovar K as a third serovar group, Serovar F as a fourth serovar group, Serovar G as a fifth serovar group, Serovar H as a sixth serovar group, Serovar I as a seventh serovar group, and Serovar J as an eight serovar group.

The hybrid polypeptide may comprise two or more polypeptide sequences from the first serovar group. Accordingly, the invention includes a composition comprising a first amino acid sequence and a second amino acid sequence, wherein said first and second amino acid sequences are selected from a *Chlamydia trachomatis* antigen or a fragment thereof, such as an LcrE antigen, of the first serovar group. Preferably, the first and second amino acid sequences in the hybrid polypeptide comprise different epitopes.

The hybrid polypeptide may comprise two or more polypeptide sequences from the second serovar group. Accordingly, the invention includes a composition comprising a first amino acid sequence and a second amino acid sequence, wherein said first and second amino acid sequences are selected from a *Chlamydia trachomatis* antigen or a fragment thereof, such as the LcrE antigen, of the second serovar group. Preferably, the first and second amino acid sequences in the hybrid polypeptide comprise difference epitopes.

The hybrid polypeptide may comprise one or more polypeptide sequences from the first serovar group and one or more polypeptide sequences from the second serovar group. Accordingly, the invention includes a composition comprising a first amino acid sequence and a second amino acid sequence, said first amino acid sequence selected from a *Chlamydia trachomatis* antigen or a fragment thereof, such as the LcrE antigen, from the first serovar group and said second amino acid sequence selected from a *Chlamydia trachomatis* antigen or a fragment thereof, such as the LcrE antigen, from the second serovar group. Preferably, the first and second amino acid sequences in the hybrid polypeptide comprise difference epitopes.

The hybrid polypeptide may comprise one or more the antigens of the invention, such as the LcrE polypeptide sequence(s) from across the *Chlamydia trachomatis* serovars. Accordingly, the invention includes a composition comprising a first LcrE amino acid sequence and a second LcrE amino acid sequence, said first amino acid sequence selected from an LcrE *Chlamydia trachomatis* antigen or a fragment thereof from the *Chlamydia trachomatis* Serovar E and said second amino acid sequence selected from a *Chlamydia trachomatis* antigen or a fragment thereof from *Chlamydia trachomatis* Serovar D. Preferably, the first and second amino acid sequences in the hybrid polypeptide comprise difference epitopes.

Hybrids consisting of amino acid sequences from two, three, four, five, six, seven, eight, nine, or ten LcrE *Chlamydia trachomatis* antigens are preferred. In particular, hybrids consisting of amino acid sequences from two, three, four, or five LcrE *Chlamydia trachomatis* antigens are preferred.

Different hybrid polypeptides may be mixed together in a single formulation. Within such combinations, a *Chlamydia trachomatis* antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula $NH_2$-A-{-X-L-}$_n$-B—COOH, wherein: X is an amino acid sequence of a Chlamydia trachomatis antigen or a fragment thereof from the first serovar group, the second serovar group or the third serovar group; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {-X-L-}, linker amino acid sequence -L- may be present or absent. For instance, when n=2 the hybrid may be $NH_2$—$X_1$-$L_1$-$X_2$-$L_2$-COOH, $NH_2$—

$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. His where n=3, 4, 5, 6, 7, 8, 9, 10 or more). Other suitable linker amino acid sequences will be apparent to those skilled in the art. A useful linker is GSGGGG (SEQ ID 1), with the Gly-Ser dipeptide being formed from a BamHI restriction site, thus aiding cloning and manipulation, and the $(Gly)_4$ tetrapeptide being a typical poly-glycine linker.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art. Most preferably, n is 2 or 3.

The invention also provides nucleic acid encoding hybrid polypeptides of the invention. Furthermore, the invention provides nucleic acid which can hybridise to this nucleic acid, preferably under "high stringency" conditions (e.g. 65° C. in a 0.1×SSC, 0.5% SDS solution).

Polypeptides of the invention can be prepared by various means (e.g. recombinant expression, purification from cell culture, chemical synthesis, etc.) and in various forms (e.g. native, fusions, non-glycosylated, lipidated, etc.). They are preferably prepared in substantially pure form (i.e. substantially free from other *Chlamydial* or host cell proteins).

Nucleic acid according to the invention can be prepared in many ways (e.g. by chemical synthesis, from genomic or cDNA libraries, from the organism itself, etc.) and can take various forms (e.g. single stranded, double stranded, vectors, probes, etc.). They are preferably prepared in substantially pure form (i.e. substantially free from other *Chlamydial* or host cell nucleic acids).

The term "nucleic acid" includes DNA and RNA, and also their analogues, such as those containing modified backbones (e.g. phosphorothioates, etc.), and also peptide nucleic acids (PNA), etc. The invention includes nucleic acid comprising sequences complementary to those described above (e.g. for antisense or probing purposes).

Processes for Making Products of the Invention

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesising at least part of the polypeptide by chemical means.

The invention provides a process for producing nucleic acid of the invention, wherein the nucleic acid is prepared (at least in part) by chemical synthesis.

The invention provides a process for producing nucleic acid of the invention, comprising the step of amplifying nucleic acid using a primer-based amplification method (e.g. PCR).

The invention provides a process for producing a protein complex of the invention, comprising the step of contacting a class I MHC protein with a polypeptide of the invention, or a fragment thereof.

The invention provides a process for producing a protein complex of the invention, comprising the step administering a polypeptide of the invention, or a fragment thereof, to a subject. The process may comprise the further step of purifying the complex from the subject.

The invention provides a process for producing a composition comprising admixing a polypeptide and/or a nucleic acid of the invention with a pharmaceutically acceptable carrier or diluent.

General Features of Polypeptides of the Invention

Polypeptides of the invention can be prepared in various forms (e.g. native, fusions, glycosylated, non-glycosylated etc.).

Polypeptides of the invention may be attached to a solid support.

Polypeptides of the invention may comprise a detectable label (e.g. a radioactive or fluorescent label, or a biotin label).

Polypeptides or the invention may comprise is cell epitopes in addition to T-cell epitopes.

Strains

Preferred polypeptides of the invention comprise an LcrE amino acid sequence found in *C. trachomatis* serovar E, or in one or more of an epidemiologically prevalent serotype.

Preferred polypeptides of the invention comprise an LcrE amino acid sequence found in *C. trachomatis* serovar D, or in one or more of an epidemiologically prevalent serotype.

Preferred polypeptides of the invention comprise an LcrE amino acid sequence found in *C. trachomatis* serovar K, or in one or more of an epidemiologically prevalent serotype.

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2\neq X_3$ (iv) $X_1\neq X_2\neq X_3$ or (v) $X_1=X_3\neq X_2$, etc.

Heterologous Host

Whilst expression of the polypeptides of the invention may take place in *Chlamydia trachomatis*, the invention preferably utilises a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

Immunogenic Compositions and Medicaments

Compositions of the invention are preferably immunogenic compositions, and are more preferably vaccine compositions. The pH of the composition is preferably between 6 and 8, preferably about 7. The pH may be maintained by the use of a buffer. The composition may be sterile and/or pyrogen-free. The composition may be isotonic with respect to humans.

Vaccines according to the invention may either be prophylactic (i.e. to prevent infection) or therapeutic (i.e. to treat infection), but will typically be prophylactic. Accordingly, the invention includes a method for the therapeutic or prophylactic treatment of *Chlamydia trachomatis* infection in an animal susceptible to *Chlamydial* infection comprising administering to said animal a therapeutic or prophylactic amount of the immunogenic compositions of the invention. Preferably, the immunogenic composition comprises a combination of *Chlamydia trachomatis* variant mutations said combination selected from the group consisting of two, three, four, five, six, seven or all eight *Chlamydia trachomatis* LcrE antigen mutations found across the different *Chlamydia trachomatis* serovars. Still more preferably, the combination consists of all eight *Chlamydia trachomatis* LcrE antigen variant or mutations found across the different *Chlamydia trachomatis* serovars.

By way of example, a composition of the present invention may include a combination of *Chlamydia trachomatis trachomatis* antigens, said combination comprising at least one LcrE antigen selected from the group consisting of: (1) Genome GO/86; (2) Genome Cev-1; (3) Genome Cev2; (4) Genome Cev4; (5) Genome Cev5; (5) Genome Cev8; (6) Genome ATTC-E; (7) Genome ATTC-F; (8) Genome ATTC-G; (9) Genome ATTC-H; (10) Genome ATTC-I, (11) Genome ATTC-J and (12) Genome ATTC-K. The combination may further be combined with an immunoregulatory agent or agents, such as Alum and CpG or AlOH and CpG. The compositions of the invention may further comprise antigens derived from one or more sexually transmitted diseases in addition to *Chlamydia trachomatis trachomatis*. Preferably the antigen is derived from one or more of the following sexually transmitted diseases, for example, *N. gonorrhoeae*, human papilloma virus, *Treponema pallidum*, herpes simplex virus (HSV-1 or HSV-2), HIV (HIV-1 or HIV-2), or *Haemophilus ducreyi*.

In one preferred embodiment, the present invention provides immunogenic compositions that may cover the range of mutations for an antigen, such as *Chlamydia trachomatis* LcrE across the serovars rather than tailoring the immunogenic composition to a specific mutation. For example, a *Chlamydia trachomatis* LcrE Serovar E immunogenic composition may comprise an LcrE sequence comprising all eight mutations across all 5 alleles for Serovar E. Alternatively, a mixture of mutations across different *Chlamydia trachomatis* Serovar alleles could cover the mutations in Serovar E and in Serovars other than Serovar E and thus confer cross-serovar protection. As one example, the 8 amino acid substitutions may include the 4 amino acid substitutions seen in the J serovar.

In one particularly preferred embodiment, the immunogenic composition comprises one or more *Chlamydia* antigen (s) which elicits a neutralising antibody response and one or more *Chlamydia* antigen(s) which elicit a cell mediated immune response. In this way, the neutralising antibody response prevents or inhibits an initial *Chlamydia* infection while the cell-mediated immune response capable of eliciting an enhanced Th1 cellular response which prevents ascending and/or spreading infection. Preferably, the immunogenic composition comprises one or more surface antigens and one or more cytoplasmic antigens. Preferably the immunogenic composition comprises one or more LcrE antigens or the like and one or other antigens, such as a cytoplasmic antigen, such as pgp3 or the like, capable of eliciting a Th1 cellular response.

Further Antigens

The compositions of the invention may further comprise antigens derived from one or more sexually transmitted diseases in addition to *Chlamydia trachomatis*. Preferably the antigen is derived from one or more of the following sexually transmitted diseases: *N. gonorrhoeae* {e.g. 19, 20, 21, 22}; human papilloma virus; *Treponema pallidum*; herpes simplex virus (HSV-1 or HSV-2); HIV (HIV-1 or HIV-2); and *Haemophilus ducreyi*. Further antigens for inclusion may be, for example:

- a saccharide antigen from *N. meningitidis* serogroup A, C, W135 and/or Y, such as the oligosaccharide disclosed in ref. 23 from serogroup C {see also ref. 24} or the oligosaccharides of ref. 25.
- antigens from *Helicobacter pylori* such as CagA {26 to 29}, VacA {30, 31}, NAP {32, 33, 34}, HopX {e.g. 35}, HopY {e.g. 35} and/or urease.
- a saccharide antigen from *Streptococcus pneumoniae* {e.g. 36, 37, 38}.
- a protein antigen from *Streptococcus pneumoniae* {e.g. 39}.
- an antigen from hepatitis A virus, such as inactivated virus {e.g. 40, 41}.
- an antigen from hepatitis B virus, such as the surface and/or core antigens {e.g. 41, 42}.
- an antigen from hepatitis C virus {e.g. 43}.
- a diphtheria antigen, such as a diphtheria toxoid {e.g. chapter 3 of ref. 44} e.g. the $CRM_{197}$ mutant {e.g. 45}.
- a tetanus antigen, such as a tetanus toxoid {e.g. chapter 4 of ref. 44}.
- an antigen from *Bordetella pertussis*, such as pertussis holotoxin (PT) and filamentous haemagglutinin (FHA) from *B. pertussis*, optionally also in combination with pertactin and/or agglutinogens 2 and 3 {e.g. refs. 46 & 47}; whole-cell pertussis antigen may also be used.
- a saccharide antigen from *Haemophilus influenzae* B {e.g. 24}.
- polio antigen(s) {e.g. 48, 49} such as OPV or, preferably, IPV.
- an antigen from *N. gonorrhoeae* {e.g. 50, 51, 52, 53} (such as Ng13, Ng576 (PPIase or Mip) or NgpIIII)
- (see, for example, WO 99/57280. WO 00/66791, WO 02/79243, and WO 04/112832)
- a protein antigen from *N. meningitidis* serogroup B {e.g. refs. 54 to 65}
- an outer-membrane vesicle (OMV) preparation from *N. meningitidis* serogroup B, such as those disclosed in refs. 66, 67, 68, 69, etc.
- an antigen from *Chlamydia trachomatis* or *Chlamydia pneumoniae* {e.g. refs. 70 to 76}
- (eg Cpn0324 which is the *Chlamydia trachomatis* pneumonia LcrE equivalent)
- an antigen from *Porphyromonas gingivalis* {e.g. 77}.
- an antigen from *Treponema pallidum*.
- rabies antigen(s) {e.g. 78} such as lyophilised inactivated virus {e.g. 79, RabAvert™}.
- measles, mumps and/or rubella antigens {e.g. chapters 9, 10 & 11 of ref. 44}.
- influenza antigen(s) {e.g. chapter 19 of ref. 44}, such as the haemagglutinin and/or neuraminidase surface proteins.
- antigen(s) from a paramyxovirus such as respiratory syncytial virus (RSV {80, 81}) and/or parainfluenza virus (PIV3 {82}).
- an antigen from *Moraxella catarrhalis* {e.g. 83}.
- an antigen from *Streptococcus pyogenes* (group A streptococcus) {e.g. 84, 85, 86}.

- an antigen from *Streptococcus agalactiae* (group B streptococcus) {e.g. 87}.
- an antigen from *Staphylococcus aureus* {e.g. 88}.
- an antigen from *Bacillus anthracis* {e.g. 89, 90, 91}.
- a papillomavirus antigen e.g. from any HPV type.
- a herpes simplex virus antigen e.g. from HSV-1 or HSV-2.
- an antigen from a virus in the flaviviridae family (genus flavivirus), such as from yellow fever virus, Japanese encephalitis virus, four serotypes of Dengue viruses, tick-borne encephalitis virus, West Nile virus.
- an antigen from a HIV e.g. a HIV-1 or HIV-2.
- an antigen from a rotavirus.
- a pestivirus antigen, such as from classical porcine fever virus, bovine viral diarrhoea virus, and/or border disease virus.
- a parvovirus antigen e.g. from parvovirus B19.
- a coronavirus antigen e.g. from the SARS coronoavirus.
- a cancer antigen, such as those listed in Table 1 of ref. 92 or in tables 3 & 4 of ref. 93.

The composition may comprise one or more of these further antigens. The composition may include at least one further bacterial antigen and/or at least one further viral antigen. It is preferred that combinations of antigens should be based on shared characteristics e.g. antigens associated with respiratory diseases, antigens associated with enteric diseases, antigens associated with sexually-transmitted diseases, etc.

A preferred composition comprises: (1) at least t of the *Chlamydia trachomatis* antigens from either the first serovar group or the second serovar group, where t is 2, 3, 4, 5, 6, 7, 8, 9, 10, 11, 12 or 13, preferably t is five; (2) one or more antigens from another sexually transmitted disease. Preferably, the sexually transmitted disease is selected from the group consisting of herpes simplex virus, preferably HSV-1 and/or HSV-2; human papillomavirus; *N. gonorrhoeae; Treponema pallidum*; and *Haemophilus ducreyi*. These compositions can thus provide protection against the following sexually-transmitted diseases: *Chlamydia trachomatis*, genital herpes, genital warts, gonorrhoea, syphilis and chancroid (See, Ref. 94).

Where a saccharide or carbohydrate antigen is used, it is preferably conjugated to a carrier protein in order to enhance immunogenicity {e.g. refs. 95 to 104}. Preferred carrier proteins are bacterial toxins or toxoids, such as diphtheria or tetanus toxoids. The $CRM_{197}$ diphtheria toxoid is particularly preferred {105}. Other carrier polypeptides include the *N. meningitidis* outer membrane protein {106}, synthetic peptides {107, 108}, heat shock proteins {109; 110}, pertussis proteins {111, 112}, protein D from *H. influenzae* {113}, cytokines {114}, lymphokines, hormones, growth factors, toxin A or B from *C. difficile* {115}, iron-uptake proteins {116}, etc. Where a mixture comprises capsular saccharides from both serogroups A and C, it may be preferred that the ratio (w/w) of MenA saccharide:MenC saccharide is greater than 1 (e.g. 2:1, 3:1, 4:1, 5:1, 10:1 or higher). Different saccharides can be conjugated to the same or different type of carrier protein. Any suitable conjugation reaction can be used, with any suitable linker where necessary.

Toxic protein antigens may be detoxified where necessary e.g. detoxification of pertussis toxin by chemical and/or genetic means.

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the composition will typically be present at a concentration of at least 1 μg/ml each. In general, the concentration of any given antigen will be sufficient to elicit an immune response against that antigen.

As an alternative to using protein antigens in the composition of the invention, nucleic acid encoding the antigen may be used {e.g. refs. 117 to 125}. Protein components of the compositions of the invention may thus be replaced by nucleic acid (preferably DNA e.g. in the form of a plasmid) that encodes the protein.

Combination Therapies

The immunogenic compositions of the present invention may be administered in combination with an antibiotic treatment regime. In one embodiment, the antibiotic is administered prior to administration of the antigen of the invention or the composition comprising the antigen of the invention, such as the LcrE immunogenic composition. In another embodiment, the antibiotic is administered subsequent to the administration of the antigen of the invention or the composition comprising the antigen of the invention, such as the LcrE immunogenic composition. Examples of antibiotics suitable for use in the treatment of *Chlamydia trachomatis* include but are not limited to azithromycin or a derivative thereof as set out in WO 98/17280 or cyclosporin as set out in WO 04/047759.

Preferably, the immunogenic composition comprises one or more variant *Chlamydia trachomatis* Type Three Secretion System (TTSS) protein(s).

Preferably, the immunogenic composition comprises one or more variant *Chlamydia trachomatis* Type Three Secretion System (TTSS) protein(s) with an amino acid sequence selected from the group consisting of SEQ ID Nos 29-45 or SEQ ID Nos 1-13 or SEQ ID Nos 17-45 or SEQ ID Nos 47-180 or SEQ ID No 54, 109, 110 or 111 or SEQ ID No 66, 129 or 130 or SEQ ID Nos 181, 182, 183 and/or 184.

By way of background information, the TTSS is a complex protein secretion and delivery machine or apparatus, which may be located on the Elementary Body (EB) and which allows an organism, such as *Chlamydia*, to maintain its intracellular niche by injecting proteins, such as bacterial effector proteins (which may act as anti-host virulence determinants) into the cytosol of a eukaryotic cell in order to establish the bacterial infection and to modulate the host cellular functions. These injected proteins (the TTSS effector proteins) can have various effects on the host cell which include but are not limited to manipulating actin and other structural proteins and modification of host cell signal transduction systems. The injected (or translocated) proteins or substrates of the TTTS system may also be processed and presented by MHC-class I molecules.

Not all the proteins secreted by a Type III secretion system are delivered into the host cell or have effector function. For example, several Type III proteins are involved in the secretion process itself, its regulation or the translocation of effector proteins through the host cell membrane. By way of example, CT089 also known as Low Calcium Response Element (LcrE) or CoPn—which is the *Chlamydia* outer protein homologue of YopN) is thought to act as a peripherally associated regulator that prevents secretion (of possible pre-synthesised proteins) in the absence of proper signals from the host cell. In effect, it "plugs" the terminal end of the secretion system until an inductive signal is received. Although the Elementary Body (EB) is regarded as "metabolically inert", it has been postulated that the *Chlamydial* TTS system located on the (EB) is triggered by membrane contact and is capable of releasing pre-formed "payload" proteins. The current hypothesis is that Type Three Secretion System (TTSS)

becomes active during the intracellular phase of the chlamydial replicative cycle for the secretion of proteins into the host cell cytoplasm and for the insertion of chlamydial proteins (like the Inc set) into the inclusion membrane that separates the growing chlamydial microcolony from the host cell cytoplasm (see Montigiani et al (2002) Infection and Immunity 70(1); 386-379).

By way of example, the LcrE (CT089) protein is thought to act as a kind of "molecular syringe", injecting effector proteins directly across bacterial and eukaryotic cell membranes into the target cell cytoplasm. As *Chlamydia* bacteria reside in membrane bound vacuoles termed inclusions, it has also been postulated that the *Chlamydia* TTSS probably translocates proteins into, across or through the vacuolar membrane (ie the inclusion membrane) as well as the plasma membrane (see for example Stephens et al 1998 Science (282); 754-759). Immunoblot analysis indicates that both CopN (CT089) and Scc1 (CT088) are present in both chlamydial developmental forms and whole-culture lysates 20 h after infection. Analysis of infected monolayers by indirect immunofluorescence reveals that CopN localised to both bacteria and the inclusion membrane whereas Scc1 was detected only in chlamydiae. Based upon these observations, it appears that, although CoPn is directly associated with chlamydiae, it can also be secreted and associate with the inclusion membrane (see Fields and Hackstadt (2000) Molecular Microbiology 38(5); 1048-1060).

EXAMPLES

The present invention will be defined only by way of example. It will be understood that the invention has been described by way of example only and modifications may be made whilst remaining within the scope and spirit of the invention.

Example 1

Purpose of Example I (i) to evaluate the degree of allelic variation of possible *Chlamydia* vaccine candidates in 13 *Chlamydia trachomatis* clinical isolates corresponding to eight different *Chlamydia* serovars; and (ii) to evaluate the degree of antigenic variation in *Chlamydial* isolates which have, so far, been classified only on the basis of major outer membrane protein (MOMP) variants Isolates Examined 8 isolates were obtained from the ATCC (American Type Culture Collection).

According to the ATCC catalogue these strains were isolated in the USA from patient genital or ocular swabs in the years ranging from 1959 and 1974.

Six Italian isolates belonging to 5 different prevalent *Chlamydia* serovars were also examined. These *Chlamydial* strains were isolated from patients with inflammation symptoms consistent with *Chlamydia* infection, the patients being examined at the Policlinico St. Orsola, Bologna, Italy in a time period approximately around 1998 to 2001.

These isolates were serotyped by described RFLP (restriction fragment length polymorphism) methods assessing sequence variation within the gene ompl, encoding the protein MOMP (major outer membrane protein).

As mentioned earlier, MOMP is a major immunogen in *Chlamydia trachomatis* (CT) infections and provides the basis for serotype or serovar classification of CT strains.

Methodology

Genomic DNA was extracted from EB or CT infected cells, and DNA segments expected to contain the genes to be studies were amplified by PCR. The amplified segments were purified and sequenced in an automatic DNA sequencer, following normal DNA sequencing procedures. As range of specialized software was used, including the GCG package.

Protein sequences encoded by the sequences so obtained were compared to those reported from the only fully sequenced, serovar-D genome (D/UW-3/CX) of *C. trachomatis* available in public databases.

Amino-acid substitutions in the proteins encoded by each gene were scored against the corresponding alleles in the only fully sequenced genome of *C. trachomatis*, i.e. in the reference genome from serotype-D strain UW-3/Cx.

Serotype Assignment

Apart from the use of the RFLP technique, serotyping was mostly carried out by monoclonal antibody typing. As mentioned above, monoclonal antibody typing (ie standard serotype specific monoclonal typing) was the main serotyping procedure used before PCR technology became available.

Results

Table 3 illustrates that allelic variation can also be found for different *Chlamydia trachomatis* antigens across the serovars. For example, Table 3 illustrates the assessment of allelic variation of 6 genes in 14 different CT clinical isolates comprising 8 different serovars. As Table 3 shows, it was found that that most allelic variation was seen for LcrE (CT089) in the E serovar where 5 alleles with a maximum of 8 amino acid substitution points were found over the 421 amino acid sequence. Allele 5 with 8 amino acid substitutions was found to be identical in two isolates (Cev8 Servar E and ATCC E) which was a highly surprising and unexpected finding given that these two E serovars (European and American) have significantly divergent origins.

The least allelic variation was seen for OmpH-like (CT242), ArtJ (CT381), DnaK (CT396) and Hypothetical (CT398) antigens where only two alleles with a maximum of 1-2 amino acid substitution points were found. An intermediate allelic variation was seen for PepA (CT045) where 3 alleles with a maximum of 4 amino acid substitution points over a 499 amino acid sequence were found.

Summary Results

Genotyping was carried out from serovars from different collections, the ATCC collection and the Italian (Cevenini) collection. The ATCC and Cevenini collections are not connected in either source or time (ATCC collection approximately 30-40 years old, whereas the Cevenini collection is approximately 5 years old). Given these geographical and temporal differences between the two collections, it was surprising and unexpected to find that the LcrE amino acid equence from the ATCC Serovar E (SEQ ID NO: 1) has the same eight mutations as that seen in the amino acid sequence from LcrE Italian (Cevenini) Serovar E (cev-8) (SEQ ID NO: 12).

It was wholly unexpected to find that amino acid sequences from different sources and from different, time periods and having been exposed to different immunological pressures would result in the same set of 8 mutations in the LcrE Serovar E sequence. It was also discovered that the LcrE from ATCC Serovar J (SEQ ID NO: 6) has the same three mutations as that seen in the LcrE Italian (Cevenini) Serovar J (cev-5) (SEQ ID NO: 11). Similarly, it was discovered that the LcrE from ATTC Serovar H (SEQ ID NO: 4) has the same three mutations as ATCC Serovar J (SEQ ID NO: 6 and SEQ ID NO: 11. These sequences are also from different sources, different time periods, and different immunological pressures, however the mutations are the same in each of the pairings. Even sequences without identical mutations were still similar. For example, GO 86 Serovar D and LcrE from, Italian (Cevenini) Servar J (cev-1) unexpectedly matched in 3 of the four mutations.

No mutations were noted in the LcrE from ATCC Serovar F, G, I, K, Cev-2 (Serovar G), Cev-4 (Serovar H), or consensus sequences SEQ ID NOS: 14, 15, 17, 22, 24, 25, and 26. This was also an unexpected finding in view of the fact that the different sequences were also exposed to different immunologic pressures in different geographical locations over different periods of time.

Overall Result Summary

Overall, the genotyping results for 6 Chlamydia antigens across 13 isolates corresponding to 8 different *Chlamydia* serovars show a high degree of amino acid sequence conservation, particularly within the same serovar, with allelic variations due to a limited amount of unique single-amino acid substitutions.

However, in the case of LcrE (CT089), a higher than expected number of single amino acid substitution was observed, indicating the likelihood that the LcrE protein is subjected to a greater immunological pressure than the other *Chlamydia* antigens assessed (these being CT242, CT381, CT396, CT398 and CT045), and that the peptides surrounding these amino acid substitutions are likely to be epitopic regions (either B-cell epitopes involved in Ab-Ag interactions and/or T-cell epitopes capable of eliciting *Chlamydia trachomatis* specific cell mediated immune responses). In particular, the exisence of two high frequency mutation positions at residues 64 and 162 of the LcrE sequence is surprising and unexpected and is likely to be associated with the presence of epitopic regions capable of eliciting immunogenic response in a subject.

Serovar specific alterations in immunogenicity can be utilized to tailor specific diagnostic or therapeutic (eg immunological) treatments for different patient profiles (for example, including but not limited to adolescent girls, sex workers (eg prostitutes), homosexuals, etc.)

Example 2

LcrE Epitope Mapping

The LcrE reference sequence from *Chlamydia trachomatis*. Strain D/UW-3/CX is provided as SEQ ID NO: 28 (below) which also shows a summary of the all of the allelic mutation points detected in the various *Chlamydia trachomatis* serovar isolates: The underlined regions in SEQ ID No 28 surrounding the point mutations correspond with either B and/or T cell epitopic peptide regions. The first mutation point at residue 64—underlined in the following epitope region KKK GEK—corresponds with a high frequency mutation point or hypervariable region and is also likely to be associated with a T and/or B-cell epitope region.

SEQ ID NO: 28

```
MTASGGAGGLGSTQTVDVARAQAAAATQDAQEVIGSQEASEASMLKGCED
LINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLI
QTAPSDGKLKSILIQAKHQLMSQNPQAIVGGRNVLLASETFASRANTSPS
SLRSLYFQVTSSPSNCANLHQMLASYLPSEKTAVMEFLVNGMVADLKSEG
PSIPPAKLQVYMTELSNLQALHSVNSFFDRNIGNLENSLKHEGHAPIPSL
TTGNLTKTFLQLVEDKFPSSSKAQKALNELVGPDTGPQTEVLNLFFRALN
GCSPRIFSGAEKKQQLASVITNTLDAINADNEDYPKPGDFPRSSFSSTPP
HAPVPQSEIPTSPTSTQPPSP
```

Thus, mutation points detected in the isolates were at position 64, 126, 157, 162, 179, 207, 217, 220, 275, and 420 (see Table 7). Based on the observed mutations in the isolates, antigenic peptides were determined using the method of Kolaskar and Tongaonkar (Kolaskar et al., "A semi-empirical method for prediction of antigenic determinants on protein antigens", FEBS Lett. Dec. 10, 1990; 276(1-2): 172-4), incorporated herein in its entirety. Briefly, predictions are based on a table that reflects the occurrence of amino acid residues in experimentally known segmental epitopes. Segments are only reported if they have a minimum size of 8 residues. The reported accuracy of the method is about 75%. Using this method, 17 antigenic determinants in the sequence for LcrE *Chlamydia trachomatis* antigen were determined as summarized in the following Table 2 above.

TABLE 7

| LcrE Amino acid residue | Reference amino acid | Mutated amino acid |
|---|---|---|
| X1 = 64 | Glycine (G) | Glutamic acid (E) |
| X2 = 126 | Aspartic acid (D) | Glutamic acid (E) or Asparagine (N) |
| X3 = 157 | Glycine (G) | Arginine ® |
| X4 = 162 | Threonine (T) | Alanine (A) |
| X5 = 179 | Valine (V) | Isoleucine (I) |
| X6 = 207 | Phenylalanine (F) | Leucine (L) |
| X7 = 217 | Alanine (A) | Aspartic Acid (D) |
| X8 = 220 | Histidine (H) | Arginine ® |
| X9 = 275 | Asparagine (N) | Aspartic acid (D) |
| X10 = 420 | Serine (S) | Proline (P) |

Example 3

Epitope Mapping for *Chlamydia* (eg LcrE) Antigens

Epitope mapping of all the LcrE serovar variants is carried out as follows: A mouse model of genital tract infection as described above and in WO 05/002619 is used. All the LcrE variants are expressed as recombinant proteins, methodology for which is also described in WO 05/002619. Mice are immunised with the recombinant LcrE variants (with and without *Chlamydia trachomatis* challenge). The spleen cells from immunised mice (with and without *Chlamydia trachomatis* challenge) are then isolated and pulsed with LcrE specific peptides, set out as SEQ ID Nos 47-98 below. The spleen cell response to each of LcrE specific peptides is then assessed in terms of the presence or absence of spleen cell proliferation, mediator response such as, for eg, Th1 or Th2 cell response as determined by various tests described above. A particularly preferred peptide for pulsing spleen cells and for evaluating the humoural and cellular immune response in a subject is set out as SEQ ID No 54 below. This 15mer peptide comprises the region corresponding to the N-terminal segment surrounding the first high frequency (7/14) mutation point or hypervariable region identified at residue 64 in the LcrE amino acid sequence when evaluated across 13 *Chlamydia* serovars. A second particularly preferred peptide for pulsing spleen cells and for evaluating the humoural and cellular immune response in a subject is set out as SEQ ID No 66 below. This 15mer peptide comprises the region corresponding to the segment surrounding the second high frequency (7/14) mutation point or hypervariable region identified at residue 162 in the LcrE amino acid sequence when evaluated across 13 *Chlamydia* serovar isolates. Other particularly preferred peptides include those which comprise the epitopes set out in SEQ ID Nos 29-45 (see Table 2) and SEQ ID Nos 181, 182, 183 and/or 184.

These peptides, in particular SEQ ID No 54 and/or SEQ ID No 66 and/or SEQ ID Nos 181, 182, 183 and/or 184 can be used in the immunisation schedule described in Example 5 to evaluate their prophylactic and therapeutic efficacy and, of course, for diagnostic purposes. Similar methodology can be applied to map epitopes for other *Chlamydia* antigens, such as but not limited to CT242, CT381, CT396, CT398 and CT045.

LcrE Peptides for Epitope Mapping

LcrE Serotype D Reference Strain (Allele 1) from Serovar D/UW-3/CX

```
MTASGGAGGLGSTQTVDVARAQAAAATQDAQEVIGSQEASEASMLKGC
EDLINPAAATRIKKKGEKFESLEARRKPTADKAEKKSESTEEKGDTPL
EDRFTEDLSEVSGEDFRGLKNSFDDDSSPDEILDALTSKFSDPTIKDL
ALDYLIQTAPSDGKLKSTLIQAKHQLMSQNPQAIVGGRNVLLASETFA
SRANTSPSSLRSLYFQVTSSPSNCANLHQMLASYLPSEKTAVMEFLVN
GMVADLKSEGPSIPPAKLQVYMTELSNLQALHSVNSFFDRNIGNLENS
LKHEGHAPIPSLTTGNLTKTFLQLVEDKFPSSSKAQKALNELVGPDTG
PQTEVLNLFFRALNGCSPRIFSGAEKKQQLASVITNTLDAINADNEDY
PKPGDFPRSSFSSTPPHAPVPQSEIPTSPTSTQPPSP (421 aa)
```

Splitting the LcrE sequence into peptide for Epitope mapping can be carried out in several ways by varying the length of individual peptides and changing the extent of overlapping. One example based on the published reference sequence of CT LcrE, and choosing to use overlapping 15nmers progressively shifted by 8 amino acid residues is set out as follows:

Split in 51 Overlapping 15nmers Plus 1 End-14nmer Shifted by 8 Residues

```
 1.   MTASGGAGGLGSTQT   (SEQ ID No 47)
 2.   GLGSTQTVDVARAQA   (SEQ ID No 48)
 3.   DVARAQAAAATQDAQ   (SEQ ID No 49)
 4.   AATQDAQEVIGSQEA   (SEQ ID No 50)
 5.   VIGSQEASEASMLKG   (SEQ ID No 51)
 6.   EASMLKGCEDLINPA   (SEQ ID No 52)
 7.   EDLINPAAATRIKKK   (SEQ ID No 53)
 8.   ATRIKKKGEKFESLE   (SEQ ID No 54)
 9.   EKFESLEARRKPTAD   (SEQ ID No 55)
10.   RRKPTADKAEKKSES   (SEQ ID No 56)
11.   AEKKSESTEEKGDTP   (SEQ ID No 57)
12.   EEKGDTPLEDRFTED   (SEQ ID No 58)
13.   EDRFTEDLSEVSGED   (SEQ ID No 59)
14.   SEVSGEDFRGLKNSF   (SEQ ID No 60)
15.   RGLKNSFDDDSSPDE   (SEQ ID No 61)
16.   DDSSPDEILDALTSK   (SEQ ID No 62)
17.   LDALTSKFSDPTIKD   (SEQ ID No 63)
18.   SDPTIKDLALDYLIQ   (SEQ ID No 64)
19.   ALDYLIQTAPSDGKL   (SEQ ID No 65)
```

-continued

```
20.   APSDGKLKSTLIQAK   (SEQ ID No 66)
21.   STLIQAKHQLMSQNP   (SEQ ID No 67)
22.   QLMSQNPQAIVGGRN   (SEQ ID No 68)
23.   AIVGGRNVLLASETF   (SEQ ID No 69)
24.   LLASETFASRANTSP   (SEQ ID No 70)
25.   SRANTSPSSLRSLYF   (SEQ ID No 71)
26.   SLRSLYFQVTSSPSN   (SEQ ID No 72)
27.   VTSSPSNCANLHQML   (SEQ ID No 73)
28.   ANLHQMLASYLPSEK   (SEQ ID No 74)
29.   SYLPSEKTAVMEFLV   (SEQ ID No 75)
30.   AVMEFLVNGMVADLK   (SEQ ID No 76)
31.   GMVADLKSEGPSIPP   (SEQ ID No 77)
32.   EGPSIPPAKLQVYMT   (SEQ ID No 78)
33.   KLQVYMTELSNLQAL   (SEQ ID No 79)
34.   LSNLQALHSVNSFFD   (SEQ ID No 80)
35.   SVNSFFDRNIGNLEN   (SEQ ID No 81)
36.   NIGNLENSLKHEGHA   (SEQ ID No 82)
37.   LKHEGHAPIPSLTTG   (SEQ ID No 83)
38.   IPSLTTGNLTKTFLQ   (SEQ ID No 84)
39.   LTKTFLQLVEDKFPS   (SEQ ID No 85)
40.   VEDKFPSSSKAQKAL   (SEQ ID No 86)
41.   SKAQKALNELVGPDT   (SEQ ID No 87)
42.   ELVGPDTGPQTEVLN   (SEQ ID No 88)
43.   PQTEVLNLFFRALNG   (SEQ ID No 89)
44.   FFRALNGCSPRIFSG   (SEQ ID No 90)
45.   SPRIFSGAEKKQQLA   (SEQ ID No 91)
46.   EKKQQLASVITNTLD   (SEQ ID No 92)
47.   VITNTLDAINADNED   (SEQ ID No 93)
48.   INADNEDYPKPGDFP   (SEQ ID No 94)
49.   PKPGDFPRSSFSSTP   (SEQ ID No 95)
50.   SSFSSTPPHAPVPQS   (SEQ ID No 96)
51.   HAPVPQSEIPTSPTS   (SEQ ID No 97)
52.   IPTSPTSTQPPSP     (SEQ ID No 98)
```

Example 4

Epitope Mapping for *Chlamydia* (eg LcrE) Antigens

Epitope mapping of all the LcrE serovar variants is carried out as follows: A mouse model of genital tract infection as described above and in WO 05/002619 is used. All the LcrE variants are expressed as recombinant proteins, methodology for which is also described in WO 05/002619. Mice are immunised with the recombinant LcrE variants (with and without *Chlamydia trachomatis* challenge). The spleen cells from immunised mice (with and without *Chlamydia tra-*

*chomatis* challenge) are then isolated and pulsed with LcrE specific peptides, set out as SEQ ID Nos 99-180 below. The spleen cell response to each of LcrE specific peptides is then assessed in terms of the presence or absence of spleen cell proliferation, mediator response such as, for eg, Th1 or Th2 cell response as determined by various tests described above. Three particularly preferred peptides for pulsing spleen cells and for evaluating the humoural and cellular immune response in a subject are set out as SEQ ID No 109, 110 and 111 below. These 15mer peptides comprises the region corresponding to the N-terminal segment surrounding the first high frequency (7/14) mutation point or hypervariable region identified at residue 64 in the LcrE amino acid sequence when evaluated across 13 *Chlamydia* serovars. Other particularly preferred peptide for pulsing spleen cells and for evaluating the humoural and cellular immune response in a subject are set, out as SEQ ID No 129 and 130 below. These 15mer peptide comprises the region corresponding to the segment surrounding the second high frequency (7/14) mutation point or hypervariable region identified at residue 162 in the LcrE amino acid sequence when evaluated across 13 *Chlamydia* serovar isolates. Other particularly preferred peptides include those which comprise the epitopes set out in SEQ ID Nos 29-45 (see Table 2) and SEQ ID Nos 181, 182, 183 and/or 184.

These peptides, in particular SEQ ID Nos 109, 110 and 111 and/or SEQ ID No 129, 130 and/or SEQ ID Nos 181, 182, 183 and/or 184 can be used in the immunisation schedule described in Example 5 to evaluate their prophylactic and therapeutic efficacy and, of course, for diagnostic purposes. Similar methodology can be applied to map epitopes for other *Chlamydia* antigens, such as but not limited to CT242, CT381, CT396, CT398 and CT045

LcrE Peptides for serE Mapping

LcrE found in serotype E strains (LcrE allele 5).

Allele 5 has 8 amino acid changes as compared to the published LcrE of the Serovar D sequenced genome.

Also, 2 of these changes are regarded "conservative" while 6 of the changes are regareded "non-conservative" (see Table 4 below).

LcrE Found in Serotype E Strains (LcrE Allele 5).

```
MTASGGAGGLGSTQTVDVARAQAAAATQDAQEVIGSQEASEASMLKGC
EDLINPAAATRIKKKEEKFESLEARRKPTADKAEKKSESTEEKGDTPL
EDRFTEDLSEVSGEDFRGLKNSFDDDSSPEEILDALTSKFSDPTIKDL
ALDYLIQTAPSDRKLKSALIQAKHQLMSQNPQAIVGGRNVLLASETFA
SRANTSPSSLRSLYLQVTSSPSNCDNLRQMLASYLPSEKTAVMEFLVN
GMVADLKSEGPSIPPAKLQVYMTELSNLQALHSVDSFFDRNIGNLENS
LKHEGHAPIPSLTTGNLTKTFLQLVEDKFPSSSKAQKALNELVGPDTG
PQTEVLNLFFRALNGCSPRIFSGAEKKQQLASVITNTLDAINADNEDY
PKPGDFPRSSFSSTPPHAPVPQSEIPTSPTSTQPPSP (421 aa)
```

The following example shows the splitting the serovar-E LcrE sequence into peptide for Epitope mapping by choosing to use overlapping 15nmers progressively shifted by 5 amino acid residues.

Split in 81 Overlapping 15nmers Plus 1 end-16nmer, Shifted by 5 Residues

| | | |
|---|---|---|
| 1. | MTASGGAGGLGSTQT | (SEQ ID No 99) |
| 2. | GAGGLGSTQTVDVAR | (SEQ ID No 100) |
| 3. | GSTQTVDVARAQAAA | (SEQ ID No 101) |
| 4. | VDVARAQAAAATQDA | (SEQ ID No 102) |
| 5. | AQAAAATQDAQEVIG | (SEQ ID No 103) |
| 6. | ATQDAQEVIGSQEAS | (SEQ ID No 104) |
| 7. | QEVIGSQEASEASML | (SEQ ID No 105) |
| 8. | SQEASEASMLKGCED | (SEQ ID No 106) |
| 9. | EASMLKGCEDLINPA | (SEQ ID No 107) |
| 10. | KGCEDLINPAAATRI | (SEQ ID No 108) |
| 11. | LINPAAATRIKKKEE | (SEQ ID No 109) |
| 12. | AATRIKKKEEKFESL | (SEQ ID No 110) |
| 13. | KKKEEKFESLEARRK | (SEQ ID No 111) |
| 14. | KFESLEARRKPTADK | (SEQ ID No 112) |
| 15. | EARRKPTADKAEKKS | (SEQ ID No 113) |
| 16. | PTADKAEKKSESTEE | (SEQ ID No 114) |
| 17. | AEKKSESTEEKGDTP | (SEQ ID No 115) |
| 18. | ESTEEKGDTPLEDRF | (SEQ ID No 116) |
| 19. | KGDTPLEDRFTEDLS | (SEQ ID No 117) |
| 20. | LEDRFTEDLSEVSGE | (SEQ ID No 118) |
| 21. | TEDLSEVSGEDFRGL | (SEQ ID No 119) |
| 22. | EVSGEDFRGLKNSFD | (SEQ ID No 120) |
| 23. | DFRGLKNSFDDDSSP | (SEQ ID No 121) |
| 24. | KNSFDDDSSPEEILD | (SEQ ID No 122) |
| 25. | DDSSPEEILDALTSK | (SEQ ID No 123) |
| 26. | EEILDALTSKFSDPT | (SEQ ID No 124) |
| 27. | ALTSKFSDPTIKDLA | (SEQ ID No 125) |
| 28. | FSDPTIKDLALDYLI | (SEQ ID No 126) |
| 29. | IKDLALDYLIQTAPS | (SEQ ID No 127) |
| 30. | LDYLIQTAPSDRKLK | (SEQ ID No 128) |
| 31. | QTAPSDRKLKSALIQ | (SEQ ID No 129) |
| 32. | DRKLKSALIQAKHQL | (SEQ ID No 130) |
| 33. | SALIQAKHQLMSQNP | (SEQ ED No 131) |
| 34. | AKHQLMSQNPQAIVG | (SEQ ID No 132) |
| 35. | MSQNPQAIVGGRNVL | (SEQ ID No 133) |
| 36. | QAIVGGRNVLLASET | (SEQ ID No 134) |
| 37. | GRNVLLASETFASRA | (SEQ ID No 135) |
| 38. | LASETFASRANTSPS | (SEQ ID No 136) |
| 39. | FASRANTSPSSLRSL | (SEQ ID No 137) |

-continued

| | | |
|---|---|---|
| 40. | NTSPSSLRSLYLQVT | (SEQ ID No 138) |
| 41. | SLRSLYLQVTSSPSN | (SEQ ID No 139) |
| 42. | YLQVTSSPSNCDNLR | (SEQ ID No 140) |
| 43. | SSPSNCDNLRQMLAS | (SEQ ID No 141) |
| 44. | CDNLRQMLASYLPSE | (SEQ ID No 142) |
| 45. | QMLASYLPSEKTAVM | (SEQ ID No 143) |
| 46. | YLPSEKTAVMEFLVN | (SEQ ID No 144) |
| 47. | KTAVMEFLVNGMVAD | (SEQ ID No 145) |
| 48. | EFLVNGMVADLKSEG | (SEQ ID No 146) |
| 49. | GMVADLKSEGPSIPP | (SEQ ID No 147) |
| 50. | LKSEGPSIPPAKLQV | (SEQ ID No 148) |
| 51. | PSIPPAKLQVYMTEL | (SEQ ID No 149) |
| 52. | AKLQVYMTELSNLQA | (SEQ ID No 150) |
| 53. | YMTELSNLQALHSVD | (SEQ ID No 151) |
| 54. | SNLQALHSVDSFFDR | (SEQ ID No 152) |
| 55. | LHSVDSFFDRNIGNL | (SEQ ID No 153) |
| 56. | SFFDRNIGNLENSLK | (SEQ ID No 154) |
| 57. | NIGNLENSLKHEGHA | (SEQ ID No 155) |
| 58. | ENSLKHEGHAPIPSL | (SEQ ID No 156) |
| 59. | HEGHAPIPSLTTGNL | (SEQ ID No 157) |
| 60. | PIPSLTTGNLTKTFL | (SEQ ID No 158) |
| 61. | TTGNLTKTFLQLVED | (SEQ ID No 159) |
| 62. | TKTFLQLVEDKFPSS | (SEQ ID No 160) |
| 63. | QLVEDKFPSSSKAQK | (SEQ ID No 161) |
| 64. | KFPSSSKAQKALNEL | (SEQ ID No 162) |
| 65. | SKAQKALNELVGPDT | (SEQ ID No 163) |
| 66. | ALNELVGPDTGPQTE | (SEQ ID No 164) |
| 67. | VGPDTGPQTEVLNLF | (SEQ ID No 165) |
| 68. | GPQTEVLNLFFRALN | (SEQ ID No 166) |
| 69. | VLNLFFRALNGCSPR | (SEQ ID No 167) |
| 70. | FRALNGCSPRIFSGA | (SEQ ID No 168) |
| 71. | GCSPRIFSGAEKKQQ | (SEQ ID No 169) |
| 72. | IFSGAEKKQQLASVI | (SEQ ID No 170) |
| 73. | EKKQQLASVITNTLD | (SEQ ID No 171) |
| 74. | LASVITNTLDAINAD | (SEQ ID No 172) |
| 75. | TNTLDAINADNEDYP | (SEQ ID No 173) |
| 76. | AINADNEDYPKPGDF | (SEQ ID No 174) |
| 77. | NEDYPKPGDFPRSSF | (SEQ ID No 175) |
| 78. | KPGDFPRSSFSSTPP | (SEQ ID No 176) |
| 79. | PRSSFSSTPPHAPVP | (SEQ ID No 177) |

-continued

| | | |
|---|---|---|
| 80. | SSTPPHAPVPQSEIP | (SEQ ID No 178) |
| 81. | HAPVPQSEIPTSPTS | (SEQ ID No 179) |
| 82. | QSEIPTSPTSTQPPSP | (SEQ ID No 180) |
| | IKKKGEKFE | (SEQ ID No 181) |
| | IKKKEEKFE | (SEQ ID No 182) |
| | KLKSTLIQA | (SEQ ID No 183) |
| | KLKSALIQA | (SEQ ID No 184) |

TABLE 4

| LcrE Amino acid (AA) residue no | AA in LcrE D serovar | AA in LcrE E serovar | Nature of the mutation |
|---|---|---|---|
| 64 | G | E | Not conserved |
| 126 | D | E | Conserved |
| 157 | G | R | Not conserved |
| 162 | T | A | Not conserved |
| 207 | F | L | Not conserved |
| 217 | A | D | Not conserved |
| 220 | H | R | Not conserved |
| 275 | N | D | Conserved |

Example 5

Immunization with LcrE Antigen or Combinations Thereof

Immunizations with LcrE alone and in combination with LcrE from different *Chlamydia trachomatis* serovars and/or in combination with other *Chlamydia trachomatis* proteins and/or one or more other STD antigen(s) either alone with or without an immunoregulatory agent.

The following example illustrates immunization with various combinations of CT LcrE antigens in a mouse model. The recombinant CT LcrE antigens are prepared and characterised using, for eg, the procedures described in WO 05/002619 and Finco et al (2005) Vaccine 23; 1178-1188 and Sambri et al (2004) Vaccine 22 (9-10); 1131-7).

In this Example, immunization is shown with a combination of 1 or 2 or 3 or 4 or 5 LcrE antigens from different *Chlamydia trachomatis* serovars were prepared as described above. The antigens are expressed and purified. Compositions of antigen combinations are then prepared comprising 1 or 2 or 3 or 4 or 5 LcrE antigens per composition (and containing 15 μg of each antigen per composition).

CD1 mice are divided into seven groups (5-6 mice per group for groups 1 through 6; 3 to 4 mice for groups 5, 6, 7, 8 and 9), and immunized as follows:

TABLE 5

Immunization Schedule for Example 5

| Group | Immunizing Composition | Route of Delivery |
|---|---|---|
| 1 | Mixture of 1 or 2 or 3 or 4 or 5 LcrE antigens (15 µg/each) + CFA | Intra-peritoneal or intra-nasal |
| 2 | Mixture of 1 or 2 or 3 or 4 or 5 antigens (15 µg/each) + AlOH (200 µg) | Intra-peritoneal or intra-nasal |
| 3 | Mixture of 1 or 2 or 3 or 4 or 5 antigens (15 µg/each) + CpG (10 ug) | Intra-peritoneal or intra-nasal |
| 4 | Mixture of 1 or 2 or 3 or 4 or 5 antigens (15 µg/each) + AlOH (200 µg) + CpG (10 µg) | Intra-peritoneal or intra-nasal |
| 5 | Complete Freunds Adjuvant (CFA) | Intra-peritoneal or intra-nasal |
| 6 | Mixture of 1 or 2 or 3 or 4 or 5 antigens (5 µg/each) + LTK63 (5 µg) | Intra-peritoneal or Intranasal |
| 7 | AlOH (200 µg) + CpG (10 µg) | Intra-peritoneal or intra-nasal |
| 8 | CpG (10 µg) | Intra-peritoneal or intra-nasal |
| 9 | LTK63 (5 µg) | Intra-peritoneal or intra-nasal |

Mice are immunized at two week intervals. Two weeks after the last immunization, all mice are challenged by intra-vaginal infection with the appropriate *Chlamydia* serovar, such as but not limited to *Chlamydia trachomatis* serovar D. When mucosal immunization (eg intra-nasal(in)) is used, the animal model is also challenged mucosally to test the protective effect of the mucosal immunogen.

Example 6

Immunization with LcrE Antigen or Combinations Thereof

The following Example shows immunizations with LcrE alone and in combination with LcrE from different *Chlamydia trachomatis* serovars and/or in combination with other *Chlamydia trachomatis* proteins either alone with or without an immunoregulatory agent.

Specifically, in this example, immunization is shown with a combination of 1 or 2 or 3 or 4 or 5 LcrE antigens from different *Chlamydia trachomatis* serovars were prepared as described above. The antigens are expressed and purified. Compositions of antigen combinations are then prepared comprising 1 or 2 or 3 or 4 or 5 antigens per composition (and containing 15 μg of each antigen per composition).

TABLE 6

| Immunization Schedule for Example 6 | | | |
|---|---|---|---|
| Group | Immunising Composition | ImmunoRegulatory Agent | Route of Delivery |
| 1 (Test Group) | Combos of 1 or 2 or 3 or 4 or 5 LcrE antigens from different *Chlamydia trachomatis* serovars were prepared as described above. The antigens are expressed and purified. Compositions of antigen combinations are then prepared comprising five antigens per composition (and containing 15 μg of each antigen per composition). (15 ug/each CT antigen) | CFA | Intra-peritoneal (i.p.) |
| 2 (Test Group) | As for test 1 (15 ug/each CT antigen) | AlOH (200 ug) and CpG (10 ug) | Intra-peritoneal (i.p.) |
| 3 (Test Group) | As for test 1 (15 ug/each CT antigen) | AlOH (200 ug) alone | Intra-peritoneal (i.p.) |
| 4 (Test Group) | As for test 1 (15 ug/each CT antigen) | CpG (10 ug) alone | Intra-peritoneal (i.p.) |
| 5 (Negative control) | Complete Freunds Adjuvant (CFA) alone | | Intra-peritoneal (i.p.) |
| 6 (Negative Control) | AlOH (200 μg) + CpG (10 μg) | | Intra-peritoneal (i.p.) |
| 7 (Positive Control) (Protection control) | Live Elementary Body (EB) from *Chlamydia trachomatis* (twice - pre-challenge + challenge) | | Intra-peritoneal (i.p.) |

TABLE 6-continued

| Immunization Schedule for Example 6 | | | |
|---|---|---|---|
| Group | Immunising Composition | ImmunoRegulatory Agent | Route of Delivery |
| 8 (Infection control) | Live Elementary Body (EB) from *Chlamydia trachomatis* (once - challenge only) | | Intra-peritoneal (i.p.) |

Mouse Model for in-vivo screening for CT protective antigens: A Mouse Model of *Chlamydia trachomatis* genital infection for determining in-vivo protective effect of CT antigens (resolution of a primary *Chlamydia trachomatis* infection) was used. The model used is described as follows: Balb/c female mice 4-6 weeks old were used. The mice were immunized infra-peritoneally (ip) with a mixture of 1 or 2 or 3 or 4 or 5 recombinant CT antigens, such as but not limited to LcrE, as set out in Table 5 or 6 above. These CT antigens were determined to be FACS positive and/or neutralizing. Three doses of the 1 or 2 or 3 or 4 or 5 LcrE antigen mixture were given at a concentration of 15 ug per dose. The mice were given hormonal treatment 5 days prior to challenge with 2.5 mg of DepoProvera (medroxyprogesterone acetate).

Test Challenges: The mice were challenged intravaginally with $10^5$ IFU of purified EBs (Serovar D), 2 weeks after the last immunization dose. A read out of vaginal swabs every 7 days up to 28 days after challenge. The following assays were also carried out on pre-challenge sera: Serological analysis: FACS, WB, Neutralization assay and ELISA. The ELISA were performed by coating plates with each recombinant antigen and testing the reaction of pre-challenge immune sera from single mice immunized with the combination of 1 or 2 or 3 or 4 or 5 CT LcrE antigens. The data is expressed as the mean value calculated for each group expressed as mean ELISA units. The *Chlamydia trachomatis* specific antibody type (IgG, IgA etc) and isotype was checked in serum post immunization but pre-challenge. The purpose of the serum studies was to determine how the mice responded to immunization with the CT LcrE antigen combinations. The purpose of the vaginal washes was to determine how the mice responded to the *Chlamydia trachomatis* bacterial challenge. *Chlamydia trachomatis* specific antibody analyses in terms of antibody type (IgG and IgA) and antibody subtype were also carried out on the vaginal washes. Negative Controls: The negative control used was the immunoregulatory agent alone (eg CFA or AlOH and/or CpG).

Positive "live" EB controls: The positive control used was an extract from live *Chlamydia trachomatis* Elementary Bodies (EBs). Here the mice were infected with live *Chlamydia trachomatis* EB at the same time that the test CT combination antigens are being administered. The "live" EB positive control animals were infected for about 1.5 months (ie 6 weeks) (because 3 doses of CT antigenic combinations were administered every 2 weeks (ie over a total of 6 weeks). The animals (mice) infected with "live" EB developed a natural immunity and resolved the infection (because *Chlamydia* infection in mice is a transient infection). When the mice were vaccinated with the CT antigenic combinations were then challenged with "live" EB, the positive control "live" EB mice were also re-challenged (ie they were given a second dose of "live" EB). As the "live" EB positive control group developed a natural immunity, they cleared the second re-challenge quickly.

Infection Control: In this group, the mice were only challenged with "live" EB at the same time that the "Positive Live EB controls were re-challenged and the test CT group was challenged. The purpose of this control group was to check for a possible protective effect from the negative control group (ie the group immunized with immunoregulatory agent alone).

Example 7

In Vitro Model for the Selection of Antigens Inducing a CD4 Th1 Response

Th1-type cytokines, such as IL-12 and IFN-□, have been proposed to be important for resolution of chlamydial infection. Indeed, mice deficient in IFN-□ are unable to control chlamydial infection in the genital tract as *Chlamydia* disseminates to systemic sites [126, 127].

Two immunological screening approaches to identify *Chlamydia* antigens capable of inducing *Chlamydia*-specific IFN□ producing $CD4^+$ T cells have been devised: 1) after experimental mouse infection with *Chlamydia trachomatis*, and 2) following mouse immunization with *Chlamydia* recombinant proteins. These antigens would be the most promising candidates to confer $CD4^+$-mediated protection.

In the first approach: CD4 Th1 stimulation upon EB (Elementary Bodies) infection): LPS-free purified recombinant surface antigens are screened for their capacity to stimulate CD4+/IFN-gamma, producing T lymphocytes from mice resolving a primary Ct infection and thereby protected against further infections. This approach allows the identification of antigens which could induce a CD4 Th1 response during natural infection.

In the second approach: CD4 Th1 induction upon immunization with CT recombinant antigens: purified recombinant antigens are used to immunize mice and antigen specific CD4 T cell response is analysed ex vivo by stimulating spleen cells with Ct EB and LPS-free antigens. This approach allows the priming of in vivo antigen-specific CD4-Th1 cells that could potentially be involved in recognition of EB.

In the first approach female BALB/c mice 6-7 weeks old were pretreated with 2.5 mg of medroxy-progesterone acetate (Depo-Provera) on day-5 and then infected intravaginally at day 0 by depositing 15 ml of SPG (250 mM Sucrose, 10 mM Sodium Phosphate, 5 mM L-Glutamic acid) containing $10^6$ IFU of *C. trachomatis* serovar D. Seven days post infection the course of infection was monitored by swabbing the vaginal vault and determining the number of recovered IFUs on LL-CMK2 cell monolayers using indirect immunofluorescence.

Splenocytes were prepared from spleens of mice infected with Chlamydia trachomatis (10 days post infection) and non-infected controls. Spleens of each group of mice were pooled and dispersed manually. Splenocytes were cultured in RPMI 1640 medium supplemented with 25 mM HEPES buffer, 100 UI/ml penicillin, 100 ug/ml streptomycin, 50 uM 2-mercaptoethanol, 0.15 mM L-glutamine, sodium pyruvate, vitamins, a cocktail of non-essential amino acids and 2.5% heat inactivated fetal calf serum.

Freshly prepared splenocytes from infected mice and non infected controls were stimulated for 4 hours in round-bottom 96 well plates with 20 ug/ml of various *Chlamydia trachomatis* recombinant antigens in the presence of 1 ug/ml anti-CD28. As positive controls of stimulation 1 ug/ml of anti-CD3 and 10 ug/ml of heat inactivated whole *C. trachomatis* Elementary Bodies were used. For the analysis of antigen induced intracellular cytokine expression, 2.5 ug/ml Brefeldin-A (Sigma) was added overnight. At the end of the stimulation period cells were fixed with 2% paraformaldeide and subsequently permeabilized with PBS-1%BSA-0.5% saponin. Fixed cells were stained for 30 min at room temperature with the following antibodies: antiCD4-FITC, antiCD8-PerCp, antiIFNg-APC and antilL5-PE (all BD Pharmingen).

Stained cells were analyzed for cytokine production on a LSRII cytometer with a DIVA software.

In the second approach, mice were immunized intramusculary on days 1, 14 and 28 with a panel of recombinant chlamydial proteins with proper adjuvants. A week after the last immunization, PBMC were isolated and assessed by spleen harvesting as described above, in the presence of syngeneic irradiated APC. Ex vivo stimulation was carried out for 24 hours using whole *Chlamydia trachomatis* EBs and LPS-free antigens. Following stimulation the cells were analysed for cytokine production (IFN-0 and IL-5) as described above.

For the second approach, splenocytes were prepared from spleens of mice immunized with the recombinant antigens (3 doses 20 ug, with AlOH+CpG) and adjuvant-immunized mice. Spleens of each group of mice were pooled and dispersed manually. Splenocytes were cultured in RPMI 1640 medium supplemented with 25 mM HEPES buffer, 100 UI/ml penicillin, 100 ug/ml streptomycin, 50 uM 2-mercaptoethanol, 0.15 mM L-glutamine, sodium pyruvate, vitamins, a cocktail of non-essential amino acids and 2.5% heat inactivated fetal calf serum.

Flow cytometry analysis of antigen-induced cytokine expression for the second approach was carried out in the same way as the first approach except in this case antigen specific CD4 T cell response is analysed ex vivo by stimulating spleen cells with Ct EB and LPS-free antigens.

Both screening are carried out using multi-parametric FACS analysis to assess the cytokine expression profile of antigen-specific Th1-cells.

Results from the first approach indicated that 13 out of 70 tested antigens were found to be CD4-Th1 inducers (CT681, CT823, CT043, CT587, CT153, CT480, CT016, CT341, CT372, CT396, CT600, CT601, CT711. Noteworthy among these CT4-Th1 inducing antigens is CT396.

Results for the second approach indicated that both CT396 and CT381 are able to induce strong antigen-specific and *Chlamydia* specific responses.

Results from the first and second approach are expressed in terms of the frequency of EB-specific and antigen-specific CD4-IFN gamma+T lymphocytes in 10000 CD4+ cells derived from splenocytes of mice immunized with the antigens (formulated with LTK63+CpG as adjuvant), upon stimulation with either EB or the antigen itself as compared to that obtained from adjuvant-immunized mice.

For CT381, the frequency of EB-specific and CT381-specific CD4-IFN gamma+T lymphocytes is 450 (vs 131 of adjuvant immunized mice) and 109 (vs 17 of adjuvant immunized mice) respectively.

For CT396, the frequency of EB-specific and CT396-specific CD4-IFN gamma+T lymphocytes is 612 (vs 309 of adjuvant immunized mice) and 488 (vs 17 of adjuvant immunized mice) respectively.

These results indicate that both ArtJ (CT381) and DnaK (CT396) are examples of *Chlamydia* antigens capable of producing high frequencies of cells that are capable of producing IFN-gamma.

Overall Summary

The present invention provides variant LcrE sequences and/or combinations of variant LcrE sequences across the *Chlamydia trachomatis* serovars. Such changes in LcrE genotypes across the *Chlamydia trachomatis* serovars are likely to correspond with changes in LcrE phenotypes, in particular, with changes in immunogenicity. The present invention also provides peptides surrounding or associated with the amino acid substitutions, in particular, peptides surrounding or associated with high frequency mutated amino acid positions or hypervariable regions, which are likely to be B and/or T cell epitopic regions capable of eliciting *Chlamydia* specific cell mediated immune responses. The variant LcrE sequences and/or combinations of the variant LcrE sequences and/or epitope regions associated with the variant LcrE sequences are useful as immunogens and/or in the preparation of immunogenic compositions for preventing and/or treating and/or diagnosing *Chlamydia* infections.

The present invention also provides variant Omp-H-like sequences and/or combinations of variant Omp-H-like sequences across the *Chlamydia trachomatis* serovars. Such changes in Omp-H-like genotypes across the *Chlamydia trachomatis* serovars are likely to correspond with changes in Omp-H-like phenotypes, in particular, with changes in immunogenicity. The present invention also provides peptides surrounding or associated with the amino acid substitutions, in particular, peptides surrounding or associated with high frequency mutated amino acid positions or hypervariable regions, which are likely to be B and/or T cell epitopic regions capable of eliciting *Chlamydia* specific immune responses. The variant Omp-H-like sequences and/or combinations of the variant LcrE sequences and/or epitope regions associated with the variant Omp-H-like sequences are useful as immunogens and/or in the preparation of immunogenic compositions for preventing and/or treating and/or diagnosing *Chlamydia* infections.

The present invention also provides variant PepA sequences and/or combinations of variant PepA sequences across the *Chlamydia trachomatis* serovars. Such changes in PepA genotypes across the *Chlamydia trachomatis* serovars are likely to correspond with changes in PepA phenotypes, in particular, with changes in immunogenicity. The present invention, also provides peptides surrounding or associated with the amino acid substitutions, in particular, peptides surrounding or associated with high frequency mutated amino acid positions or hypervariable regions, which are likely to be B and/or T cell epitopic regions capable of eliciting *Chlamydia* specific immune responses. The variant PepA sequences and/or combinations of the variant PepA sequences and/or epitope regions associated with the variant PepA sequences are useful as immunogens and/or in the preparation of immunogenic compositions for preventing and/or treating and/or diagnosing *Chlamydia* infections.

The present invention also provides variant ArtJ sequences and/or combinations of variant ArtJ sequences across the *Chlamydia trachomatis* serovars. Such changes in ArtJ genotypes across the *Chlamydia trachomatis* serovars are likely to correspond with changes in ArtJ phenotypes, in particular, with changes in immunogenicity. The present invention also provides peptides surrounding or associated with the amino acid substitutions, in particular, peptides surrounding or associated with high frequency mutated amino acid positions or hypervariable regions, which are likely to be B and/or T cell epitopic regions capable of eliciting *Chlamydia* specific immune responses. The variant ArtJ sequences and/or combinations of the variant ArtJ sequences and/or epitope regions associated with the variant ArtJ sequences are useful as immunogens and/or in the preparation of immunogenic compositions for preventing and/or treating and/or diagnosing *Chlamydia* infections.

The present invention also provides variant DnaK sequences and/or combinations of variant DnaK sequences across the *Chlamydia trachomatis* serovars. Such changes in DnaK genotypes across the *Chlamydia trachomatis* serovars are likely to correspond with changes in DnaK phenotypes, in particular, with changes in immunogenicity. The present invention also provides peptides surrounding or associated with the amino acid substitutions, in particular, peptides surrounding or associated with high frequency mutated amino acid positions or hypervariable regions, which are likely to be B and/or T cell epitopic regions capable of eliciting *Chlamydia* specific immune responses. The variant DnaK sequences and/or combinations of the variant DnaK sequences and/or epitope regions associated with the variant DnaK sequences are useful as immunogens and/or in the preparation of immunogenic compositions for preventing and/or treating and/or diagnosing *Chlamydia* infections.

The present invention also provides variant Hypothetical (CT398) sequences and/or combinations of variant DnaK sequences across the *Chlamydia trachomatis* serovars. Such changes in Hypothetical (CT398) genotypes across the *Chlamydia trachomatis* serovars are likely to correspond with changes in Hypothetical (CT398) phenotypes, in particular, with changes in immunogenicity. The present invention also provides peptides surrounding or associated with the amino acid substitutions, in particular, peptides surrounding or associated with high frequency mutated amino acid positions or hypervariable regions, which are likely to be B and/or T cell epitopic regions capable of eliciting *Chlamydia* specific immune responses. The variant sequences and/or combinations of the variant Hypothetical (CT398) sequences and/or epitope regions associated with the variant Hypothetical (CT398) sequences are useful as immunogens and/or in the preparation of immunogenic compositions for preventing and/or treating and/or diagnosing *Chlamydia* infections.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be covered by the present invention.

REFERENCES

Moulder J W. 1991. Interaction of *Chlamydia trachomatise* and host cells in vitro. Microbiol Rev. 55: 143-90.

Stephens R S. 1999. Genomic autobiographies of Chlamidiae. American Society for Microbiology Press. Washington D.C., USA. 9-27.

Schachter, J., and Stamm W. E. 1999. *Chlamydia trachomatis*. In P. R. Murray, Baron E. J., Pfaller M. A., Tenover F. C. and Yolken R. H. Manual of Clinical Microbiology. American Society for Microbiology Press. Washington D.C., USA. 669-677.

An B B, Adamis A P. 1998. *Chlamydia trachomatisl* ocular diseases. Int Ophthalmol Clin. 38: 221-30.

Schachter J. 1999. Infection and disease epidemiology. American Society for Microbiology Press. Washington D.C., USA. 139-170.

Centers for Disease Control and Prevention. 1993. Recommendations for the prevention and management of *Chlamydia trachomatis trachomatis* infections. Morbid. Mortal. Wkly Rep. 42:1-39.

Washington A E, Johnson R E, Sanders L L Jr. 1987. *Chlamydia trachomatis trachomatis* infections in the United States. What are they costing us? *JAMA*. 257: 2070-2.

Schachter, J., and P. B. Wyrick. 1994. Culture and isolation of *Chlamydia trachomatis* trachomatis. Methods Enzymol. 236:377-390.

Stephens R S, Kalman S, Lammel C, Fan J, Marathe R, Aravind L, Mitchell W, Olinger L, Tatusov R L, Zhao Q, Koonin E V, Davis R W. 1998. Genome sequence of an obligate intracellular pathogen of humans: *Chlamydia trachomatis trachomatis*. Science 282: 754-9.

Gardy J L, Spencer C, Wang K, Ester M, Tusnady G E, Simon I, Hua S, deFays K, Lambert C, Nakai K, Brinkman F S. PSORT-B: Improving protein subcellular localization prediction for Gram-negative bacteria. Nucleic Acids Res. Jul. 1, 2003; 31(13):3613-7.

Montigiani, S., F. Falugi, M. Scarselli, O. Finco, R. Petracca, G. Galli, M. Mariani, R. Manetti, M. Agnusdei, R. Cevenini, M. Donati, R. Nogarotto, N. Norais, I. Garaguso, S. Nuti, G. Saletti, D. Rosa, G. Ratti, and G. Grandi. 2002. Genomic approach for analysis of surface proteins in *Chlamydia trachomatis* pneumoniae. Infect Immun 70:368-79.

Towbin, H., T. Staehelin, and J. Gordon. 1979. Electrophoretic transfer of proteins from polyacrylamide gels to nitrocellulose sheets: procedure and some applications. Proc. Natl. Acad. Sci. USA 76:4350-4354.

Laemmli, U. K. 1970. Cleavage of structural proteins during the assembly of the head of bacteriophage T4. Nature 227: 680-685.

Young, I. T. 1977. Proof without prejudice: use of the Kolmogorov-Smirnov test for the analysis of histograms from flow systems and other sources. J Histochem Cytochem 25:935-41.

Bini, L., Sanchez-Campillo, M., Santucci, A., Magi, B., Marzocchi, B., Comanducci, M., Christiansen, G., Birkelund, S., Cevenini, R., Vretou, E., Ratti, G. and Pallini, V. (1996). Mapping of *Chlamydia trachomatis trachomatis* proteins by immobiline-polyacrylamide two-dimensional electrophoresis: spot identification by N-terminal sequencing and immunoblotting. *Electrophoresis* 17, 185-90.

Christiansen, G., Boesen, T., Hjerno, K., Daugaard, L., Mygind, P., Madsen, A. S., Knudsen, K., Falk, E. and Birkelund, S. (1999). Molecular biology of *Chlamydia trachomatis* pneumoniae surface proteins and their role in immunopathogenicity. *Am Heart J* 138, S491-5.

Comanducci, M., Cevenini, R., Moroni, A., Giuliani, M. M., Ricci, S., Scarlato, V. and Ratti, G. (1993). Expression of a plasmid gene of *Chlamydia trachomatis trachomatis* encoding a novel 28 kDa antigen. *J Gen Microbiol* 139, 1083-92.

Gardy, J. L., Spencer, C., Wang, K., Ester, M., Tusnady, G. E., Simon, I., Hua, S., deFays, K., Lambert, C., Nakai, K. and Brinkman, F. S. (2003). PSORT-B: Improving protein subcellular localization prediction for Gram-negative bacteria. *Nucleic Acids Res* 31, 3613-7.

Grandi, G. (2001). Antibacterial vaccine design using genomics and proteomics. *Trends Biotechnol* 19, 181-8.

Grimwood, J., Olinger, L. and Stephens, R. S. (2001). Expression of *Chlamydia trachomatis* pneumoniae polymorphic membrane protein family genes. *Infect Immun* 69, 2383-9.

Kawa, D. E. and Stephens, R. S. (2002). Antigenic topology of *Chlamydia trachomatisl* PorB protein and identification of targets for immune neutralization of infectivity. *J Immunol* 168, 5184-91.

Knudsen, K., Madsen, A. S., Mygind, P., Christiansen, G. and Birkelund, S. (1999). Identification of two novel genes encoding 97- to 99-kilodalton outer membrane proteins of *Chlamydia trachomatis* pneumoniae. *Infect Immun* 67, 375-83.

Montigiani, S., Falugi, F., Scarselli, M., Finco, O., Petracca, R., Galli, G., Mariani, M., Manetti, R., Agnusdei, M., Cevenini, R., Donati, M., Nogarotto, R., Norais, N., Garaguso, I., Nuti, S., Saletti, G., Rosa, D., Ratti, G. and Grandi, G. (2002). Genomic approach for analysis of surface proteins in *Chlamydia trachomatis* pneumoniae. *Infect Immun* 70, 368-79.

Moulder, J. W. (1991). Interaction of *Chlamydia trachomatise* and host cells in vitro. *Microbiol Rev* 55, 143-90.

Mygind, P. H., Christiansen, G., Roepstorff, P. and Birkelund, S. (2000). Membrane proteins PmpG and PmpH are major constituents of *Chlamydia trachomatis trachomatis* L2 outer membrane complex. *FEMS Microbiol Lett* 186, 163-9.

Pedersen, A. S., Christiansen, G. and Birkelund, S. (2001). Differential expression of Pmp10 in cell culture infected with *Chlamydia trachomatis* pneumoniae CWL029. *FEMS Microbiol Lett* 203, 153-9.

Pizza, M., Scarlato, V., Masignani, V., Giuliani, M. M., Arico, B., Comanducci, M., Jennings, G. T., Baldi, L., Bartolini, E., Capecchi, B., Galeotti, C. L., Luzzi, E., Manetti, R., Marchetti, E., Mora, M., Nuti, S., Ratti, G., Santini, L., Savino, S., Scarselli, M., Storni, E., Zuo, P., Broeker, M., Hundt, E., Knapp, B., Blair, E., Mason, T., Tettelin, H., Hood, D. W., Jeffries, A. C., Saunders, N. J., Granoff, D. M., Venter, J. C., Moxon, E. R., Grandi, G. and Rappuoli, R. (2000). Identification of vaccine candidates against serogroup B meningococcus by whole-genome sequencing. *Science* 287, 1816-20.

Schachter, J. and Wyrick, P. B. (1994). Culture and isolation of *Chlamydia trachomatis trachomatis. Methods Enzymol* 236, 377-90.

Shaw, A. C., Gevaert, K., Demol, H., Hoorelbeke, B., Vandekerckhove, J., Larsen, M. R., Roepstorff, P., Holm, A., Christiansen, G. and Birkelund, S. (2002). Comparative proteome analysis of *Chlamydia trachomatis trachomatis* serovar A, D and L2. *Proteomics* 2, 164-86.

Somani, J., Bhullar, V. B., Workowski, K. A., Farshy, C. E. and Black, C. M. (2000). Multiple drug-resistant *Chlamydia trachomatis trachomatis* associated with clinical treatment failure. *J Infect Dis* 181, 1421-7.

Stephens, R. S., Kalman, S., Lammel, C., Fan, J., Marathe, R., Aravind, L., Mitchell, W., Olinger, L., Tatusov, R. L., Zhao, Q., Koonin, E. V. and Davis, R. W. (1998). Genome sequence of an obligate intracellular pathogen of humans: *Chlamydia trachomatis trachomatis. Science* 282, 754-9.

Taraktchoglou, M., Pacey, A. A., Turnbull, J. E. and Eley, A. (2001). Infectivity of *Chlamydia trachomatis trachomatis* serovar LGV but not E is dependent on host cell heparan sulfate. *Infect Immun* 69, 968-76.

Vandahl, B. B., Pedersen, A. S., Gevaert, K., Holm, A., Vandekerckhove, J., Christiansen, G. and Birkelund, S. (2002). The expression, processing and localization of polymorphic membrane proteins in *Chlamydia trachomatis* pneumoniae strain CWL029. *BMC Microbial* 2, 36.

Waldman, F. M., Hadley, W. K., Fulwyler, M. J. and Schachter, J. (1987). Flow cytometric analysis of *Chlamydia trachomatis trachomatis* interaction with L cells. *Cytometry* 8, 55-9.

ENDNOTE CITATIONS USED IN SPECIFICATION

1. Bush, R. M. and Everett, K. D. E. (2001) Molecular Evolution of the *C. trachomatis* trachomatisceae. *Int. J Syst. Evol. Microbiol.* 51:203-220.
2. Kalman et al. (1999) *Nature Genetics* 21:385-389
3. Read et al. (2000) *Nucleic Acids Res* 28:1397-1406
4. Shirai et al. (2000) *Nucleic Acids Res* 28:2311-2314
5. Stephens et al. (1998) *Science* 282:754-759
6. WO99/27105
7. WO00/27994
8. WO99/28475
9. Ward (1995) *Apmis.* 103:769-96.
10. Moulder (1991) *Microbiol Rev* 55(1):143-190.
11. Comanducci et al. (1994) *Infect Immun* 62(12):5491-5497.
12. EP-A-0499681
13. WO95/28487
14. Murdin et al. (1993) *Infect Immun* 61:4406-4414
15. Cerrone et al. (1991) *Infect Immun* 59(1):79-90.
16. Raulston et al. (1993) *J Biol. Chem.* 268:23139-23147.
17. WO03/049762.
18. Gennaro (2000) *Remington: The Science and Practice of Pharmacy.* 20th ed., ISBN: 0683306472.
19. WO99/24578.
20. WO99/36544.
21. WO99/57280.
22. WO02/079243.

{23} Costantino et al. (1992) *Vaccine* 10:691-698.
{24} Costantino et al. (1999) *Vaccine* 17:1251-1263.
{25} WO03/007985.
{26} Covacci & Rappuoli (2000) *J. Exp. Med.* 19:587-592.
{27} WO93/18150.
{28} Covacci et al. (1993) *Proc. Natl. Acad. Sci. USA* 90: 5791-5795.
{29} Tummuru et al. (1994) *Infect. Immun.* 61:1799-1809.
{30} Marchetti et al. (1998) *Vaccine* 16:33-37.
{31} Telford et al. (1994) *J. Exp. Med.* 179:1653-1658.
{32} Evans et al. (1995) *Gene* 153:123-127.
{33} WO96/01272 & WO96/01273, especially SEQ ID NO:6.
{34} WO97/25429.
{35} WO98/04702.
{36} Watson (2000) *Pediatr Infect Dis J* 19:331-332.
{37} Rubin (2000) *Pediatr Clin North Am* 47:269-285, v.
{38} Jedrzejas (2001) *Microbiol Mol Biol Rev* 65:187-207.
{39} WO02/077021.
{40} Bell (2000) *Pediatr Infect Dis J* 19:1187-1188.
{41} Iwarson (1995) *APMIS* 103:321-326.
{42} Gerlich et al. (1990) *Vaccine* 8 Suppl:S63-68 & 79-80.
{43} Hsu et al. (1999) *Clin Liver Dis* 3:901-915.
{44} *Vaccines* (1988) eds. Plotkin & Mortimer. ISBN 0-7216-1946-0.
{45} Del Guidice et al. (1998) *Molecular Aspects of Medicine* 19:1-70.
{46} Gustafsson et al. (1996) *N. Engl. J. Med.* 334:349-355.

{47} Rappuoli et al. (1991) *TIBTECH* 9:232-238.
{48} Sutter et al. (2000) *Pediatr Clin North Am* 47:287-308.
{49} Zimmerman & Spann (1999) *Am Fam Physician* 59:113-118, 125-126.
{50} WO99/24578.
{51} WO99/36544.
{52} WO99/57280.
{53} WO02/079243.
{54} WO99/24578.
{55} WO99/36544.
{56} WO99/57280.
{57} WO00/22430.
{58} WO00/66791.
{59} WO03/020756.
{60} WO01/64920.
{61} WO01/64922.
{62} Tettelin et al. (2000) *Science* 287:1809-1815.
{63} Pizza et al. (2000) *Science* 287:1816-1820.
{64} UK patent application 0227346.4.
{65} UK patent applications 0223741.0, 0305831.0 & 0309115.4.
{66} Bjune et al. (1991) *Lancet* 338(8775):1093-96
{67} WO01/52885.
{68} Fukasawa et al. (1999) *Vaccine* 17:2951-2958.
{69} Rosenqvist et al. (1998) *Dev. Biol. Stand.* 92:323-333.
{70} WO02/02606.
{71} Kalman et al. (1999) *Nature Genetics* 21:385-389.
{72} Read et al. (2000) *Nucleic Acids Res* 28:1397-406.
{73} Shirai et al. (2000) *J. Infect. Dis.* 181(Suppl 3):S524-S527.
{74} WO99/27105.
{75} WO00/27994.
{76} WO00/37494.
{77} Ross et al. (2001) *Vaccine* 19:4135-4142.
{78} Dreesen (1997) *Vaccine* 15 Suppl:S2-6.
{79} *MMWR Morb. Mortal Wkly Rep* Jan. 16, 1998; 47(1):12, 19.
{80} Anderson (2000) *Vaccine* 19 Suppl 1:S59-65.
{81} Kahn (2000) *Curr Opin Pediatr* 12:257-262.
{82} Crowe (1995) *Vaccine* 13:415-421.
{83} McMichael (2000) *Vaccine* 19 Suppl 1:S101-107.
{84} WO02/34771.
{85} Dale (1999) *Infect Dis Clin North Am* 13:227-43, viii.
{86} Ferretti et al. (2001) *PNAS USA* 98: 4658-4663.
{87} WO02/34771.
{88} Kuroda et al. (2001) *Lancet* 357(9264):1225-1240; see also pages 1218-1219.
{89} *J Toxicol Clin Toxicol* (2001) 39:85-100.
{90} Demicheli et al. (1998) *Vaccine* 16:880-884.
{91} Stepanov et al. (1996) *J Biotechnol* 44:155-160.
{92} Rosenberg (2001) *Nature* 411:380-384.
{93} Moingeon (2001) *Vaccine* 19:1305-1326.
94. WO00/15255.
95. Ramsay et al. (2001) *Lancet* 357(9251):195-196.
96. Lindberg (1999) *Vaccine* 17 Suppl 2:S28-36.
97. Buttery & Moxon (2000) *J R Coll Physicians Lond* 34:163-168.
98. Ahmad & Chapnick (1999) *Infect Dis Clin North Am* 13:113-133, vii.
99. Goldblatt (1998) *J. Med. Microbiol.* 47:563-567.
100. European patent 0 477 508.
101. U.S. Pat. No. 5,306,492.
102. International patent application WO98/42721.
103. *Conjugate Vaccines* (eds. Cruse et al.) ISBN 3805549326, particularly vol. 10:48-114.
104. Hermanson (1996) *Bioconjugate Techniques* ISBN: 0123423368 or 012342335X.
105. *Research Disclosure,* 453077 (January 2002)
106. EP-A-0372501
107. EP-A-0378881
108. EP-A-0427347
109. WO93/17712
110. WO94/03208
111. WO98/58668
112. EP-A-0471177
113. WO00/56360
114. WO91/01146
115. WO00/61761
116. WO01/72337
117. Robinson & Torres (1997) *Seminars in Immunology* 9:271-283.
118. Donnelly et al. (1997) *Annu Rev Immunol* 15:617-648.
119. Scott-Taylor & Dalgleish (2000) *Expert Opin Investig Drugs* 9:471-480.
120. Apostolopoulos & Plebanski (2000) *Curr Opin Mol Ther* 2:441-447.
121. Ilan (1999) *Curr Opin Mol Ther* 1:116-120.
122. Dubensky et al. (2000) *Mol Med* 6:723-732.
123. Robinson & Pertmer (2000) *Adv Virus Res* 55:1-74.
124. Donnelly et al. (2000) *Am J Respir Crit Care Med* 162(4 Pt 2):S190-193.
125. Davis (1999) *Mt. Sinai J. Med.* 66:84-90.
[126] Cotter et al. (1997) *Infect. Immun.* 65:2145-2152.
[127] Perry et al. (1997) *J. Immunol.* 158(7):3344-3352.

What is claimed is:

1. An isolated protein consisting of the amino acid sequence SEQ ID NO:46 but for an amino acid substitution at one or more amino acid residues selected from the group consisting of amino acid residues 157, 179, 207, 217, 220, and 420 of SEQ ID NO:46.

2. The protein of claim 1 wherein the amino acid substitution at one or more amino acid residues alters the immunogenicity of the protein.

3. An isolated protein comprising at least 7 consecutive amino acids of the isolated protein of claim 1, wherein the at least 7 consecutive amino acids comprise the one or more amino acid substitutions.

4. An isolated protein comprising the amino acid sequence SEQ ID NO:46 but for an amino acid substitution at one or more amino acid residues selected from the group consisting of amino acid residues 157, 179, 207, 217, 220, and 420.

5. An isolated protein comprising the amino acid sequence SEQ ID NO: 46 but for an amino acid substitution at one or more amino acid residues selected from the group consisting of amino acid residues 157, 179, 207, 217, 220, and 420 of SEQ ID NO: 46.

6. A fragment of the isolated protein of claim 1, wherein the fragment comprises at least 7 consecutive amino acids and wherein the fragment comprises the amino acid substitution at the one or more amino acid residues selected from the group consisting of amino acid residues 157, 179, 207, 217, 220, and 420 of SEQ ID NO:46.

7. The isolated protein of claim 1 which has an amino acid substitution at residue 157 of SEQ ID NO: 46.

8. The isolated protein of claim 1 which has an amino acid substitution at residue 179 of SEQ ID NO: 46.

9. The isolated protein of claim 1 which has an amino acid substitution at residue 207 of SEQ ID NO: 46.

10. The isolated protein of claim 1 which has an amino acid substitution at residue 217 of SEQ ID NO: 46.

11. The isolated protein of claim 1 which has an amino acid substitution at residue 220 of SEQ ID NO: 46.

12. The isolated protein of claim 1 which has an amino acid substitution at residue 420 of SEQ ID NO: 46.

13. The isolated protein of claim 5 which has an amino acid substitution at residue 157 of SEQ ID NO: 46.

14. The isolated protein of claim 5 which has an amino acid substitution at residue 179 of SEQ ID NO: 46.

15. The isolated protein of claim 5 which has an amino acid substitution at residue 207 of SEQ ID NO: 46.

16. The isolated protein of claim 5 which has an amino acid substitution at residue 217 of SEQ ID NO: 46.

17. The isolated protein of claim 5 which has an amino acid substitution at residue 220 of SEQ ID NO: 46.

18. The isolated protein of claim 5 which has an amino acid substitution at residue 420 of SEQ ID NO: 46.

19. The fragment of claim 6 which has an amino acid substitution at residue 157 of SEQ ID NO: 46.

20. The fragment of claim 6 which has an amino acid substitution at residue 179 of SEQ ID NO: 46.

21. The fragment of claim 6 which has an amino acid substitution at residue 207 of SEQ ID NO: 46.

22. The fragment of claim 6 which has an amino acid substitution at residue 217 of SEQ ID NO: 46.

23. The fragment of claim 6 which has an amino acid substitution at residue 220 of SEQ ID NO: 46.

24. The fragment of claim 6 which has an amino acid substitution at residue 420 of SEQ ID NO: 46.

* * * * *